US010557042B2

(12) United States Patent
Lynn et al.

(10) Patent No.: US 10,557,042 B2
(45) Date of Patent: *Feb. 11, 2020

(54) SLIPPERY LIQUID-INFUSED POROUS SURFACES THAT PREVENT MICROBIAL SURFACE FOULING

(71) Applicant: Wisconsin Alumni Research Foundation, Madison, WI (US)

(72) Inventors: David M. Lynn, Middleton, WI (US); Uttam Manna, Guwahati (IN)

(73) Assignee: Wisconsin Alumni Research Foundation, Madison, WI (US)

( * ) Notice: Subject to any disclaimer, the term of this patent is extended or adjusted under 35 U.S.C. 154(b) by 98 days.

This patent is subject to a terminal disclaimer.

(21) Appl. No.: 15/471,628

(22) Filed: Mar. 28, 2017

(65) Prior Publication Data
US 2018/0230318 A1     Aug. 16, 2018

Related U.S. Application Data

(60) Provisional application No. 62/314,282, filed on Mar. 28, 2016.

(51) Int. Cl.
*C09D 5/14* (2006.01)
*C07D 307/12* (2006.01)
*C09D 5/16* (2006.01)
*C07C 233/73* (2006.01)
*C07D 235/28* (2006.01)
*C07D 235/30* (2006.01)
*C07D 307/14* (2006.01)

(52) U.S. Cl.
CPC ............. *C09D 5/14* (2013.01); *C09D 5/1625* (2013.01); *C07C 233/73* (2013.01); *C07D 235/28* (2013.01); *C07D 235/30* (2013.01); *C07D 307/12* (2013.01); *C07D 307/14* (2013.01)

(58) Field of Classification Search
None
See application file for complete search history.

(56) References Cited

U.S. PATENT DOCUMENTS

| 7,642,285 | B2 | 1/2010 | Blackwell et al. | |
| 7,883,720 | B2* | 2/2011 | Lynn | A61K 9/5138 424/280.1 |
| 7,910,622 | B2 | 3/2011 | Blackwell et al. | |
| 8,071,210 | B2 | 12/2011 | Lynn et al. | |
| 8,097,277 | B2* | 1/2012 | Lynn | A61K 9/5138 424/280.1 |
| 8,269,024 | B2 | 9/2012 | Blackwell et al. | |
| 8,324,333 | B2* | 12/2012 | Liu | A61K 47/48176 526/304 |
| 8,367,680 | B2 | 2/2013 | Blackwell et al. | |
| 8,524,368 | B2* | 9/2013 | Lynn | A61K 9/5138 424/280.1 |
| 8,624,063 | B2 | 1/2014 | Blackwell et al. | |
| 8,716,422 | B2* | 5/2014 | Liu | A61K 47/48176 526/304 |
| 8,815,943 | B2 | 8/2014 | Blackwell et al. | |
| 2005/0027064 | A1* | 2/2005 | Lynn | A61K 9/5138 524/555 |
| 2009/0170179 | A1* | 7/2009 | Lynn | C08F 26/06 435/180 |
| 2010/0048736 | A1* | 2/2010 | Liu | A61K 47/48176 514/772.4 |
| 2011/0117138 | A1* | 5/2011 | Lynn | A61K 9/5138 424/400 |
| 2011/0306142 | A1* | 12/2011 | Lynn | G01N 21/21 436/85 |
| 2012/0027833 | A1* | 2/2012 | Zilberman | A61K 9/7007 424/422 |
| 2012/0134926 | A1* | 5/2012 | Lynn | A61K 9/5138 424/9.1 |
| 2013/0122055 | A1* | 5/2013 | Liu | A61K 47/48176 424/400 |
| 2014/0147627 | A1* | 5/2014 | Aizenberg | A61L 15/24 428/141 |
| 2014/0187666 | A1* | 7/2014 | Aizenberg | A61L 33/0094 523/113 |
| 2014/0220617 | A1* | 8/2014 | Yung | A61M 1/36 435/34 |
| 2014/0328999 | A1* | 11/2014 | Aizenberg | A61L 27/56 427/2.26 |
| 2015/0152270 | A1* | 6/2015 | Aizenberg | A61L 29/085 210/500.27 |
| 2015/0173883 | A1* | 6/2015 | Ingber | C09D 5/1662 435/287.2 |
| 2015/0175814 | A1* | 6/2015 | Aizenberg | B08B 17/06 428/312.8 |
| 2015/0196940 | A1* | 7/2015 | Aizenberg | B05D 5/08 428/141 |
| 2015/0209198 | A1* | 7/2015 | Aizenberg | A61L 29/06 604/378 |
| 2017/0022371 | A1 | 1/2017 | Lynn et al. | |
| 2017/0022372 | A1 | 1/2017 | Lynn et al. | |

OTHER PUBLICATIONS

Fabrication of Liquid-Infused Surfaces Using Reactive Polymer Multilayers: Principles for Manipulating the Behaviors and Mobilities of Aqueous Fluids on Slippery Liquid Interfaces, Manna et al., Adv. Mater. 2015, 27, 300 (Year: 2015).*

(Continued)

*Primary Examiner* — Peter A Salamon
(74) *Attorney, Agent, or Firm* — Leydig, Voit & Mayer, Ltd.

(57) ABSTRACT

The present invention provides polymer-based slippery liquid-infused porous surfaces (SLIPS) that can prevent adhesion and colonization by fungal and bacterial pathogens and also kill and/or attenuate the colonization and virulence of non-adherent pathogens in surrounding media. The present approach exploits the polymer and liquid oil phases in these slippery materials to sustain the release of small molecules such as a broad-spectrum antimicrobial agent, an antifungal agent, an antibacterial agent, an agent that modulates bacterial or fungal quorum sensing, an agent that attenuates virulence, or a combination thereof. This controlled release approach improves the inherent anti-fouling properties of SLIPS, has the potential to be general in scope, and expands the potential utility of slippery, non-fouling surfaces in both fundamental and applied contexts.

20 Claims, 20 Drawing Sheets

(56) References Cited

OTHER PUBLICATIONS

Superhydrophobic Polymer Multilayers that Promote the Extended, Long-Term Release of Embedded Water-Soluble Agents, Manna et al., Adv. Mater. 2013, 25, 6405-6409 (Year: 2013).*
Allen et al. (Mar. 14, 2014) "Targeting virulence: can we make evolution-proof drugs?" Nat. Rev. Microbiol. 12:300-308.
Antipov et al. (2001) "Sustained Release Properties of Polyelectrolyte Multilayer Capsules," J. Phys. Chem. B. 105:2281-2284.
Arciola et al. (2012) "Biofilm formation in *Staphylococcus* implant infections. A review of molecular mechanisms and implications for biofilm-resistant materials," Biomaterials. 33:5967-5982.
Bae et al. (Dec. 18, 2013) "25th Anniversary Article: Scalable Multiscale Patterned Structures Inspired by Nature: The Role of Hierarchy," Adv. Mater. 26:675-700.
Bai et al. (2011) "Recent Advances in Colloidal and Interfacial Phenomena Involving Liquid Crystals," Langmuir. 27:5719-5738.
Banerjee et al. (2011) "Antifouling Coatings: Recent Developments in the Design of Surfaces That Prevent Fouling by Proteins, Bacteria, and Marine Organisms," Adv. Mater. 23:690-718.
Barthlott et al. (1997) "Purity of the sacred lotus, or escape from contamination in biological surfaces," Planta. 202:1-8.
Bassler et al. (2006) "Bacterially speaking," Cell. 125:237-246.
Bellanger et al. (Jan. 9, 2014) "Chemical and Physical Pathways for the Preparation of Superoleophobic Surfaces and Related Wetting Theories," Chem. Rev. 114:2694-2716.
Bhargava et al. (1996) "Triclosan: applications and safety," Am. J. Infect. Control. 24:209-218.
Bortleson et al. (1972) "Recent sedimentary history of Lake Mendota, Wis," Environ. Sci. Technol. 6:799-808.
Boudou et al. (2010) "Multiple functionalities of polyelectrolyte multilayer films: new biomedical applications," Adv. Mater. 22:441-467.
Brake et al. (2003) "Biomolecular interactions at phospholipid-decorated surfaces of liquid crystals," Science. 302:2094-2097.
Breitbach et al. (2011) "Surface-mediated release of a synthetic small-molecule modulator of bacterial quorum sensing: Gradual release enhances activity," Chem. Comm. 47:370-372.
Brock et al. (1984) "Significance of algal excretory products for growth of epilimnetic bacteria," Appl. Environ. Microbiol. 47:731-734.
Broderick et al. (2012) "Covalent Layer-by-Layer Assembly of Water-Permeable and Water-Impermeable Polymer Multilayers on Highly Water-Soluble and Water-Sensitive Substrates," Chem. Mater. 24:1786-1795.
Broderick et al. (2012) "In situ Synthesis of Oligonucleotide Arrays on Surfaces Coated with Crosslinked Polymer Multilayers," Chem. Mater. 24:938-945.
Broderick et al. (Jan. 20, 2013) "Surface-mediated release of a small-molecule modulator of bacterial biofilm formation: A non-bactericidal approach to inhibiting biofilm formation in Pseudomonas aeruginosa," Adv. Healthcare Mater. 2:993-1000.
Broderick et al. (Jun. 28, 2014) "Surface coatings that promote rapid release of peptide-based AgrC inhibitors for attenuation of quorum sensing in *Staphylococcus aureus*," Adv. Healthcare Mater. 3:97-105.
Buck et al. (2007) "Layer-by-layer assembly of reactive ultrathin films mediated by click-type reactions of poly(2-alkenyl azlactone)s," Adv. Mater. 19:3951-3955.
Buck et al. (2009) "Chemical Modification of Reactive Multilayered Films Fabricated from Poly(2-alkenyl azlactone)s: Design of Surfaces that Prevent or Promote Mammalian Cell Adhesion and Bacterial Biofilm Growth," Biomacromolecules. 10:1564-1574.
Buck et al. (2010) "Functionalization of Fibers Using Azlactone-Containing Polymers: Layer-by-Layer Fabrication of Reactive Thin Films on the Surfaces of Hair and Cellulose-Based Materials," ACS Appl. Mater. Interfaces. 2:1421-1429.
Buck et al. (2010) "Superhydrophobic thin films fabricated by reactive layer-by-layer assembly of azlactone-functionalized polymers," Chem. Mater. 22:6319-6327.
Buck et al. (Oct. 12, 2011) "Azlactone-functionalized polymers as reactive platforms for the design of advanced materials: Progress in the last ten years," Polym. Chem. 3:66-80.
Busscher et al. (2012) "Biomaterial-associated infection: Locating the finish line in the race for the surface," Sci. Transl. Med. 4:153rv110.
Cai et al. (2014) "Filefish-Inspired Surface Design for Anisotropic Underwater Oleophobicity," Adv. Funct. Mater. 24(6):809-816.
Camilli et al. (2006) "Bacterial small-molecule signaling pathways," Science. 311:1113-1116.
Campoccia et al. (Aug. 15, 2013) "A review of the biomaterials technologies for infection-resistant surfaces," Biomaterials. 34:8533-8554.
Cassie et al. (1944) "Wettability of porous surfaces," Trans. Faraday Soc. 40:546-551.
Chapman et al. (2000) "Surveying for Surfaces that Resist the Adsorption of Proteins," J. Am. Chem. Soc. 122:8303-8304.
Chu et al. (Jan. 31, 2014) "Superamphiphobic surfaces," Chem. Soc. Rev. 43:2784-2798.
Chung et al. (2002) "Methods of Loading and Releasing Low Molecular Weight Cationic Molecules in Weak Polyelectrolyte Multilayer Films," Langmuir. 18:1176-1183.
Clatworthy et al. (2007) "Targeting virulence: a new paradigm for antimicrobial therapy," Nat. Chem. Biol. 3:541-548.
Costerton et al. (1999) "Bacterial biofilms: A common cause of persistent infections," Science. 284:1318-1322.
Daniel et al. (Jun. 2013) "Lubricant-infused micro/nano-structured surfaces with tunable dynamic omniphobicity at high temperatures," Appl. Phys. Lett. 102:231603.
De Kievit et al. (2001) "Quorum-sensing genes in Pseudomonas aeruginosa biofilms: their role and expression patterns," Appl. Environ. Microbiol. 67:1865-1873.
Deng et al. (2010) "Laundering Durability of Superhydrophobic Cotton Fabric," Adv. Mater. 22:5473-5477.
Deng et al. (2011) "Transparent, Thermally Stable and Mechanically Robust Superhydrophobic Surfaces Made from Porous Silica Capsules," Adv. Mater. 23:2962-2965.
Deng et al. (2012) "Candle soot as a template for a transparent robust superamphiphobic coating," Science. 335:67-70.
Eibergen et al. (Oct. 13, 2015) "Potent and selective modulation of the RhlR quorum sensing receptor by using non-native ligands: An emerging target for virulence control in Pseudomonas aeruginosa," ChemBioChem. 16(16):2348-2356.
Epstein et al. (2012) "Liquid-infused structured surfaces with exceptional anti-biofouling performance," Proc. Natl. Acad. Sci. USA. 109:13182-13187.
Feng et al. (2002) "Super-Hydrophobic Surfaces: From Natural to Artificial," Adv. Mater. 14:1857-1860.
Frei et al. (2012) "2-Aminobenzimidazole derivatives strongly inhibit and disperse Pseudomonas aeruginosa biofilms," Angew. Chem. Int. Ed. 51:5226-5229.
Gao et al. (2004) "Biophysics: Water-repellent legs of water striders," Nature. 432:36.
Genzer et al. (2000) "Creating long-lived superhydrophobic polymer surfaces through mechanically assembled monolayers," Science. 290:2130-2133.
Geske et al. (2008) "Comparative analyses of N-acylated homoserine Lactones reveal unique structural features that dictate their ability to activate or inhibit quorum sensing," ChemBioChem. 9:389-400.
Geske et al. (2008) "Evaluation of a focused library of N-aryl L-homoserine lactones reveals a new set of potent quorum sensing modulators," Bioorg. Med. Chem. Lett 18:5978-5981.
Glavan et al. (Jul. 26, 2013) "Omniphobic 'RF Paper' Produced by Silanization of Paper with Fluoroalkyltrichlorosilanes," Adv. Funct. Mater. 24:60-70.
Grinthal et al. (Oct. 14, 2013) "Mobile interfaces: Liquids as a perfect structural material for multifunctional, antifouling surfaces," Chem. Mater. 26:698-708.
Heilmann et al. (1984) "Chemistry of alkenyl azlactones. I. Radiation-sensitive materials derived from azlactone-containing copolymers," J. Polym. Sci. Part A. 22(5):1179-1186.

(56) References Cited

OTHER PUBLICATIONS

Heilmann et al. (1998) "The chemistry of 2-alkenyl-5(4H)-oxazolones. VIII acid-catalyzed reaction with alcohols," Tetrahedron. 54(40):12151-12160.
Heilmann et al. (2001) "Chemistry and technology of 2-alkenyl azlactones," J. Polymer Sci. Part A. 39(21):3655-3677.
Holloway (1955) "Genetic recombination in Pseudomonas aeruginosa," J. Gen. Microbiol. 13:572-581.
Howell et al. (Feb. 4, 2015) "Stability of Surface-Immobilized Lubricant Interfaces under Flow," Chem. Mater. 27:1792-1800.
Howell et al. (Jul. 23, 2014) "Self-Replenishing Vascularized Fouling-Release Surfaces," ACS Appl. Mater. Inter. 6:13299-13307.
Huang et al. (2011) "Controllable Underwater Oil-Adhesion-Interface Films Assembled from Nonspherical Particles," Adv. Funct. Mater. 21:4436-4441.
Huang et al. (Sep. 4, 2013) "Omniphobic slippery coatings based on lubricant-infused porous polyelectrolyte multilayers," ACS Macro Lett. 2:826-829.
Ionov et al. (2012) "Self-healing superhydrophobic materials," Phys. Chem. Chem. Phys. 14:10497-10502.
Jewell et al. (2008) "Multilayered polyelectrolyte assemblies as platforms for the delivery of DNA and other nucleic acid-based therapeutics," Adv. Drug Deliver. Rev. 60:979-999.
Ji et al. (2006) "Fabrication of a Superhydrophobic Surface from the Amplified Exponential Growth of a Multilayer," Adv. Mater. 18:1441-1444.
Jin et al. (2011) "Underwater Oil Capture by a Three-Dimensional Network Architectured Organosilane Surface," Adv. Mater. 23:2861-2864.
Jisr et al. (2005) "Hydrophobic and Ultrahydrophobic Multilayer Thin Films from Perfluorinated Polyelectrolytes," Angew. Chem. Int. Ed. 44:782-785.
Johnston et al. (2007) "Assembling DNA into Advanced Materials: From Nanostructured Films to Biosensing and Delivery Systems," Adv. Mater. 19:3727-3730.
Jones et al. (2000) "Triclosan: A review of effectiveness and safety in health care settings," Am. J. Infect. Control. 28:184-196.
Jung et al. (2009) "Wetting Behavior of Water and Oil Droplets in Three-Phase Interfaces for Hydrophobicity/philicity and Oleophobicity/philicity," Langmuir. 25:14165-14173.
Kharlampieva et al. (2004) "Release of a Dye from Hydrogen-Bonded and Electrostatically Assembled Polymer Films Triggered by Adsorption of a Polyelectrolyte," Langmuir. 20:9677-9685.
Kim et al. (2012) "Liquid-Infused Nanostructured Surfaces with Extreme Anti-Ice and Anti-Frost Performance," ACS Nano. 6:6569-6577.
Kim et al. (2013) "Hierarchical or Not? Effect of the Length Scale and Hierarchy of the Surface Roughness on Omniphobicity of Lubricant-Infused Substrates," Nano Lett. 13:1793-1799.
Kim et al. (2008) "Hydrogen-Bonding Layer-by-Layer-Assembled Biodegradable Polymeric Micelles as Drug Delivery Vehicles from Surfaces," ACS Nano. 2:386-392.
Kojic et al. (2004) "Candida infections of medical devices," Clin. Microbiol. Rev. 17:255-267.
Kool et al. (Nov. 12, 2013) "Fast Hydrazone Reactants: Electronic and Acid/Base Effects Strongly Influence Rate at Biological pH," Journal of the American Chemical Society. 135(47):17663-17666.
Kota et al. (2012) "Hygro-responsive membranes for effective oil-water separation," Nat. Commun. 3:1025.
Kratochvil et al. (Aug. 26, 2015) "Nanoporous superhydrophobic coatings that promote the extended release of water-labile quorum sensing inhibitors and enable long-term modulation of quorum sensing in *Staphylococcus aureus*," ACS Biomater. Sci. Eng. 1:1039-1049.
Leslie et al. (Oct. 12, 2014) "A bioinspired omniphobic surface coating on medical devices prevents thrombosis and biofouling," Nat. Biotechnol. 32:1134-1140.
Levkin et al. (2009) "Porous Polymer Coatings: a Versatile Approach to Superhydrophobic Surfaces," Adv. Funct. Mater. 19:1993-1998.
Li et al. (2010) "Bioinspired self-healing superhydrophobic coatings," Angew. Chem. Int. Ed. 49:6129-6133.
Li et al. (2012) "Printable Superhydrophilic-Superhydrophobic Micropatterns Based on Supported Lipid Layers," Langmuir. 28:8286-8291.
Li et al. (Dec. 18, 2014) "Reactive superhydrophobic surface and its photoinduced disulfide-ene and thiol-ene (bio)functionalization," Nano Lett. 15:675-681.
Li et al. (Jul. 5, 2013) "Hydrophobic liquid-infused porous polymer surfaces for antibacterial applications," ACS Appl. Mater. Interfaces 5:6704-6711.
Lin et al. (2010) "Bio-inspired hierarchical macromolecule-nanoclay hydrogels for robust underwater superoleophobicity," Adv. Mater. 22:4826-4830.
Lin et al. (2011) "Endotoxin-induced structural transformations in liquid crystalline droplets," Science. 332:1297-1300.
Lipinski (2000) "Drug-like properties and the causes of poor solubility and poor permeability," Journal of Pharmacological and Toxicological Methods. 44:235-249.
Liu et al. (2008) "Ultrathin Multilayered Films that Promote the Release of Two DNA Constructs with Separate and Distinct Release Profiles," Adv. Mater. 20:4148-4153.
Liu et al. (2009) "Bioinspired Design of a Superoleophobic and Low Adhesive Water/Solid Interface," Adv. Mater. 21:665-669.
Liu et al. (2010) "Recent developments in bio-inspired special wettability," Chem. Soc. Rev. 39:3240-3255.
Liu et al. (2012) "Bioinspired oil strider floating at the oil/water interface supported by huge superoleophobic force," ACS Nano. 6:5614-5620.
Liu et al. (2012) "Bio-Inspired Self-Cleaning Surfaces," Ann. Rev. Mater. Res. 42:231-263.
Liu et al. (2012) "Clam's shell inspired high-energy inorganic coatings with underwater low adhesive superoleophobicity," Adv. Mater. 24:3401-3405.
Liu et al. (2012) "Complementary effects of nanosilver and superhydrophobic coatings on the prevention of marine bacterial adhesion," ACS Appl. Mater. Interfaces. 4:4683-4690.
Liu et al. (Jun. 17, 2013) "Organogel-based thin films for self-cleaning on various surfaces," Adv. Mater. 25:4477-4481.
Lynn (2007) "Peeling Back the Layers: Controlled Erosion and Triggered Disassembly of Multilayered Polyelectrolyte Thin Films," Adv. Mater. 19:4118-4130.
Ma et al. (Feb. 11, 2014) "Substrate-Independent Underwater Superoleophobic Surfaces Inspired by Fish-Skin and Mussel-Adhesives," Adv. Mater. Interfaces. 1:1300092.
MacDonald et al. (2008) "Release of a model protein from biodegradable self assembled films for surface delivery applications," J. Control. Release. 131:228-234.
Manna et al. (2008) "Encapsulation of Uncharged Water-Insoluble Organic Substance in Polymeric Membrane Capsules via Layer-by-Layer Approach," J. Phys. Chem. B. 112:13258-13262.
Manna et al. (2012) "Chemical Patterning and Physical Refinement of Reactive Superhydrophobic Surfaces," Adv. Mater. 24:4291-4295.
Manna et al. (Apr. 27, 2016) "Slippery liquid-infused porous surfaces that prevent microbial surface fouling and kill non-adherent pathogens in surrounding media: A controlled release approach," Advanced Functional Materials. 26(21):3599-3611.
Manna et al. (Apr. 8, 2015) "Fabrication of liquid-infused surfaces using reactive polymer multilayers: Principles for manipulating the behaviors and mobilities of aqueous fluids on slippery liquid interfaces," Adv. Mater. 27:3007-3012.
Manna et al. (Aug. 13, 2013) "Restoration of Superhydrophobicity in Crushed Polymer Films by Treatment with Water: Self-Healing and Recovery of Damaged Topographic Features Aided by an Unlikely Source," Adv. Mater. 25:5104-5108.
Manna et al. (Aug. 25, 2013) "Superhydrophobic polymer multilayers that promote the extended, long-term release of embedded water-soluble agents," Adv. Mater. 25:6405-6409.
Manna et al. (Feb. 4, 2015) "Synthetic Surfaces with Robust and Tunable Underwater Superoleophobicity," Adv. Funct. Mater. 25:1672-1681.

(56) References Cited

OTHER PUBLICATIONS

Mattmann et al. (2011) "Potent and selective synthetic modulators of a quorum sensing repressor in Pseudomonas aeruginosa identified from second-generation libraries of N-acylated L-homoserine lactones," ChemBioChem. 12:942-949.
Mavor et al. (2005) "Systemic fungal infections caused by *Candida* species: epidemiology, infection process and virulence attributes," Curr. Drug Targ. 6:863-874.
Mellbye et al. (Dec. 27, 2013) "Physiological framework for the regulation of quorum sensing-dependent public goods in Pseudomonas aeruginosa," J. Bacteriol. 196:1155-1164.
Moore et al. (Oct. 22, 2015) "A comparative analysis of synthetic quorum sensing modulators in Pseudomonas aeruginosa: New insights into mechanism, active efflux susceptibility, phenotypic response, and next-generation ligand design," J. Am. Chem. Soc. 137:14626-14639.
Muh et al. (2006) "Novel Pseudomonas aeruginosa quorum-sensing inhibitors identified in an ultra-high-throughput screen," Antimicrob. Agents Chemother. 50:3674-3679.
Ng et al. (2009) "Bacterial quorum-sensing network architectures," Annu. Rev. Genet. 43:197-222.
Nicolle (2005) "Catheter-related urinary tract infection," Drug. Aging. 22:627-639.
Nishimoto et al. (Oct. 23, 2013) "Bioinspired self-cleaning surfaces with superhydrophobicity, superoleophobicity, and superhydrophilicity," RSC Adv. 3:671-690.
O'Loughlin et al. (Oct. 29, 2013) "A quorum-sensing inhibitor blocks Pseudomonas aeruginosa virulence and biofilm formation," Proc. Natl. Acad. Sci. USA. 110:17981-17986.
O'Reilly et al. (Nov. 2, 2015) "Structure-Based Design and Biological Evaluation of Triphenyl Scaffold-Based Hybrid Compounds as Hydrolytically Stable Modulators of a LuxR-Type Quorum Sensing Receptor," ACS Infect. Dis. 2:32-38.
Orner et al. (2004) "Arrays for the Combinatorial Exploration of Cell Adhesion," J. Am. Chem. Soc. 126:10808-10809.
Parker et al. (2001) "Water capture by a desert beetle," Nature. 414:33-34.
Passerini et al. (1992) "Biofilms on indwelling vascular catheters," Crit. Care Med. 20:665-673.
Peeters et al. (2008) "Comparison of multiple methods for quantification of microbial biofilms grown in microtiter plates," J. Microbiol. Meth. 72:157-165.
Pereira et al. (May 20, 2014) "Brønsted acid catalyzed azlactone ring opening by nucleophiles," Tetrahedron. 70(20):3271-3275.
Ramage et al. (2005) "Candida biofilms: an update," Eukaryot. Cell. 4:633-638.
Ramage et al. (2009) "Our current understanding of fungal biofilms," Crit. Rev. Microbiol. 35:340-355.
Rasmussen et al. (1984) "Chemistry of alkenylazlactones, 2 Reaction with thiols," Makromol. Chem. Rapid Commun. 5(2):67-70.
Schmitt et al. (Feb. 15, 2016) "Peptide Conjugation to a Polymer Coating via Native Chemical Ligation of Azlactones for Cell Culture," Biomacromolecules. 17(3):1040-1047.
Schmitt et al. (May 20, 2015) "Polyethylene Glycol Coatings on Plastic Substrates for Chemically Defined Stem Cell Culture," Adv. Healthcare Mater. 4(10):1555-1564.
Seon et al. (Nov. 18, 2015) "Polyelectrolyte Multilayers: A Versatile Tool for Preparing Antimicrobial Coatings," Langmuir. 31:12856-12872.
Shen et al. (2012) "Asymmetric free-standing film with multifunctional anti-bacterial and self-cleaning properties," ACS Appl. Mater. Interfaces. 4:4476-4483.
Smith et al. (2009) "Layer-by-layer platform technology for small-molecule delivery," Angew. Chem. Int. Ed. 48:8974-8977.
Smith et al. (Dec. 17, 2012) "Droplet mobility on lubricant-impregnated surfaces," Soft Matter. 9:1772-1780.
Soike et al. (2010) "Engineering a Material Surface for Drug Delivery and Imaging using Layer-by-Layer Assembly of Functionalized Nanoparticles," Adv. Mater. 22:1392-1397.
Stacy et al. (2012) "Attenuation of quorum sensing in the pathogen Acinetobacter baumannii using non-native N-acyl homoserine lactones," ACS Chem. Biol. 7:1719-1728.
Starkey et al. (Aug. 21, 2014) "Identification of Anti-virulence Compounds That Disrupt Quorum-Sensing Regulated Acute and Persistent Pathogenicity," PLoS Pathog. 10(8):e1004321. pp. 1-17.
Subramanyam et al. (Sep. 26, 2013) "Ice Adhesion on Lubricant-Impregnated Textured Surfaces," Langmuir. 29:13414-13418.
Sun et al. (2010) "Release of DNA from polyelectrolyte multilayers fabricated using 'charge-shifting' cationic polymers: Tunable temporal control and sequential, multi-agent release," J. Control. Release. 148:91-100.
Sunny et al. (Sep. 1, 2014) "Lubricant-infused nanoparticulate coatings assembled by layer-by-layer deposition," Adv. Funct. Mater. 24:6658-6667.
Taff et al. (2012) "Comparative analysis of Candida biofilm quantitation assays," Med. Mycology. 50:214-218.
Tian et al. (Jul. 8, 2014) "Interfacial Material System Exhibiting Superwettability," Adv. Mater. 26:6872-6897.
Timonen et al. (Jul. 19, 2013) "Switchable Static and Dynamic Self-Assembly of Magnetic Droplets on Superhydrophobic Surfaces," Science. 341:253-257.
Tuteja et al. (2007) "Designing superoleophobic surfaces," Science. 318:1618-1622.
Ueda et al. (Jan. 23, 2013) "Emerging applications of superhydrophilic-superhydrophobic micropatterns," Adv. Mater. 25:1234-1247.
Ueda et al. (May 28, 2013) "Micropatterning hydrophobic liquid on a porous polymer surface for long-term selective cell-repellency," Adv. Healthcare Mater. 2(11):1425-1429.
Verho et al. (2011) "Mechanically Durable Superhydrophobic Surfaces," Adv. Mater. 23:673-678.
Vogel et al. (Jul. 31, 2013) "Transparency and damage tolerance of patternable omniphobic lubricated surfaces based on inverse colloidal monolayers," Nat. Commun. 4:2176.
Wei et al. (Sep. 18, 2014) "Supramolecular polymers as surface coatings: Rapid fabrication of healable superhydrophobic and slippery surfaces," Adv. Mater. 26:7358-7364.
Welsh et al. (Feb. 18, 2016) "Chemical genetics reveals environment-specific roles for quorum sensing circuits in Pseudomonas aeruginosa," Cell Chem. Biol. 23:361-369.
Welsh et al. (Jan. 9, 2015) "Small molecule disruption of quorum sensing cross-regulation in Pseudomonas aeruginosa causes major and unexpected alterations to virulence phenotypes," J. Am. Chem. Soc. 137:1510-1519.
Wenzel (1936) "Resistance of Solid Surfaces to Wetting by Water," Ind. Eng. Chem. 28:988-994.
Wong et al. (2011) "Bioinspired self-repairing slippery surfaces with pressure-stable omniphobicity," Nature. 477:443-447.
Xiao et al. (Sep. 25, 2013) "Slippery liquid-infused porous surfaces showing marine antibiofouling properties," ACS Appl. Mater. Interfaces. 5:10074-10080.
Xin et al. (2012) "Schiff's base as a stimuli-responsive linker in polymer chemistry," Polymer Chemistry. 3(11):3045-3055.
Xu et al. (May 17, 2013) "Nacre-Inspired Design of Mechanical Stable Coating with Underwater Superoleophobicity," ACS Nano. 7:5077-5083.
Xu et al. (Nov. 7, 2012) "An Ion-Induced Low-Oil-Adhesion Organic/Inorganic Hybrid Film for Stable Superoleophobicity in Seawater," Adv. Mater. 25:606-611.
Yao et al. (2011) "Applications of Bio-Inspired Special Wettable Surfaces," Adv. Mater. 23:719-734.
Yao et al. (Apr. 7, 2013) "Adaptive fluid-infused porous films with tunable transparency and wettability," Nat. Mater. 12:529-534.
Yao et al. (Dec. 17, 2013) "Temperature-Driven Switching of Water Adhesion on Organogel Surface," Adv. Mater. 26:1895-1900.
Yohe et al. (2012) "3D superhydrophobic electrospun meshes as reinforcement materials for sustained local drug delivery against colorectal cancer cells," J. Control. Release. 162:92-101.
Yohe et al. (2012) "Superhydrophobic Materials for Tunable Drug Release: Using Displacement of Air to Control Delivery Rates," J. Am. Chem. Soc. 134:2016-2019.
Yohe et al. (2013) "A Mechanistic Study of Wetting Superhydrophobic Porous 3D Meshes," Adv. Funct. Mater. 23:3628-3637.

(56) References Cited

OTHER PUBLICATIONS

You et al. (Sep. 4, 2014) "Fabrication of a Micro-omnifluidic Device by Omniphilic/Omniphobic Patterning on Nanostructured Surfaces," ACS Nano. 8:9016-9024.

Yuan et al. (2008) "Superwetting nanowire membranes for selective absorption," Nat. Nanotechnol. 3:332-336.

Zelikin (2010) "Drug Releasing Polymer Thin Films: New Era of Surface-Mediated Drug Delivery," ACS Nano. 4:2494-2509.

Zhai et al. (2004) "Stable Superhydrophobic Coatings from Polyelectrolyte Multilayers," Nano Lett. 4:1349-1353.

Zhai et al. (2006) "Patterned Superhydrophobic Surfaces: Toward a Synthetic Mimic of the Namib Desert Beetle," Nano Lett. 6:1213-1217.

Zhang et al. (Feb. 18, 2013) "Superhydrophobic and Superoleophilic PVDF Membranes for Effective Separation of Water-in-Oil Emulsions with High Flux," Adv. Mater. 25:2071-2076.

Zhang et al. (Oct. 2, 2013) "Nepenthes Pitcher Inspired Anti-Wetting Silicone Nanofilaments Coatings: Preparation, Unique Anti-Wetting and Self-Cleaning Behaviors," Adv. Funct. Mater. 24:1074-1080.

U.S. Appl. No. 15/192,364, filed Jun. 24, 2016, 2017/0022372, Jan. 26, 2017.

U.S. Appl. No. 15/192,425, filed Jun. 24, 2016, 2017/0022371, Jan. 26, 2017.

\* cited by examiner

E22

V-06-018

C14

DMABI

# SLIPPERY LIQUID-INFUSED POROUS SURFACES THAT PREVENT MICROBIAL SURFACE FOULING

CROSS-REFERENCE TO RELATED APPLICATIONS

This application claims priority from U.S. Provisional Patent Application No. 62/314,282, filed Mar. 28, 2016, which is incorporated by reference herein to the extent that there is no inconsistency with the present disclosure.

STATEMENT REGARDING FEDERALLY SPONSORED RESEARCH OR DEVELOPMENT

This invention was made with government support under N00014-07-1-0255 and N00014-14-1-0791 awarded by the US Navy/ONR; DMR1121288 DMR0832760 awarded by the National Science Foundation; and AI092225 awarded by the National Institutes of Health. The government has certain rights in the invention.

BACKGROUND OF THE INVENTION

Synthetic surfaces that are resistant to fouling by aqueous media, organic fluids, or biological organisms are critical in a broad range of industrial, commercial, and biomedical contexts. Surfaces that are superhydrophobic, superoleophobic, or superomniphobic, for example, form a basis for the design of self-cleaning and antifogging materials, anti-corrosive interfaces, and stain-resistant textiles, and have enabled new strategies for the transport and manipulation of complex fluids, including approaches to oil recovery and oil/water separation (see Liu et al., Chem. Soc. Rev. 2010, 39, 3240; Banerjee et al., Adv. Mater. 2011, 23, 690; Yao et al., Adv. Mater. 2011, 23, 719; Liu et al., Ann. Rev. Mater. Res. 2012, 42, 231; Campoccia et al., Biomaterials 2013, 34, 8533; Ueda et al., Adv. Mater. 2013, 25, 1234; Bellanger et al., Chem. Rev. 2014, 114, 2694; Genzer et al., Science 2000, 290, 2130; Tuteja et al., Science 2007, 318, 1618; Chu et al., Chem. Soc. Rev. 2014, 43, 2784; and Deng et al., Science 2012, 335, 67).

Slippery liquid-infused porous surfaces (SLIPS) are an emerging class of synthetic materials that exhibit unique and robust antifouling behavior. These materials are fabricated by infusion of viscous oils into porous surfaces, yielding interfaces that allow other fluids to slide off with sliding angles sometimes as low as 2°. This slippery behavior arises from an ability to host and maintain thin films of oil at their surfaces, placing a premium on chemical compatibility between the matrix and the oil and revealing design criteria that can be exploited to manipulate the behaviors of contacting fluids (e.g., to tune sliding angles and velocities or create responsive surfaces that allow control over these and other interfacial behaviors). Surfaces and coatings that exhibit these characteristics have enabled the design of new anti-icing surfaces, slippery containers for the dispensing of commercial liquids and gels, and new liquid-infused interfaces that are resistant to biofouling in complex aqueous, biological, and marine environments.

Recent reports on alternative approaches to the development of SLIPS have enabled the design of new classes of synthetic and highly 'slippery' anti-fouling materials that address practical limitations exhibited by conventional non-wetting (e.g., superhydrophobic) surfaces, and introduce new principles for the design of robust, injury-tolerant, and mechanically compliant synthetic anti-fouling surfaces (see Wong et al., Nature 2011, 477, 443; Grinthal et al., Chem. Mater. 2014, 26, 698; Epstein et al., Proc. Natl. Acad. Sci. U.S.A. 2012, 109, 13182; Yao et al., Nat. Mater. 2013, 12, 529; Liu et al., Adv. Mater. 2013, 25, 4477; Smith et al., Soft Matter 2013, 9, 1772; Vogel et al., Nat. Commun. 2013, 4; Huang et al., ACS Macro Lett. 2013, 2, 826; Leslie et al., Nat. Biotechnol. 2014, 32, 1134; Glavan et al., Adv. Funct. Mater. 2014, 24, 60; Wei et al., Adv. Mater. 2014, 26, 7358; Yao et al., Adv. Mater. 2014, 26, 1895; and Zhang et al., Adv. Funct. Mater. 2014, 24, 1074.)

Reports by Aizenberg, Levkin, and others demonstrate that SLIPS can be designed to resist fouling by bacteria and other marine organisms that can colonize and form biofilms on biomedical devices or commercial and industrial equipment (see Epstein et al., Proc. Natl. Acad. Sci. U.S.A. 2012, 109, 13182; Leslie et al., Nat. Biotechnol. 2014, 32, 1134; Howell et al., ACS Appl. Mater. Inter. 2014, 6, 13299; Li et al., ACS Appl. Mater. Inter. 2013, 5, 6704; and Xiao et al., ACS Appl. Mater. Inter. 2013, 5, 10074). Those studies suggest that appropriately designed liquid-infused surfaces can resist the attachment, colonization, and organization of communities of these organisms in ways that exceed those exhibited by some conventional anti-fouling surfaces (such as surfaces modified with polyethylene glycol and non-wetting superhydrophobic surfaces, etc.), even in complex media with proteins, surfactants, or at high ionic strengths typical of environmental conditions encountered in many applied and biologically relevant contexts.

While these past studies represent outstanding progress toward the design of new anti-fouling materials with superior functional properties, existing SLIPS do not completely inhibit colonization, and fundamental questions remain regarding both the long-term stabilities of these materials and the ability of bacteria or other microorganisms to adapt to or breach the infused liquid barriers that confer slippery character to establish 'beachheads' on underlying surfaces that could enable colonization and bio-fouling. In addition, and of particular interest in the context of potential biomedical applications of these new materials, SLIPS can currently do little to influence the behaviors of planktonic microorganisms—that is, while SLIPS can substantially prevent the adhesion of pathogenic microorganisms or the formation of microbial biofilms on treated surfaces, they cannot prevent the growth or proliferation of those organisms in solution, prevent them from colonizing other nearby surfaces, or stop them from engaging in other behaviors (e.g., toxin production) that could lead to infection and other associated burdens.

The present invention addresses these issues and allows for the functional properties and potential applications of SLIPS to be significantly expanded by adopting design strategies that leverage the potential of the porous matrices and the infused and lubricating oils in these materials as depots for the storage and subsequent release of bioactive agents. In particular, small-molecule anti-microbial agents can be stored in the porous matrices or dissolved and stored in a fugitive oil phase without compromising the 'slippery' characteristic of the material, thereby providing new approaches to the design of multi-functional or dual-action SLIPS with improved antimicrobial properties. Provided that the embedded agent can also diffuse into the oil phase and/or from the oil phase into surrounding aqueous media, this approach also offers opportunities to design anti-fouling SLIPS that could kill or influence the behaviors of planktonic microorganisms. In a broader and more general context, the ability to store and control the release of small molecules or other agents from SLIPS allows for a wide range of other new applications for these liquid-infused materials.

SUMMARY OF THE INVENTION

Conventional oil-infused 'slippery' surfaces can prevent surface fouling owing to their slippery character, which reduces the ability of bacteria or other substances from adhering to the surface, but cannot otherwise influence events that occur in that surrounding media or change the properties of that surrounding media. The present invention relates to methods for the design of multifunctional slippery surfaces that enable these surfaces to exert influences and affect new and desired behaviors in surrounding environments. The present invention is generally directed toward the design of antifungal and antibacterial polymer-based SLIPS that inhibit microbial adhesion and/or promote the sustained release of small-molecule compounds, such as a broad-spectrum antimicrobial agent, an antifungal agent, an antibacterial agent, an agent that modulates bacterial or fungal quorum sensing, an agent that attenuates virulence, or combinations thereof.

In an embodiment, the present invention provides polymer-based slippery liquid-infused porous surfaces (SLIPS) that can prevent adhesion and colonization by fungal and bacterial pathogens and also kill and/or attenuate the colonization and virulence of non-adherent pathogens in surrounding media. The present approach exploits the polymer and liquid oil phases in these slippery materials to sustain the release of small-molecule compounds, such as antimicrobial agents, antifungal agents, virulence attenuating agents, and bacterial or fungal quorum sensing agents. This controlled release approach improves the inherent anti-fouling properties of SLIPS, has the potential to be general in scope, and expands the potential utility of slippery, non-fouling surfaces in both fundamental and applied contexts.

One embodiment of the present invention provides a slippery liquid-infused porous surface (SLIPS) that controllably releases a molecule, wherein the slippery oil-infused surface comprises: a) a porous matrix having nanoscale or microscale porosity; b) an oil covering at least a portion of the porous matrix, wherein the oil at least partially fills the pores of the porous matrix; and c) one or more small-molecule compounds able to reduce, inhibit, or modulate the behaviors of non-adherent pathogens in surrounding media, wherein the one or more small-molecule compounds are located on the surface or within said porous matrix, within said oil, or both, and wherein the slippery oil-infused surface is able to controllably release the one or more small-molecule compounds when the slippery oil-infused surface is immersed into said media. In an embodiment, the porous matrix has nanoscale porosity.

As used herein, "small-molecule compounds" refer to compounds having a molecular weight of approximately 900 daltons or less, preferably approximately 700 daltons or less, preferably approximately 500 daltons or less, or preferably approximately 300 daltons or less. It is understood that the chemical structure of the molecule will influence its solubility in the oil phase, its solubility in the water phase, and its interactions with the polymer matrix in ways that will influence, and which can be used to modulate, its release profile into the surrounding media. In an embodiment, the small-molecule compound is soluble to very soluble in water (at least 3.3 g/100 g $H_2O$). In an embodiment, the small-molecule compound is sparingly soluble in water (0.1 to 3.3 g/100 g $H_2O$). In an embodiment, the small-molecule compound is slightly soluble in water (0.01 to 0.1 g/100 g $H_2O$). In an embodiment, the small-molecule compound is practically insoluble (less than 0.01 g/100 g $H_2O$). In an embodiment, the small-molecule compound is not a polypeptide. In an embodiment, the small-molecule compounds have drug-like characteristics such as good absorption, distribution, metabolism, excretion and toxicity (ADMET) profiles as known in the art (see, for example, Lipinski, Journal of Pharmacological and Toxicological Methods 2000, 44: 235-249).

As used throughout this invention, preferably the one or more small-molecule compounds are able to reduce, inhibit, or modulate the behaviors of non-adherent pathogens in the surrounding media. As non-limiting examples, the one or more small-molecule compounds can kill or otherwise reduce at least a number of the pathogens, slow reproduction or growth of least a portion of pathogens, or modulate behavior such as preventing or reducing the ability of pathogens to communicate with each other. In an embodiment, the one or more small-molecule compounds comprise an antimicrobial agent, an antifungal agent, an antibacterial agent, an agent that modulates bacterial or fungal quorum sensing, an agent that attenuates virulence, or a combination thereof. In an embodiment, the one or more small-molecule compounds is a natural or synthetic antibiotic agent, natural or synthetic antifungal agent, quorum sensing modulator, or a combination thereof. In an embodiment, the one or more small-molecule compounds comprise one or more antimicrobial peptides having a molecular weight of 900 daltons or less. In another embodiment, the one or more small-molecule compounds do not include any peptides. Optionally, the one or more small-molecule compounds is hydrophobic.

Preferably, the one or more small-molecule compounds are able to reduce, inhibit, or modulate fungal and bacterial pathogens including, but not limited to, *Candida* species, *Aspergillus* species, *Cryptococcus* species, *Histoplasma* species, *Helicobacter* species, *Neisseria* species, *Pneumocystis* species, *Stachybotrys* species, *Pseudomonas* species, *Escherichia* species, *Streptococcus* species *and Staphylococcus* species.

In further embodiments, the one or more small-molecule compounds is selected from the group consisting of acyl L-homoserine lactone (AHL) derivatives, aminobenzimidazole (ABI) derivatives, and combinations thereof. Classes of useful small-molecule drugs are modulators and particularly antagonists of bacterial quorum sensing. A number of such small-molecule modulators are known in the art and several exemplary quorum sensing modulators are illustrated below. Eibergen et al., ChemBioChem 2015, 16:2348-2356, reports among others certain classes of quorum sensing antagonists designated PHL's and POHL's therein as exemplified by compounds A and B shown below. Moore et al., J. Amer. Chem. Soc. 2015, 137:14626-14639 reports among others AHL mimics which are quorum sensing antagonists such as compound C and certain non-AHL modulators such as compound D (shown below). O'Reilly et al., ACS Infect. Dis. 2016, 2:32-38, for example, reports among others hydrolytically stable LasR antagonists such as compounds E and F (shown below). Starkey et al., PLoS Pathog. 2014, 10, e100432, 1 report compounds which disrupt quorum sensing such as compound G (shown below). Frei et al., Angewandte Chemie 2012, 124:5316-5319 report 2-aminobenzimidazoles, such as compound H (shown below), which inhibit and disperse biofilms. Each of these references is incorporated by reference herein in its entirety for descriptions of quorum sensing modulators, particularly antagonists of quorum sensing, including descriptions of their preparation and their activities. U.S. Pat. Nos. 8,815,943; 8,624,063; 8,367,680; 8,269,024; 7,910,622; and 7,642,285 relate to small molecule quorum sensing modulators useful in the methods of the present invention.

In further embodiments, the one or more small-molecule compounds is selected from the group consisting of:

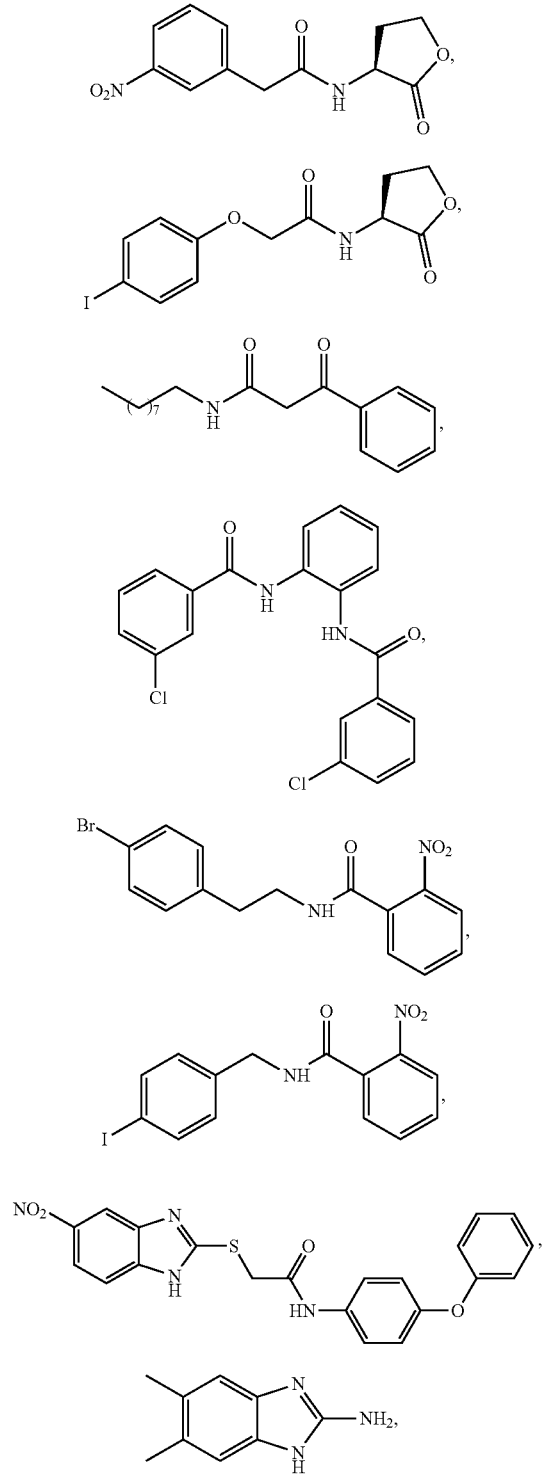

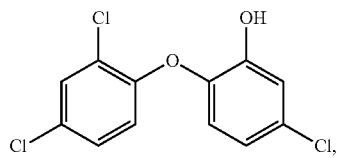

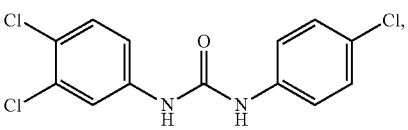

or combinations thereof.

One embodiment of the invention is based on SLIPS fabricated by the infusion of a hydrophobic liquid oil into nanoporous polymer multilayers fabricated by reactive/co-valent layer-by-layer assembly, such as described in Manna et al., Adv. Mater. 2015, 27, 3007; Buck et al., Adv. Mater. 2007, 19, 3951; Buck et al., Polym. Chem. 2012, 3, 66; and Manna et al., Adv. Funct. Mater. 2015, 25, 1672. The present invention further demonstrates that (i) these polymer-based SLIPS can substantially prevent surface fouling, including biofilm formation, by several types of common fungal and bacterial human pathogens, and (ii) that biofilm formation on the SLIPS-coated surfaces of planar objects and polymer-based catheter tubes can be reduced further by using porous polymer matrices loaded with one or more antifungal or antibacterial agents, such as triclosan, a model broad-spectrum antimicrobial agent.

The present invention also demonstrates that the release of an antimicrobial agent into the surrounding media can be used to efficiently and effectively kill planktonic microorganisms present in surrounding media and thereby prevent biofilm formation on neighboring uncoated surfaces. Without being bound by theory, it is believed the SLIPS of the present invention sustain the release of the one or more small-molecule compounds by the partitioning of the one or more small-molecule compounds from the porous polymer matrix into the liquid oil phase and from the liquid oil phase into the surrounding aqueous media. The experimental results presented introduce new principles that could prove useful for the design of multi-functional slippery surfaces with improved anti-fouling properties. However, it should be noted that the one or more small-molecule compounds can be loaded into the oil itself, and thus the controlled release is determined by the partitioning of the small-molecule compound from the oil into the surrounding aqueous media. Alternatively, the small-molecule compounds may travel along pathways or channels formed at the interphase of the oil infused porous matrix and other regions.

In an embodiment, the surrounding media is an aqueous media where the surface may encounter fungi, bacteria, and/or other microorganisms. Types of surrounding media include, but are not limited to, salt water environments (such as sea water or saline solutions), fresh water environments (such as swamp water or fresh lake water), and physiological or physiologically relevant media (including but not limited to phosphate-buffered saline solutions, TRIS-buffered saline solutions, HEPES-buffered saline solutions, Ringer's solution, cell culture media as known in the art, blood or blood plasma, and other bodily fluids). Preferably, the surrounding media does not promote the leaching of the oil or degrade the oil phase of the SLIPS, or does so at a slow rate.

In an embodiment, the present invention provides a multilayer film comprising one or more bilayers infused with an oil, wherein each bilayer comprises an optionally functionalized first polymer layer in contact with a second polymer layer, and wherein the multilayer film has a nanoscale or microscale porosity. Preferably, the multilayer film has nanoscale porosity. The infusion of the oil into at least a portion of the rough or porous surfaces of the multilayer film causes other liquids placed in contact with the multilayer film to slide off the multilayer film or a surface coated with the multilayer film. Additionally, the multilayer film comprises one or more small-molecule compounds able to be controllably released from the multilayer film into the surrounding media.

In an embodiment, the present invention provides a method for fabricating a slippery liquid-infused porous surface (SLIPS) able to reduce or inhibit non-adherent pathogens in surrounding media, the method comprising the steps of: a) forming a porous matrix on a substrate, wherein said porous matrix has nanoscale or microscale porosity; b) exposing the porous matrix to an oil, wherein said oil coats at least a portion of the porous matrix and said oil at least partially fills the pores of at least a portion of said porous matrix; and c) loading one or more small-molecule compounds onto or into said porous matrix or into said oil. Optionally, the one or more small-molecule compounds is loaded onto or into the porous matrix, or within the oil itself, prior to exposing the porous matrix to the oil. Alternatively, the one or more small-molecule compounds are loaded within the oil after exposing the porous matrix to the oil. In a further embodiment, an additional one or more small-molecule compound is loaded into the oil when levels of small-molecule compounds drop below a desired level, such as from prolonged use of the SLIPS. The newly added one or more small-molecule compounds can be the same or different than the original small-molecule compounds. Preferably, the one or more small-molecule compounds is able reduce, inhibit, or modulate the behaviors of said pathogens upon contact with said pathogens.

In another embodiment, the present invention provides a method for fabricating a slippery liquid-infused porous surface (SLIPS) multilayer film able to reduce or inhibit non-adherent pathogens in surrounding media, where the multilayer film comprises one or more bilayers, the method comprising the steps of: a) exposing a surface of a substrate to a first solution comprising a first polymer wherein a layer of the first polymer is deposited on at least a portion of the substrate; b) exposing the substrate to a second solution comprising a second polymer wherein the second polymer reacts with the first polymer layer and a layer of the second polymer is deposited on at least a portion of the first polymer layer, thereby forming a bilayer in the multilayer film; c) exposing the substrate to an oil wherein said oil coats at least a portion of the multilayer film and said oil at least partially fills the pores of at least a portion of said multilayer film; and d) loading one or more small-molecule compounds onto or into said one or more bilayers or into said oil. Preferably, the one or more small-molecule compounds is able to reduce, inhibit, or modulate the behavior of said pathogens upon contact with the pathogens.

Optionally, the one or more small-molecule compounds are loaded onto or into the one or more bilayers, or within the oil itself, prior to exposing the substrate to the oil. Alternatively, the one or more small-molecule compounds are loaded within the oil after exposing the substrate to the oil. When administered to the one or more bilayers, the one or more small-molecule compounds can be deposited on, or within, the outermost bilayer. Alternatively, the one or more small-molecule compounds can be deposited on, or within, multiple bilayers or even all of the bilayers. In a further embodiment, an additional one or more small-molecule compound is loaded into the oil when levels of small-molecule compounds drop below a desired level, such as from prolonged use of the multilayer film. The newly added one or more small-molecule compounds can be the same or different than the original small-molecule compounds.

The fabrication method relating to the multilayer film optionally comprises a rinsing step comprising exposing or washing the substrate with a rinse solvent or solution each time step a) is performed and each time step b) is performed. In an embodiment, a fresh rinse solvent or solution is employed for each rinsing step. In a further embodiment, the same rinse solution is re-used for each rinsing step.

Preferably, steps a) and b) relating to the multilayer film are repeated one or more times until the multilayer film reaches the desired thickness or desired number of layers before the substrate is exposed to the oil, where each cycle deposits a new bilayer on the substrate. In specific embodiments, the multilayer polymer film comprises more than one bilayer. In a further embodiment, steps a) and b) are repeated 2 or more times, 5 or more times, 10 or more times, 20 or more times, 30 or more times, 50 or more times, or 100 or more times. The substrate can be exposed to the solutions containing the polymer solutions using methods known in the art, including but not limited to, dip coating.

The substrate can be any material able to support the formation of the nanoporous or microporous porous matrix, including but not limited to glass, metals and plastics. The substrate can include curved and irregularly shaped three dimensional surfaces, as well as completely solid surfaces and mesh surfaces (e.g., having a porosity between 100 μm and 250 μm). For example, the substrate can be the interior of a tube or container for a liquid or gel where it is undesirable for the contents of the tube or container to stick or adhere to the surface. The porous matrix, first polymer layer, second polymer layer, and oil are therefore selected so that the liquid or gel has reduced adhesion to the container. Alternatively, the substrate can be a display of a sensor where the degree or extent to which a liquid adheres to the substrate indicates the presence of a substance in the liquid.

A further embodiment of the invention provides for patterning the substrate so that the multilayer film is formed on a first specified portion of the substrate, thereby creating a substrate having one or more "slippery" regions and one or more "sticky" regions. A portion of the multilayer film on the first specified portion of the substrate is further functionalized with an amine or hydroxyl group having the formula R—$NH_2$ or R—OH, where R is hydrophobic. In a further embodiment, a second specified portion of the substrate is not covered by the oil infused porous matrix, or, alternatively, a portion of the one or more bilayers on the second specified portion of the substrate is further functionalized with an amine or hydroxyl group having the formula R—$NH_2$ or R—OH, where R is hydrophilic.

Additionally, in a further embodiment, a portion of the one or more bilayers on the first specified portion of the substrate is further functionalized with an amine or hydroxyl group having the formula R—$NH_2$ or R—OH, where R is hydrophobic, a second specified portion of the substrate is not covered by the oil infused multilayer film, and a third portion of the substrate is covered by a bilayer where a portion of the one or more bilayers on the third specified portion of the substrate is further functionalized with an amine or hydroxyl group having the formula R—NH$_2$ or R—OH, where R is hydrophilic.

The first and second polymer layers of the bilayer can comprise any polymers or combination of polymers able to form a stable bilayer and where the first polymer layer is optionally able to be functionalized and the second polymer layer is optionally also able to be functionalized (as described in U.S. Pat. No. 8,071,210). The chemical reactivity of the functionalized bilayers provides means to tune interactions between the matrix and infused oil phases. Spatial control over the functionalization can be used to create SLIPS with regions devoid of oil that can prevent or arrest the sliding of aqueous fluids, extract samples of liquid from contacting media, or provide control over the trajectories of sliding droplets. Preferably, the first polymer layer is covalently cross-linked with the second polymer layer. In further embodiments, the bilayers are reacted with small chemical groups containing a hydrophobic or hydrophilic amine to further functionalize the bilayer (i.e., to install secondary surface functionality).

In an embodiment, the first polymer layer of the bilayer comprises a functionalized azlactone having the formula:

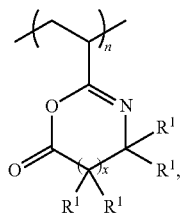

wherein x is 0 or the integers 1 or 2; and each R$^1$ is independently selected from the group consisting of: hydrogen, alkyl groups, alkenyl groups, alkynyl groups, carbocyclic groups, heterocyclic groups, aryl groups, heteroaryl groups, alkoxy groups, aldehyde groups, ether groups, and ester groups, any of which may be substituted or unsubstituted. In an embodiment, the first polymer layer comprises functionalized poly(vinyl-4,4-dimethylazlactone) (PVDMA). In an embodiment, the first polymer layer consists of functionalized poly(vinyl-4,4-dimethylazlactone) (PVDMA). In a further embodiment, the PVDMA is synthesized by free-radical polymerization of PVDMA with intentionally added cyclic azlactone-functionalized oligomer in an amount ranging from 1 wt % to 10 wt %, preferably between 5 wt % and 8 wt %.

Useful functionalized azlactone polymers include, but are not limited to, poly(vinyl-4,4-dimethylazlactone), poly(2-vinyl-4,4-dimethyl-2-oxazolin-5-one), poly(2-isopropenyl-4,4-dimethyl-2-oxazolin-5-one), poly(2-vinyl-4,4-diethyl-2-oxazolin-5-one), poly(2-vinyl-4-ethyl-4-methyl-2-oxazolin-5-one), poly(2-vinyl-4-dodecyl-4-methyl-2-oxazolin-5-one), poly(2-vinyl-4,4-pentamethylene-2-oxazolin-5-one), poly (2-vinyl-4-methyl-4-phenyl-2-oxazolin-5-one), poly(2-isopropenyl-4-benzyl-4-methyl-2-oxazolin-5-one), or poly (2-vinyl-4,4-dimethyl-1,3-oxazin-6-one). Useful azlactone functionalized polymers further include azlactone functionalized polyisoprenes and azlactone functionalized polybutadienes.

In an embodiment, the second polymer layer of the bilayer is optionally functionalized and comprises an amine functionalized polymer, an alcohol functionalized polymer, or a thiol functionalized polymer. Creating specific functionalities with amine, alcohol, and thiol groups is a process well known in the art (for example, see Bioconjugate Techniques, 2$^{nd}$ Edition, 2008, Greg T. Hermanson). In embodiments, the second polymer layer comprises an optionally functionalized polymer selected from the group consisting of poly (ethylene imine) (PEI), polylysine, pollyallylamine, poly (amidoamine) dendrimers, polyvinyl alcohol, poly hydroxyl ethyl methacrylate, poly(methacrlic acid) functionalized with cysteamine, and linear and hyperbranched and dendritic polymers functionalized with primary amines, hydroxyl groups, or thiol groups.

In embodiments, the second polymer layer comprises a polymer, which is optionally functionalized, selected from the group consisting of polyolefins, poly(alkyls), poly(alkenyls), poly(ethers), poly(esters), poly(imides), polyamides, poly(aryls), poly(heterocycles), poly(ethylene imines), poly (urethanes), poly($\alpha$,$\beta$-unsaturated carboxylic acids), poly($\alpha$, $\beta$-unsaturated carboxylic acid derivatives), poly(vinyl esters of carboxylic acids), poly(vinyl halides), poly(vinyl alkyl ethers), poly(N-vinyl compounds), poly(vinyl ketones), poly (vinyl aldehydes) and any combination thereof. In an embodiment, the second polymer layer comprises poly (ethylene imine) (PEI).

For some embodiments, it may be desirable to further functionalize a portion of the one or more bilayers. This can be achieved, for example, by reacting a portion of any residual functional groups in the one or more bilayers with an amine group or hydroxyl group, or by reacting a portion of the first or second polymer with an amine reactive group or hydroxyl reactive group.

In an embodiment, at least a portion of the residual functional groups in the bilayer is reacted with an amine or hydroxyl group having the formula R—NH$_2$ or R—OH, where R is hydrophobic or hydrophilic. In embodiments, R is a substituted or unsubstituted C$_1$ to C$_{20}$ alkyl group, preferably a C$_1$ to C$_{12}$ alkyl group. In other embodiments, R is a substituted or unsubstituted C$_2$ to C$_{20}$ alkenyl group, preferably a C$_2$ to C$_{12}$ alkenyl group. In further embodiments, at least a portion of the residual functional groups in the bilayer is reacted with an amine selected from the group consisting of methylamine, ethylamine, propylamine, butylamine, pentylamine, hexylamine, heptylamine, octylamine, nonylamine, decylamine, and combinations thereof, preferably n-propylamine, n-octylamine, or n-decylamine. In other embodiments, R is an alkyl group substituted with one or more hydroxyl groups or charged groups such as COO$^-$ or NR3$^+$. In an embodiment, at least a portion of the residual functional groups in the bilayer is reacted with an amino sugar, amino alcohol, amino polyol, glucamine (preferably D-glucamine), dimethylaminopropylamine (DMAPA), and combinations thereof.

In an embodiment, the polymer of the first polymer layer is further functionalized with a hydrophobic (decylamine or propylamine) or hydrophilic (glucamine) primary amine-containing small molecule.

As used herein, "an oil" refers to any water-immiscible phase, preferably a non-polar, hydrophobic chemical substance which is a liquid at ambient temperature and which has no or very low solubility in water. Preferably, the oil is selected so as to either completely or partially solubilize the small-molecule compounds. The oil infused into the one or more bilayers can be a synthetic oil or a natural oil, and is preferably a biocompatible oil. Preferably, the oil is selected from the group consisting of a silicone oil, a vegetable oil, a mineral oil, a perfluorinated oil, a thermotropic liquid crystal, an anisotropic oil, and combinations thereof. Suitable vegetable oils include, but are not limited to, canola oil, coconut oil, olive oil, soybean oil and combinations thereof.

In some embodiments, silicone oil is selected due to improved solubility with the one or more small-molecule compounds.

In an embodiment, a slippery liquid-infused porous surface (SLIPS) coating is provided comprising: a) a multilayer polymer film comprising one or more bilayers where said multilayer polymer film has a nanoscale or microscale porosity, wherein each bilayer comprises a first polymer layer covalently linked with a second polymer layer; b) an oil selected from the group consisting of a silicone oil, a vegetable oil, a mineral oil, a thermotropic liquid crystal, and combinations thereof, wherein said oil coats at least a portion of the multilayer polymer film and said oil at least partially fills the pores of at least a portion of said multilayer polymer film; and c) one or more small-molecule compounds able to reduce or inhibit non-adherent pathogens in surrounding media, wherein the one or more small-molecule compounds are located on the surface of the one or more bilayers, within the oil, or both, wherein the multilayer film is able to controllably release an effective amount of one or more small-molecule compounds when said multilayer film is immersed into said media. Preferably, the multilayer polymer film of the coating has a thickness of 5 µm or less, and comprises one or more PVDMA/PEI bilayers, which are further functionalized with a hydrophobic amine. Preferably, the multilayer polymer film has nanoscale porosity.

A specific embodiment of the present invention provides a SLIPS design based on the infusion of oils into nanoporous or microporous (preferably nanoporous) polymer coatings fabricated by reactive layer-by-layer assembly of polymer multilayers using branched poly(ethylene imine) (PEI) and the amine-reactive polymer poly(vinyl-4,4-dimethylazlactone) (PVDMA). In an embodiment, the multilayer film comprises one or more PVDMA/PEI bilayers, which are further functionalized with a decyl group by reacting with n-decylamine and wherein the one or more bilayers are infused with a silicone oil or an anisotropic thermotropic liquid crystal.

One aspect of the invention provides thin multilayer polymer films and coatings (e.g., equal to or less than 100 µm, equal to or less than 50 µm, preferably less than or equal to 10 µm, preferably less than or equal to 5 µm). Preferably, the multilayer film comprises 2 or more bilayers, 5 or more bilayers, 10 or more bilayers, 20 or more bilayers, 30 or more bilayers, 50 or more bilayers, or 100 or more bilayers. Preferably each first polymer layer alternates with the second polymer layer. In embodiments, the multilayer films have a nanoscale or microscale porosity. Preferably, the multilayer films have nanoscale porosity.

In an embodiment, SLIPS are infused with a thermotropic liquid crystal (an anisotropic oil) to generate sliding angles and velocities that depend critically upon the chemical compositions of contacting aqueous phases, revealing a novel 'sliding' basis for the sensing and naked-eye detection of environmental analytes, including bacterial endotoxin (i.e., LPS) in aqueous media via visually apparent changes in droplet sliding speeds as a function of analyte concentration. Such LC-infused SLIPS provide opportunities to design slippery surfaces that could permit active and external control over droplet adhesion and mobility.

In an embodiment, the present invention provides a method for reducing, inhibiting, or modulating the behaviors of non-adherent pathogens in media surrounding a substrate comprising the steps of: a) providing a slippery liquid-infused porous surface (SLIPS) on the substrate, said slippery oil-infused surface comprising:

i) a porous matrix having nanoscale or microscale porosity;

ii) an oil covering at least a portion of the porous matrix, wherein said oil at least partially fills the pores of the porous matrix; and iii) one or more small-molecule compounds able to reduce, inhibit, or modulate the behaviors said pathogens upon contact with said pathogens, wherein the one or more small-molecule compounds are located on the surface of said porous matrix, within said oil, or both; and b) controllably releasing the one or more small-molecule compounds from said slippery oil-infused surface into said media, wherein the one or more small-molecule compounds contact the pathogens thereby reducing the number of pathogens, inhibiting the growth or colonization of the pathogens, or modulating the behaviors of the pathogens.

In a further embodiment, one or more additional small-molecule compounds are loaded within the oil when the levels of small-molecule compounds drop below a desired level or when different small-molecule compounds are desired. For example, a different anti-fungal or anti-bacterial compound can be added to the SLIPS depending on which pathogens are currently present in the surrounding media. Alternatively, the small-molecule compounds can be replenished when a significant amount of the small-molecule compounds has been released into the surrounding media by the SLIPS during use. In an embodiment, the porous matrix is in fluid communication with a reservoir containing additional amounts of the oil, small-molecule compounds or both. When the amount of oil or small-molecule compounds at the surface of the SLIPS is depleted, additional amounts of the oil or small-molecule compounds can be supplied from the reservoir.

In an embodiment, the present invention provides a method for reducing, inhibiting, or modulating the behaviors of non-adherent pathogens in media surrounding a substrate comprising the steps of a) providing a multilayer film on the substrate, said multilayer film comprising:

i) one or more bilayers, wherein each bilayer comprises a first polymer layer in contact with a second polymer layer, where said multilayer polymer film has nanoscale or microscale porosity;

ii) an oil selected from the group consisting of a silicone oil, a vegetable oil, a mineral oil, a thermotropic liquid crystal, and combinations thereof, wherein said oil coats at least a portion of the multilayer polymer film and said oil at least partially fills the pores of at least a portion of said multilayer polymer film; and iii) one or more small-molecule compounds able to reduce, inhibit, or modulate the behaviors of said pathogens upon contact with said pathogens, wherein the one or more small-molecule compounds are located on the surface of said one or more bilayers, within said oil, or both; and b) controllably releasing an effective amount of the one or more small-molecule compounds from said multilayer film into said media, wherein the one or more small-molecule compounds contact the pathogens thereby reducing the number of pathogens, inhibiting the growth or colonization of the pathogens, or modulating their virulence.

Preferably, the surface comprises one or more optionally functionalized PVDMA/PEI bilayers and the oil is a silicone oil. Preferably, the one or more small-molecule compounds comprise an antimicrobial agent, an antifungal agent, an antibacterial agent, an agent that modulates bacterial or fungal quorum sensing, an agent that attenuates virulence, or a combination thereof, and the non-adherent pathogens comprise bacteria, fungi, or a combination thereof. Optionally, the one or more small-molecule compounds is a natural or synthetic antibiotic agent, natural or synthetic antifungal agent, a quorum sensing modulator or a combination thereof. In an embodiment, the one or more small-molecule compounds is an AHL derivative or ABI derivative. In an embodiment, the one or more small-molecule compounds is selected from the group consisting of:

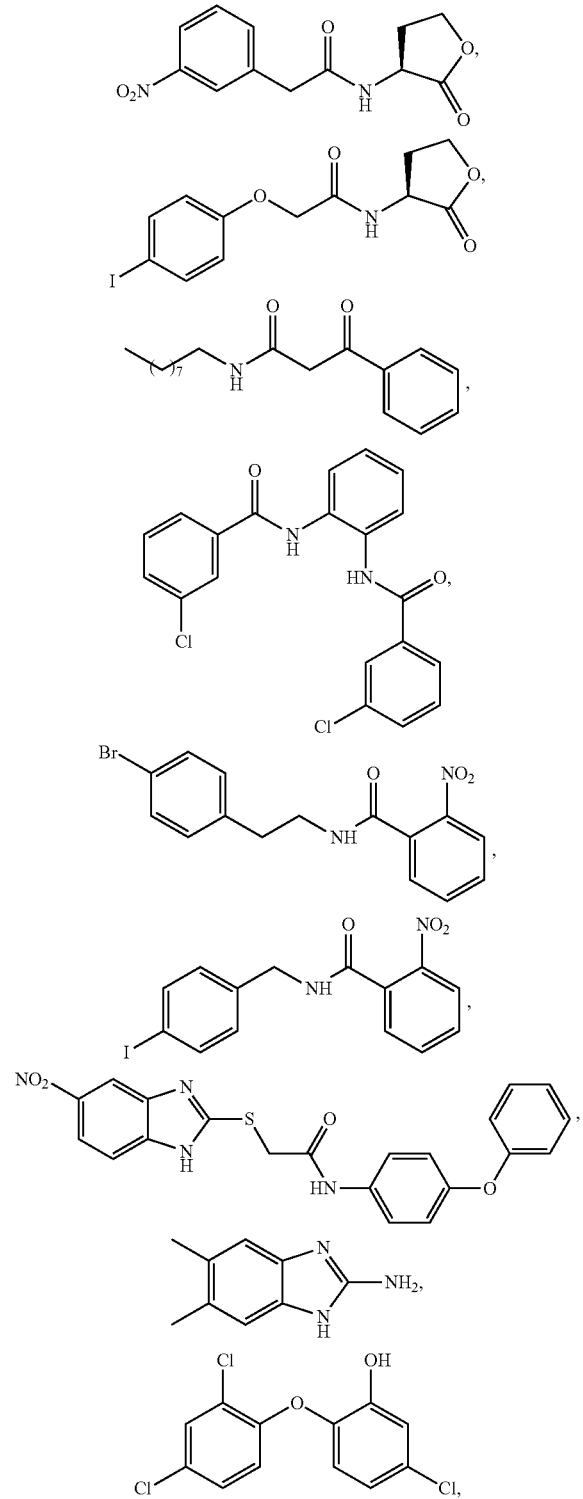

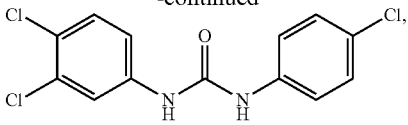

or combinations thereof.

Thus, the methods described herein can be used to fabricate physically and chemically durable SLIPS coatings on objects of arbitrary shape, size, and topology (e.g., on curved surfaces, insides of hollow tubes, etc.). Specifically these slippery surfaces could be used as antifouling surfaces, anti-bacterial/fungal surfaces where the liquid phases used to impart anti-fouling properties can also be used as reservoirs for the controlled release of other active agents (e.g., antibiotics, antimicrobial agents, or anti-biofilm agents) that can reduce or inhibit non-adherent pathogens in the surrounding media.

DETAILED DESCRIPTION OF THE INVENTION

Definitions

Figure 1:
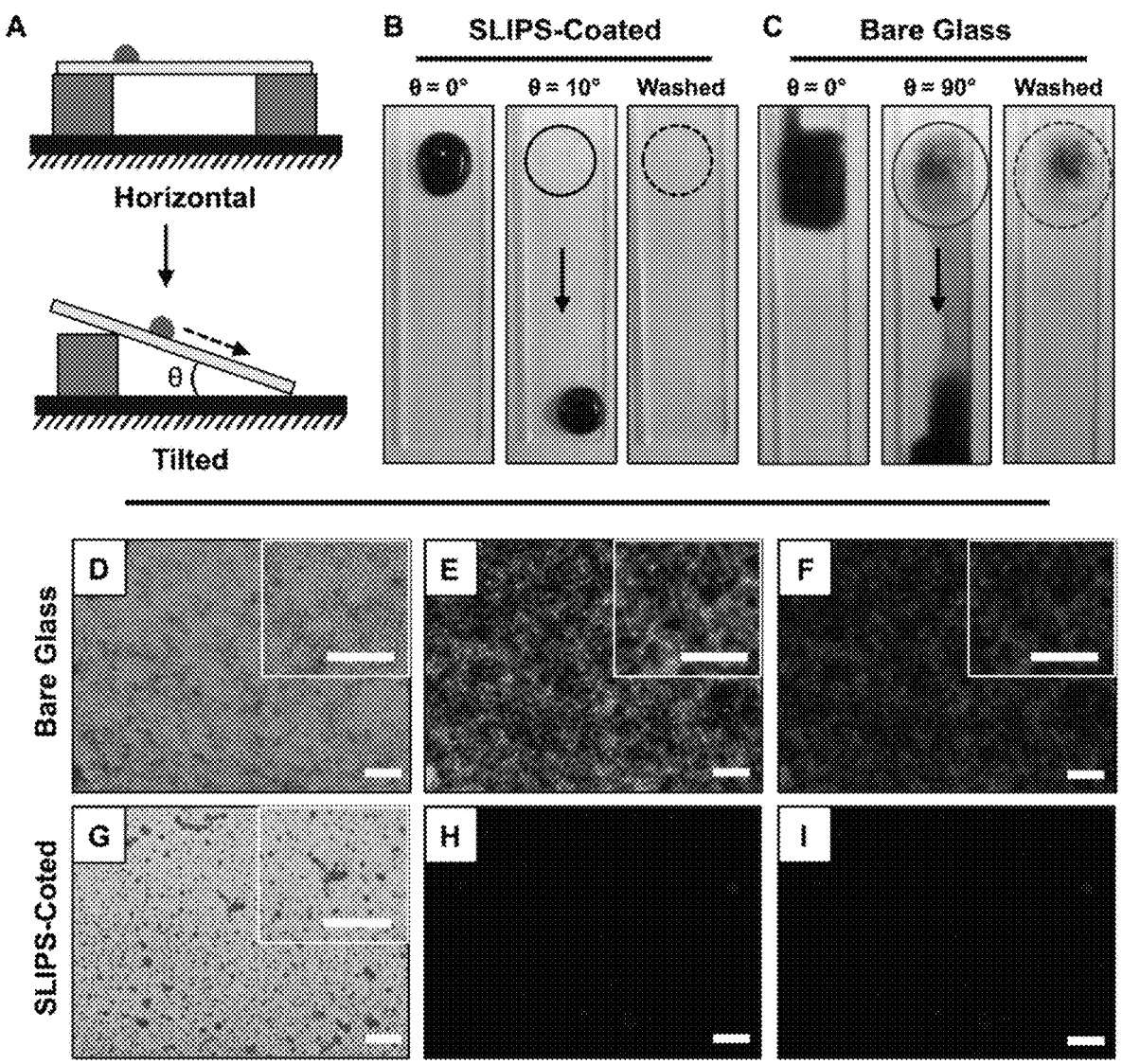
FIG. 1. (A) Schematic illustration showing a side-view depiction of the beading and sliding of an aqueous droplet on horizontally placed (top) and tilted (bottom) 'slippery' liquid-infused porous surfaces (SLIPS). (B-C) Digital pictures, acquired from a top down vantage point, of a 50 µL droplet of C. albicans inoculum incubated on the surfaces of (B) SLIPS-coated glass substrates and (C) bare glass substrates for 3 hours; droplets are shown after staining with crystal violet and either before or after tilting from horizontal (at the angles indicated) and after washing with DI water; solid and dotted circles mark the original locations of the droplets before sliding; arrows indicate direction of sliding. (D-I) Bright-field (D,G) and fluorescence (E-F, H-I) microscopy images of bare glass (D-F) and SLIPS-coated (G-I) glass substrates after incubation with droplets of C. albicans inocula; droplets were incubated for 3 hours, stained with FUN-1 dye, and tilted to permit aqueous fluids to slide away from the original location of the droplet prior to imaging; green fluorescence indicates cytoplasmic staining, red stain marks intravacuolar structures in metabolically active (live) cells. Scale bars, including insets, are 100 µm.

As used herein, the term "slippery" refers to surfaces that allow liquid droplets to slide off the surface with sliding angles of 10° or less, preferably 5° or less, 2.5° or less, or 2° or less.

As used herein, the term "controllably released" refers to a molecule, drug and/or compound which is initially contained within the porous matrix and/or oil of a slippery liquid-infused porous surface (SLIPS) and is progressively released into the surrounding media over a consistent period of time. In some embodiments, the time require to release at least 50% of the molecule, drug and/or compound into the surrounding media is 6 hours or more, preferably 24 hours or more, 4 days or more, preferably 10 days or more, 20 days or more, 30 days or more, 60 days or more, 100 days or more, 120 days or more, or 180 days or more.

As used herein, "functionalized polymer" refers to a polymer in which at least a portion of the individual monomer units are substituted with a specific functional group. For the functionalized polymers of the present invention, at least 1% or more, at least 2% or more, at least 5% or more, at least 10% or more, at least 15% or more, at least 20% or more, at least 30% or more, at least 50% or more, at least 75% or more, or at least 90% or more of the portion of the monomer units is substituted with a specific functional group.

An "amine reactive group" or "hydroxyl reactive group" can be any functional group able to react with an amine group or hydroxyl group, respectively.

As used herein, the term "anti-fouling" refers to a material's ability to resist adhesion by an undesirable material, such as oils, organic compounds, and organisms. In particular, it is desirable to prevent or reduce the adhesion of hydrophobic compounds and organisms to a material which is submerged or in contact with water.

The term "nanoscale" refers to a length less than 1,000 nm, preferably less than 100 nm, and the term "microscale" refers to a length less than 1,000 µm, preferably less than 100 µm.

The term "alkyl" refers to a monoradical of a branched or unbranched (straight-chain or linear) saturated hydrocarbon and to cycloalkyl groups having one or more rings. Alkyl groups as used herein include those having from 1 to 20 carbon atoms, preferably having from 1 to 12 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-20 carbon atoms. Cycoalkyl groups include those having one or more rings. Cyclic alkyl groups include those having a 3-, 4-, 5-, 6-, 7-, 8-, 9-, 10-, 11- or 12-member carbon ring and particularly those having a 3-, 4-, 5-, 6-, or 7-member ring. The carbon rings in cyclic alkyl groups can also carry alkyl groups. Cyclic alkyl groups can include bicyclic and tricyclic alkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group linked to oxygen and can be represented by the formula R—O. Examples of alkoxy groups include, but are not limited to, methoxy, ethoxy, propoxy, butoxy and heptoxy. Alkoxy groups include substituted alkoxy groups wherein the alky portion of the groups is substituted as provided herein in connection with the description of alkyl groups.

The term "alkenyl" refers to a monoradical of a branched or unbranched unsaturated hydrocarbon group having one or more double bonds and to cycloalkenyl groups having one or more rings wherein at least one ring contains a double bond. Alkenyl groups include those having 1, 2 or more double bonds and those in which two or more of the double bonds are conjugated double bonds. Alkenyl groups include those having from 2 to 20 carbon atoms, preferably having from 2 to 12 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cycloalkenyl groups include those having one or more rings. Cyclic alkenyl groups include those in which a double bond is in the ring or in an alkenyl group attached to a ring. Cyclic alkenyl groups include those having a 3-, 4-, 5-, 6-, 7-, 8-, 9-, 10-, 11- or 12-member carbon ring and particularly those having a 3-, 4-, 5-, 6- or 7-member ring. The carbon rings in cyclic alkenyl groups can also carry alkyl groups. Cyclic alkenyl groups can include bicyclic and tricyclic alkyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogens replaced with one or more fluorine atoms.

The term "aryl" refers to a chemical group having one or more 5-, 6- or 7-member aromatic or heterocyclic aromatic rings. An aromatic hydrocarbon is a hydrocarbon with a conjugated cyclic molecular structure. Aryl groups include those having from 4 to 30 carbon atoms, preferably having from 6 to 18 carbon atoms. Aryl groups can contain a single ring (e.g., phenyl), one or more rings (e.g., biphenyl) or multiple condensed (fused) rings, wherein at least one ring is aromatic (e.g., naphthyl, dihydrophenanthrenyl, fluorenyl, or anthryl). Heterocyclic aromatic rings can include one or more N, O, or S atoms in the ring. Heterocyclic aromatic rings can include those with one, two or three N, those with one or two O, and those with one or two S, or combinations of one or two or three N, O or S. Aryl groups are optionally substituted. Substituted aryl groups include among others those which are substituted with alkyl or alkenyl groups, which groups in turn can be optionally substituted. Specific aryl groups include phenyl groups, biphenyl groups, pyridinyl groups, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocylic aromatic group-containing groups corresponding to any one of the following benzene, naphthalene, naphthoquinone, diphenylmethane, fluorene, fluoranthene, anthracene, anthraquinone, phenanthrene, tetracene, naphthacenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic radical, including monovalent, divalent and polyvalent radicals, of the aromatic and heterocyclic aromatic groups listed above provided in a covalently bonded configuration in the compounds of the present invention. Aryl groups optionally have one or more aromatic rings or heterocyclic aromatic rings having one or more electron donating groups, electron withdrawing groups and/or targeting ligands provided as substituents.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl having one or more hydrogens replaced with one or more fluorine atoms, chlorine atoms, bromine atoms and/or iodine atoms.

Optional substitution of any alkyl, alkenyl and aryl groups includes substitution with one or more of the following substituents: halogens, —CN, —COOR, —OR, —COR, —OCOOR, —CON(R)$_2$, —OCON(R)$_2$, —N(R)$_2$, —NO$_2$, —SR, —SO$_2$R, —SO$_2$N(R)$_2$ or —SOR groups. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for alkyl and alkenyl groups include among others:
—COOR where R is a hydrogen or an alkyl group or an aryl group and more specifically where R is methyl, ethyl, propyl, butyl, or phenyl groups all of which are optionally substituted;
—COR where R is a hydrogen, or an alkyl group or an aryl groups and more specifically where R is methyl, ethyl, propyl, butyl, or phenyl groups all of which groups are optionally substituted;
—CON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;

—OCON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;

—N(R)$_2$ where each R, independently of each other R, is an alkyl group, acyl group or an aryl group and more specifically where R is methyl, ethyl, propyl, butyl, or phenyl or acetyl groups all of which are optionally substituted; or R and R can form a ring which may contain one or more double bonds.

—SR, —SO$_2$R, or —SOR where R is an alkyl group or an aryl groups and more specifically where R is methyl, ethyl, propyl, butyl, phenyl groups all of which are optionally substituted; for —SR, R can be hydrogen;

—OCOOR where R is an alkyl group or an aryl groups;

—SO$_2$N(R)$_2$ where R is a hydrogen, an alkyl group, or an aryl group and R and R can form a ring;

—OR where R is H, alkyl, aryl, or acyl; for example, R can be an acyl yielding —OCOR* where R* is a hydrogen or an alkyl group or an aryl group and more specifically where R* is methyl, ethyl, propyl, butyl, or phenyl groups all of which groups are optionally substituted.

As used herein, the term "alkylene" refers to a divalent radical derived from an alkyl group or as defined herein. Alkylene groups in some embodiments function as attaching and/or spacer groups in the present compositions. Compounds of the present invention include substituted and unsubstituted $C_1$-$C_{30}$ alkylene, $C_1$-$C_{12}$ alkylene and $C_1$-$C_5$ alkylene groups. The term "alkylene" includes cycloalkylene and non-cyclic alkylene groups.

As used herein, the term "cycloalkylene" refers to a divalent radical derived from a cycloalkyl group as defined herein. Cycloalkylene groups in some embodiments function as attaching and/or spacer groups in the present compositions. Compounds of the present invention include substituted and unsubstituted $C_1$-$C_{30}$ cycloalkenylene, $C_1$-$C_{12}$ cycloalkenylene and $C_1$-$C_5$ cycloalkenylene groups.

As used herein, the term "alkenylene" refers to a divalent radical derived from an alkenyl group as defined herein. Alkenylene groups in some embodiments function as attaching and/or spacer groups in the present compositions. Compounds of the present invention include substituted and unsubstituted $C_1$-$C_{20}$ alkenylene, $C_1$-$C_{12}$ alkenylene and $C_1$-$C_5$ alkenylene groups. The term "alkenylene" includes cycloalkenylene and non-cyclic alkenylene groups.

As used herein, the term "cycloalkenylene" refers to a divalent radical derived from a cylcoalkenyl group as defined herein. Cycloalkenylene groups in some embodiments function as attaching and/or spacer groups in the present compositions.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methyl-phenyl groups, particularly 4-methylphenyl groups, and methoxyphenyl groups, particularly 4-methoxyphenyl groups.

As used herein, the term "halo" refers to a halogen group such as a fluoro (—F), chloro (—Cl), bromo (—Br) or iodo (—I).

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

Overview

A Controlled Release Approach for Utilizing SLIPS to Prevent Microbial Surface Fouling and Kill Non-Adherent Pathogens in Surrounding Media.

Surface-associated fouling by bacteria is a common and persistent challenge facing the use of biomedical devices, industrial equipment, and many consumer products. The development of strategies that can slow or prevent microbial attachment and attenuate other bacterial behaviors on surfaces is thus an important element in the design of materials and coatings intended for use in wet environments. Embodiments of the present invention are motivated broadly by the recent development of slippery liquid-infused porous surfaces (or 'SLIPS'), which have physical properties and behaviors that render them well suited for the design of anti-biofouling surfaces.

SLIPS comprise a porous or textured surface infused with a viscous liquid (e.g., perfluorinated lubricants, silicone oil, etc.). This general design maintains the infused liquid as a thin, dynamic film at the surface, creating a hydrophobic or omniphobic interface that allows other fluids and substances to easily slide or 'slip' off the surface with sliding angles as low as 2°. Several recent reports reveal SLIPS to be a promising platform for the development of new anti-biofouling interfaces for biological and environmental applications. Indeed, SLIPS have been reported to resist fouling by a broad range of organisms, including clinically important bacterial and fungal pathogens, marine barnacle cyprids, and mammalian cells.

Slippery character is the sine qua non of a SLIPS-coated surface, but this essential quality only allows SLIPS to prevent fouling by organisms on the surfaces to which these coatings are physically applied. Conventional SLIPS-coated surfaces, for example, cannot prevent bacteria from colonizing other nearby (non-SLIPS-coated) surfaces. Conventional SLIPS also do not kill bacteria—organisms that are prevented from adhering to SLIPS-coated surfaces remain alive in the surrounding medium, and SLIPS do not currently have inherent mechanisms through which they can prevent these non-adherent (or 'planktonic') bacteria from producing toxins or engaging in other virulent behaviors, including forming biofilms on nearby unprotected surfaces.

To address these issues and develop new slippery anti-fouling surfaces that can also exert control over the behaviors of microorganisms in surrounding media, the present invention provides a new controlled release-based approach to the design of multifunctional SLIPS that prevent biofouling by pathogenic fungal and bacterial cells and kill planktonic microorganisms in surrounding media. In this approach, the properties of a porous polymer matrix and an infused silicone oil phase are leveraged to sustain the long-term release of small-molecule compounds, particularly agents directed toward microorganisms (such as bacteria and fungi). Experimental studies demonstrated that such small-molecule anti-microbial agents can be readily incorporated into SLIPS without impacting the anti-fouling properties of the SLIPS surfaces, and that the slow release of such anti-microbial agents can kill planktonic fungal cells effectively and improve the overall antifouling and antifungal properties.

Such anti-microbial agents include, but are not limited to triclosan and other broad-spectrum antibiotics. It should be noted, however, that the use of triclosan and other cytotoxic drugs (e.g., antibiotics) have several disadvantages in applied contexts, including the fact that the widespread use of these agents has led to evolved resistance in many clinically relevant pathogens.

EXAMPLES

Example 1—Fabrication of SLIPS Material with an Antimicrobial (Triclosan)

Many types of slippery liquid-infused porous surfaces (or 'SLIPS') can resist adhesion and colonization by microorganisms. These 'slippery' materials thus offer new approaches to prevent fouling on a range of commercial and industrial surfaces, including biomedical devices. However, while SLIPS can prevent fouling on surfaces to which they are applied, they can currently do little to prevent the proliferation of non-adherent (planktonic) organisms, stop them from colonizing other surfaces, or prevent them from engaging in other behaviors that could lead to infection and associated burdens. The present examples provide an approach to the design of multi-functional SLIPS that addresses these issues and expands the potential utility of slippery surfaces in antimicrobial contexts.

This approach is based on the incorporation and controlled release of small-molecule antimicrobial agents from the porous matrices used to host infused slippery oil phases. The below examples demonstrate that SLIPS fabricated using nanoporous polymer multilayers can prevent short- and longer-term colonization and biofilm formation by four common fungal and bacterial pathogens (*Candida albicans, Pseudomonas aeruginosa, Escherichia coli,* and *Staphylococcus aureus*), and that the polymer and oil phases comprising these materials can be exploited to load and sustain the release of triclosan, a model hydrophobic and broad-spectrum antimicrobial agent, into surrounding media. This approach both improves the inherent anti-fouling properties of these materials and endows them with the ability to efficiently kill planktonic pathogens.

Finally, this approach can be used to fabricate dual-action SLIPS on complex surfaces, including the luminal surfaces of flexible catheter tubes. This strategy has the potential to be generally applicable and it is anticipated that the materials, strategies, and concepts reported here will enable new approaches to the design of slippery surfaces with improved anti-fouling properties and open the door to new applications of slippery liquid-infused materials that host or promote the release of a variety of other active agents.

Materials and Methods.

In an embodiment, poly(2-vinyl-4,4-dimethylazlactone) (PVDMA) was synthesized by free-radical polymerization of VDMA as described previously (Buck et al., Chem. Mater. 2010, 22, 6319). Branched poly(ethyleneimine) (BPEI; MW ~25,000), propylamine, n-decylamine (95%), acetone (HPLC grade), tetrahydrofuran (THF, HPLC grade), and silicone oil for melting point and boiling point apparatuses (viscosity=45-55 cSt at 25° C.) were purchased from Sigma Aldrich (Milwaukee, Wis.). D-Glucamine (>95%) was purchased from TCI America (Portland, Oreg.). Glass microscope slides were purchased from Fischer Scientific (Pittsburgh, Pa.). Triclosan (5-chloro-2-(2,4-dichlorophenoxy)phenol) was purchased from Alfa Aesar (Ward Hill, Mass.).

Thin sheets of poly(ethylene terephthalate) film (PET; 0.004 in. thick) were purchased from McMaster Carr (Elmhurst, Ill.). Aluminum foil was obtained from Reynolds Consumer Products, LLC (Richmond, Va.). Polyethylene tubing (PE-100, inner diameter=0.034 in.) was purchased from Intramedic (Franklin Lakes, N.J.). Roswell Park Memorial Institute (RPMI) 1640 powder (with L-glutamine and phenol red, without HEPES and sodium bicarbonate), FUN-1 cell stain, fetal bovine serum (FBS) and 2,3-bis-(2-methoxy-4-nitro-5-sulfophenyl)-2H-tetrazolium-5-carboxanilide (XTT) were purchased from Invitrogen (Grand Island, N.Y.). 3-(N-Morpholino)propanesulfonic acid (MOPS), Tris-base, phosphate-buffered saline (PBS) liquid concentrate (10×), and NaCl were purchased from Fisher Scientific (Pittsburgh, Pa.). Menadione, glutaraldehyde, and formaldehyde were purchased from Sigma (St. Louis, Mo.). Tween-20 was purchased from Acros (Grand Island, N.Y.). Osmium tetroxide (4%) was purchased from Electron Microscopy Sciences (Hatfield, Pa.).

*Escherichia coli* strain ATCC 8739, *Staphylococcus aureus* strain ATCC10390, and HeLa cells were purchased from American Type Culture Collection (ATTC; Manassas, Va.). *Pseudomonas aeruginosa* strain (PAO1) was obtained from the University of Rochester. SYTO-9 staining kits were purchased from ThermoFisher (Waltham, Mass.). All chemicals, reagents, and solvents were used as received without further purification unless otherwise noted.

General Considerations.

Compressed air used to dry samples was filtered through a 0.2 µm membrane syringe filter. Scanning electron micrographs were acquired using a LEO 1530 scanning electron microscope (SEM) at an accelerating voltage of 5 kV. Samples were coated with a thin layer of gold using a gold sputterer operating at 45 mA under a vacuum pressure of 50 mTorr for 40 seconds prior to imaging. Critical point drying was used to prepare fungal biofilm samples for SEM imaging using a Critical Point Dryer (Tousimis Samdri-815). Digital pictures were acquired using a Canon PowerShot SX130 IS digital camera.

Water contact angles were measured using a Dataphysics OCA 15 Plus contact angle goniometer at ambient temperature with 10 µL of deionized water. Fluorescence microscopy was performed using an Olympus IX71 microscope and images were obtained using the MetaMorph Advanced version 7.8.1.0 software package. Images were processed using NIH Image J software and Microsoft Powerpoint 2010. In all tube-based experiments described below in this example, the ends of the tubes were left open. In droplet-based and tube-based experiments, substrates were placed in a humidified microenvironment before incubating at 37° C.

Absorbance measurements used in XTT assays were acquired at 490 nm using a plate reader (EL800 Universal Microplate Reader, Bio-Tek Instruments, Inc.). The M9 buffer used in triclosan release experiments was prepared with the following previously reported composition: 8.6 mM NaCl, 47.7 mM Na2HPO4, 21.7 mM KH2PO4, 18.7 mM NH4Cl, pH 7.35 (see De Kievit et al., Appl. Environ. Microbiol., 2001, 67, 1865; and Frei et al., Angew. Chem. Int. Ed. 2012, 51, 5226).

Covalent Layer-by-Layer Assembly of Porous Polymer Multilayers.

Porous PEI/PVDMA multilayers were deposited on glass substrates using a previously reported procedure (see Manna et al., Adv. Mater. 2015, 27, 3007; and Manna et al., Adv.

Funct. Mater. 2015, 25, 1672). Briefly: (i) substrates were submerged in a solution of PEI (20 mM in acetone with respect to the polymer repeat unit) for 20 seconds; (ii) substrates were removed and immersed in an initial acetone bath for 20 seconds followed by a second acetone bath for 20 seconds; (iii) substrates were submerged in a solution of PVDMA (20 mM in acetone with respect to the polymer repeat unit) for 20 seconds; and (iv) substrates were removed and rinsed again using the procedure outlined under step (ii). This cycle was repeated 35 times to fabricate porous polymer multilayers consisting of 35 PEI/PVDMA layer pairs (or 'bilayers').

The concentrations of the polymer solutions were maintained during assembly by the addition of acetone as needed to compensate for solvent evaporation after every dipping cycle. All other substrates used in this study (e.g., catheter tubes, aluminum foil, PET film, and PTFE tubes) were also coated using this general protocol. Multilayers were characterized and used in subsequent experiments immediately or dried under a stream of filtered, compressed air and stored in a vacuum desiccator until use. All films were fabricated at ambient room temperature.

Chemical Functionalization of Multilayers and Infusion of Oils.

Porous polymer multilayers containing unreacted azlactone groups, prepared as described above, were functionalized by treatment with solutions of decylamine (20 mM in THF) (see Manna et al., Adv. Mater. 2015, 27, 3007; and Manna et al., Adv. Mater. 2012, 24, 4291).

Functionalized films were then rinsed with THF and acetone and dried with filtered air. The resulting hydrophobic multilayers were infused with lubricating liquids (e.g., silicone oil) using the following general protocols. For planar substrates, a droplet of 3 µL of oil was placed onto a film and spread over the surface using weighing paper. For experiments involving coated tubes, film-coated tubes were infused with oil by placing a 4 µL silicone oil droplet at the top end of a vertical tube and allowing gravity-driven spreading of the oil from the top to the bottom of the tube. Excess oil was removed by tapping the bottom end of the tube on a disposable wipe.

Loading and Release of Triclosan.

The small-molecule antimicrobial agent triclosan was loaded into porous multilayers prior to the infusion of silicone oil by treating film-coated substrates with a desired number of 10 µL droplets of a solution of triclosan (50 mg/mL) in acetone and allowing the acetone to evaporate under ambient conditions for 5 minutes. All films were then dried under vacuum and infused with silicone oil as described above. Characterization of the release of triclosan from these loaded SLIPS was performed by incubating loaded SLIPS-coated substrates in 750 µL of PBS buffer at 37° C. The release of triclosan as a function of time was monitored by UV/vis spectrophotometry at a wavelength of 222 nm. At desired time points, buffer was removed for analysis using a pipette and replaced by a fresh 750 µL aliquot.

Characterization of Fungal Cell Adhesion on SLIPS-Coated Substrates.

*C. albicans* SC5314 cells were grown overnight at 30° C. in liquid yeast extract-peptone-dextrose (YPD) medium. Cells were washed with PBS and re-suspended in RPMI 1640 medium buffered with MOPS (pH 7.0). The cell density was adjusted to $10^7$ cfu/mL with RPMI 1640 for experiments with SLIPS that did not contain triclosan, and to $10^6$ cfu/mL for experiments using SLIPS loaded with triclosan. For initial screens, 50 µL droplets of cell suspension were placed on both planar SLIPS-coated and planar bare glass surfaces and incubated at 37° C.

Substrates were removed from the incubator after 3 hours and characterized using either a macroscopic crystal violet stain or a microscopic yeast cell viability dye. The macroscopic cell stain assay was performed by adding 20 µL of a crystal violet solution [CV; 1% (w/w) in deionized water] to droplets of yeast sitting on the surfaces of SLIPS-coated glass or bare glass substrates and incubating at 37° C. for 30 minutes. Substrates were then removed from the incubator and placed in an inclined position at a desired angle to characterize and compare the anti-fouling properties of the substrates. Microscopic cell viability assays were performed by adding 25 µL of a 10 µM solution of the fungal cell viability probe FUN-1 to the yeast droplets and incubating at 37° C. for at least 30 minutes before imaging using a fluorescence microscope.

Estimation of Biofilm Adhesion on SLIPS-Coated Substrates.

*C. albicans* SC5314 cells were grown overnight at 30° C. in liquid YPD medium. Cells were washed with PBS and resuspended in RPMI 1640 medium buffered with MOPS (pH 7.0) and supplemented with 5% fetal bovine serum to stimulate biofilm formation. The cell density was manually adjusted to $10^6$ cfu/mL. SLIPS-coated substrates and other control substrates (bare glass, silicone oil-wetted glass, and multilayer-coated glass without silicone oil) were individually submerged in 1 mL of cell suspension ($10^6$ cfu/mL) in each well of a 24-well plate. The plate was incubated at 37° C. for 24 hours, after which time either (i) the biofilms formed on the surfaces of the substrates were visualized using the cell stain FUN-1 (200 µL of 10 µM FUN-1, incubated for 30 minutes at 37° C.) or (ii) the metabolic activity of the cells was evaluated. For evaluation of metabolic activity, substrates were carefully removed from the wells, excess liquid was removed and substrates were placed in new wells; 200 µL of XTT solution (0.5 g/L in PBS, pH 7.4, containing 3 µM menadione in acetone) was added to every well containing a substrate, including negative control wells that did not have any yeast or substrate in them.

After 2 hours of incubation at 37° C., 75 µL of the supernatant was transferred to a 96-well plate and the absorbance of the solution at 490 nm was measured. Background absorbance from wells containing medium and XTT alone was subtracted from all readings and results were plotted relative to the absorbance values of wells containing samples of solution from control untreated surfaces. Similar sets of experiments were carried out for SLIPS-coated PET film and SLIPS-coated aluminum foil. For studies involving the use of triclosan-loaded SLIPS, the metabolic activity of cells in solution was also quantified (in both triclosan-loaded and non-triclosan-loaded control coatings) in addition to characterization of the metabolic activity of surface-associated cells.

For multiple challenge experiments, substrates were incubated with yeast, as described above. At the end of each 24-hour period, substrates were removed from their wells and imaged to characterize the extent to which yeast was adhered on the surface. The SLIPS-coated substrates were then incubated in fresh *C. albicans* suspensions to perform the next challenge (new bare glass substrates were used in control experiments). Three such 24-hour challenges were performed, and at the end of the third challenge, XTT was used to quantify the reduction in metabolic activity of cells on the surface of the SLIPS substrates compared to glass controls. Similar multiple challenge experiments, consisting of five consecutive challenges, were performed using triclosan-loaded SLIPS. In those experiments, the metabolic activities of both substrate-associated and planktonic cells were quantified at the end of every challenge.

Characterization of Fungal Cell Adhesion in SLIPS-Coated Catheter Tubes.

A 15 µL aliquot of a C. albicans suspension ($10^7$ cfu/mL) was incubated in 3 cm segments of SLIPS-coated PE tubes at 37° C. After 4 hours, the amount of attached cells in the tubes was both qualitatively and quantitatively estimated using three different methods: (i) a metabolic XTT assay, (ii) by visualizing the biofilm formed using SEM, and (iii) using the FUN-1 cell stain assay as described above. For the metabolic assay, yeast solution was removed from the tubes and placed in a well containing 50 µL of XTT (0.5 g/L in PBS, pH 7.4, containing 3 µM menadione in acetone).

A 15 µL aliquot of XTT was also incubated inside the emptied tubes. Both preparations were incubated at 37° C. for 2 hours, after which the absorbance of the solutions was measured at 490 nm to quantify the relative metabolic activity of yeast on the surface of the tubes and inside the tubes. For analysis by SEM, catheter tube segments were placed in a fixative solution [1% (v/v) glutaraldehyde and 4% (v/v) formaldehyde] overnight at 4° C. The samples were rinsed in PBS (0.1 M) for 10 minutes and then placed in osmium tetroxide (1%) for 30 minutes, followed by 10 minutes in PBS (0.1 M). The samples were subsequently dehydrated in a series of ethanol washes (30%, 50%, 70%, 85%, 95%, and 100% for 20 minutes each). Final desiccation was accomplished by critical point drying.

Specimens were mounted on aluminum stubs and sliced open to reveal the inside of the catheter, then sputter coated with gold-palladium. Samples were then imaged in high-vacuum mode at 5 kV. The antifungal and anti-biofilm activities of triclosan-loaded, SLIPS-coated PTFE tubes were characterized by incubating 40 µL of a $10^6$ cfu/mL C. albicans cell suspension in a 2 cm tube segment for 4 hours at 37° C. After 4 hours, a metabolic XTT assay was performed as outlined above.

Characterization of Bacterial Biofilm Adhesion on SLIPS-Coated Substrates.

Freezer stocks of bacterial strains were maintained at −80° C. in 1:1 LB:glycerol. Overnight cultures of bacteria were grown in Luria-Bertani (LB) medium (P. aeruginosa and E. coli) or tryptic soy broth (S. aureus) at 37° C. with shaking at 200 rpm. Biofilms attached to SLIPS-coated glass and bare glass substrates were imaged by fluorescence microscopy.

An inoculating subculture of P. aeruginosa was prepared by centrifugation of the overnight culture at 4,000×g for 10 min followed by resuspension of the cell pellet in an amount of fresh M9+ medium, effecting a 1:10 dilution (v/v) of the overnight culture (M9+ medium consists of the M9 buffer, described above, supplemented with 0.4% arginine, 0.5% casamino acids, 0.2% glucose, 0.2% succinate, 0.2% citrate, 0.2% glutamate, 1 mM $MgSO_4$, and 0.1 mM $CaCl_2$) (see Frei et al., Angew. Chem. Int. Ed. 2012, 51, 5226). A subculture of S. aureus was prepared by diluting overnight cultures 1:100 into fresh brain-heart infusion medium supplemented with 1% (w/v) glucose (see Kratochvil et al., ACS Biomater. Sci. Eng. 2015, 1, 1039). E. coli subcultures were prepared by diluting overnight cultures 1:1000 into fresh LB medium.

Both bare glass substrates and SLIPS-coated substrates were placed individually into the wells of a 12-well microtiter plate (Costar 3737) and sterilized by UV irradiation for 20 minutes in a biological safety cabinet. Bacterial subculture (P. aeruginosa, S. aureus, E. coli) was then added to each well in 2 mL aliquots and the plates were incubated under static conditions at 37° C. for 24 h.

Substrates were then removed from the wells using forceps, gently dabbed on a paper towel to remove excess liquid, and placed in the wells of a new 12-well plate to perform biofilm staining with SYTO-9 according to the manufacturer's protocol. Excess staining solution was removed by dabbing on a paper towel and the substrates were then transferred to the wells of a 24-well plate and covered by 400 µL PBS. Biofilms were then imaged using an Olympus IX71 fluorescence microscope.

Characterization of Mammalian Cell Attachment on SLIPS-Coated Surfaces.

All surfaces were sterilized prior to the seeding of cells by exposure to UV light for 15 minutes in a biological safety cabinet. The substrates were then placed individually into the wells of 24-well tissue culture-treated polystyrene culture plates. HeLa cells were cultured in growth medium (MEM supplemented with 10% v/v fetal bovine serum, 100 units/mL penicillin and 100 µg/mL streptomycin), seeded on both SLIPS-coated and bare glass substrates at initial densities of 50,000 cells/mL in 750 µL of growth medium, and incubated at 37° C. for 72 hours. Cytotoxicity measurements were conducted in replicates of three using a commercially available fluorescence live/dead assay kit (Molecular Probes).

For imaging, cells were stained with 500 µL of a staining solution containing calcein AM and ethidium homodimer staining solution (1 µg/mL in PBS) for 45 minutes at 37° C. Following incubation, the staining solution was aspirated and replaced with 1 mL of fresh growth medium and cells were imaged by fluorescence microscopy.

Example 2—Prevention of Adhesion Using SLIPS Material

Multilayer-Based SLIPS Prevent Adhesion of C. albicans.

It was recently reported that nanoporous and superhydrophobic polymer multilayers fabricated by the reactive layer-by-layer assembly of PEI and the amine-reactive polymer PVDMA can be infused with hydrophobic oils to design surfaces that are 'slippery' to a range of aqueous fluids (see Manna et al., Adv. Mater. 2015, 27, 3007). The work described here (i) characterizes the ability of these slippery oil-infused surfaces to prevent the short- and longer-term attachment and colonization of fungal and bacterial cells, and (ii) tests the hypothesis that the porous polymer matrix and liquid oil phases comprising these materials could be exploited as reservoirs for the loading and release of antimicrobial agents that could both improve the inherent antifouling properties of these surfaces and provide new strategies to kill non-adherent (planktonic) cells in surrounding media.

For all of the work described here, SLIPS fabricated by the infusion of silicone oil into nanoporous, decylamine-functionalized PEI/PVDMA films ~3.5 µm thick were used. Past studies by the present inventors demonstrate that SLIPS having this general structure and composition exhibit water-droplet sliding angles as low as 1° and can be fabricated on a broad range of objects, including the inner surfaces of tubes.

Silicone oil was used as a model hydrophobic oil, rather than the highly fluorinated oils used by many other groups to design SLIPS in other studies (see Wong et al., Nature 2011, 477, 443; Epstein et al., Proc. Natl. Acad. Sci. U.S.A. 2012, 109, 13182; Leslie et al., Nat. Biotechnol. 2014, 32, 1134; and Xiao et al., ACS Appl. Mater. Inter. 2013, 5, 10074), on the basis of the inventors' past results and because silicone oil can be used as a solvent for a range of different small-molecule (drug-like) agents.

A series of initial experiments was performed to characterize the ability of SLIPS-coated planar glass substrates to prevent fouling by *C. albicans*, an opportunistic human pathogen that is the leading cause of hospital-acquired systemic fungal infections. These experiments were performed by incubating 50 µL droplets of *C. albicans* yeast inocula onto horizontal bare (control) and SLIPS-coated glass surfaces for 3 hours at 37° C. The droplets were then stained using crystal violet, which is a dye used widely to stain microbial biomass and provide a visual means of assessing the extent of macroscopic surface colonization (see Peeters et al., J. Microbiol. Meth. 2008, 72, 157; and Taff et al., Med. Mycology 2012, 50, 214), and the substrates were tilted gradually from their initial horizontal positions to identify the angle at which the droplets started to slide down the surfaces of the substrates (FIG. 1 (A)).

For SLIPS-coated glass substrates, a tilt angle of 10° was sufficient to promote sliding of beaded droplets of inocula, and sliding occurred down the surface without leaving behind a trail of either liquid or yeast cells (FIG. 1 (B)). Furthermore, no staining was observed on the surfaces of the SLIPS in the locations where the droplets were initially placed. In contrast, droplets of yeast inocula spread readily on the surfaces of bare glass substrates and required extreme tilt angles of 90° to promote sliding (FIG. 1 (C)). On bare glass, sliding left behind a prominent trail of residual liquid, and upon washing the substrate we observed adherent biomass to be present where the droplets of inocula were initially placed.

To confirm these observations, a similar series of experiments were performed using the yeast-specific fluorescent dye FUN-1 to characterize the presence or absence of live yeast cells. After tilting the substrates and washing them as described above, bright and uniform green and red fluorescence were observed on the surfaces of bare glass substrates, indicating the presence of substantial numbers of metabolically active yeast cells (FIG. 1 (D-F); green is cytoplasmic staining; red indicates intravacuolar structures in metabolically active cells). In contrast, the surfaces of SLIPS-coated glass slides were dark and almost completely devoid of fluorescence (FIG. 1 (G-I)).

When combined, these results demonstrate that glass surfaces coated with silicone oil-infused porous PEI/PVDMA multilayers can substantially prevent the adhesion or attachment of *C. albicans* yeast for short incubation periods.

Multilayer-Based SLIPS Resist the Formation of *C. albicans* Biofilms.

A second series of experiments was performed to determine whether these PEI/PVDMA-based SLIPS could prevent the attachment and colonization of yeast for longer periods and thus prevent or reduce the formation of *C. albicans* biofilms.

For these experiments, SLIPS-coated glass substrates were immersed into the wells of 24-well plates containing suspensions of *C. albicans* in media conditioned to stimulate biofilm formation, and incubated them at 37° C. for 24 hours (bare glass substrates, bare glass smeared with silicone oil (no polymer matrix), and multilayer-coated glass substrates (no oil) were also included as controls). After 24 hours, the substrates were then either (i) stained directly with FUN-1 to visualize cells attached to the surface or (ii) carefully removed and placed into empty wells to quantify the metabolic activity of attached cells using an XTT assay.

Figure 2:
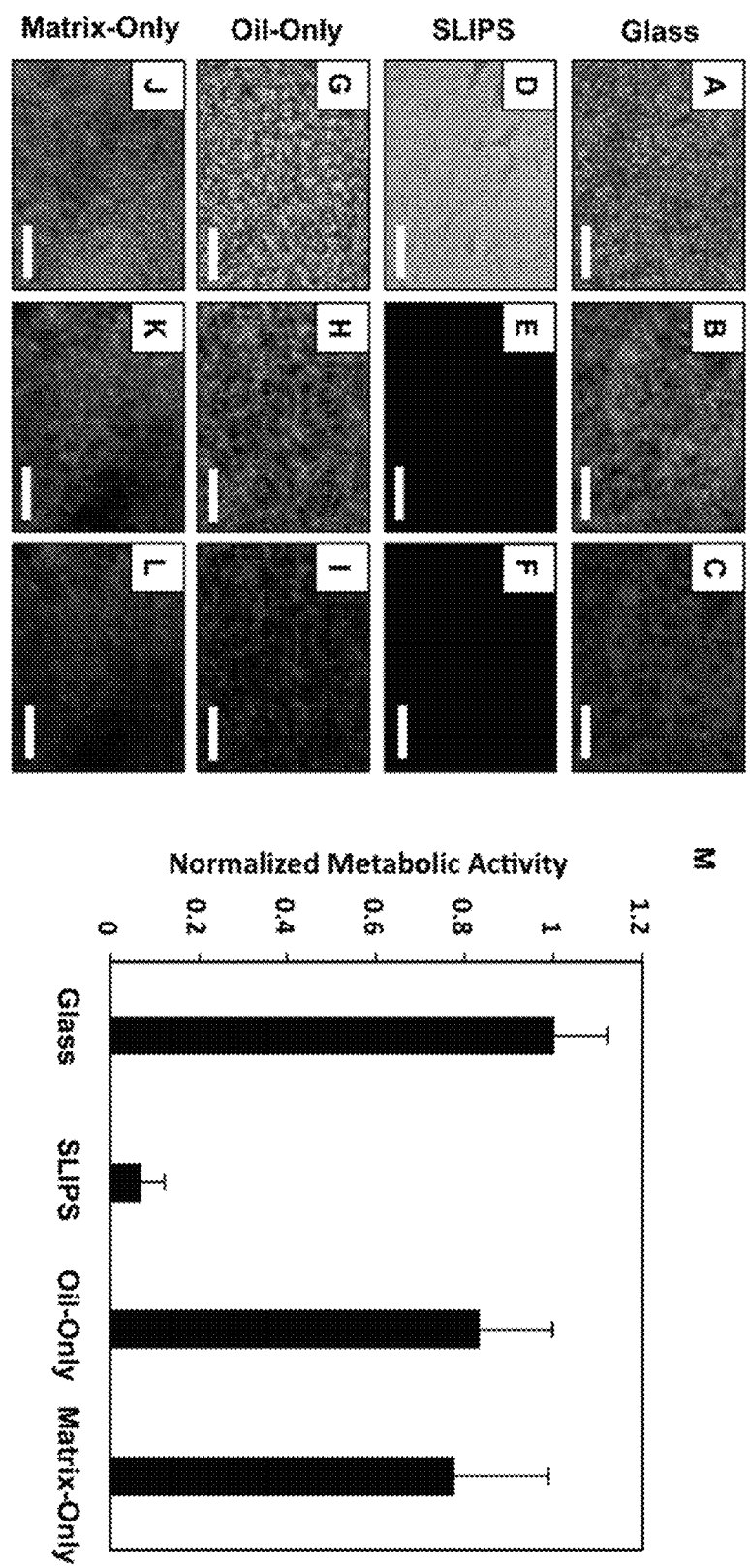
FIG. 2: (A-L) Phase contrast and fluorescence microscopy images of bare glass (A-C), SLIPS-coated glass (D-F), oil-smeared glass (oil only; G-I), and porous polymer matrix (matrix only; J-L) surfaces immersed in suspensions of C. albicans for 24 hours; cells were stained with FUN-1 fluorescent dye prior to imaging. (M) Plot showing the quantified metabolic activity of C. albicans on the surfaces of bare glass, SLIPS-coated glass, oil-smeared glass (oil only), and porous polymer multilayers (matrix only) after immersion in suspensions of C. albicans for 24 hours; metabolic activity was quantified using an XTT assay. Scale bars are 200 µm. Error bars represent standard deviation.

Robust biofilms exhibiting substantial metabolic activity were observed on all three control substrates (bare glass, oil-treated glass, and multilayers without oil) by fluorescence microscopy (FIGS. 2 (A-C) and (G-L)) and the XTT assay (FIG. 2 (M)). In contrast, SLIPS-coated surfaces were almost completely devoid of biofilm (as determined by fluorescence microscopy; FIG. 2 (D-F) and exhibited very low metabolic activity compared to the control surfaces (FIG. 2 (M)).

Figure 10:
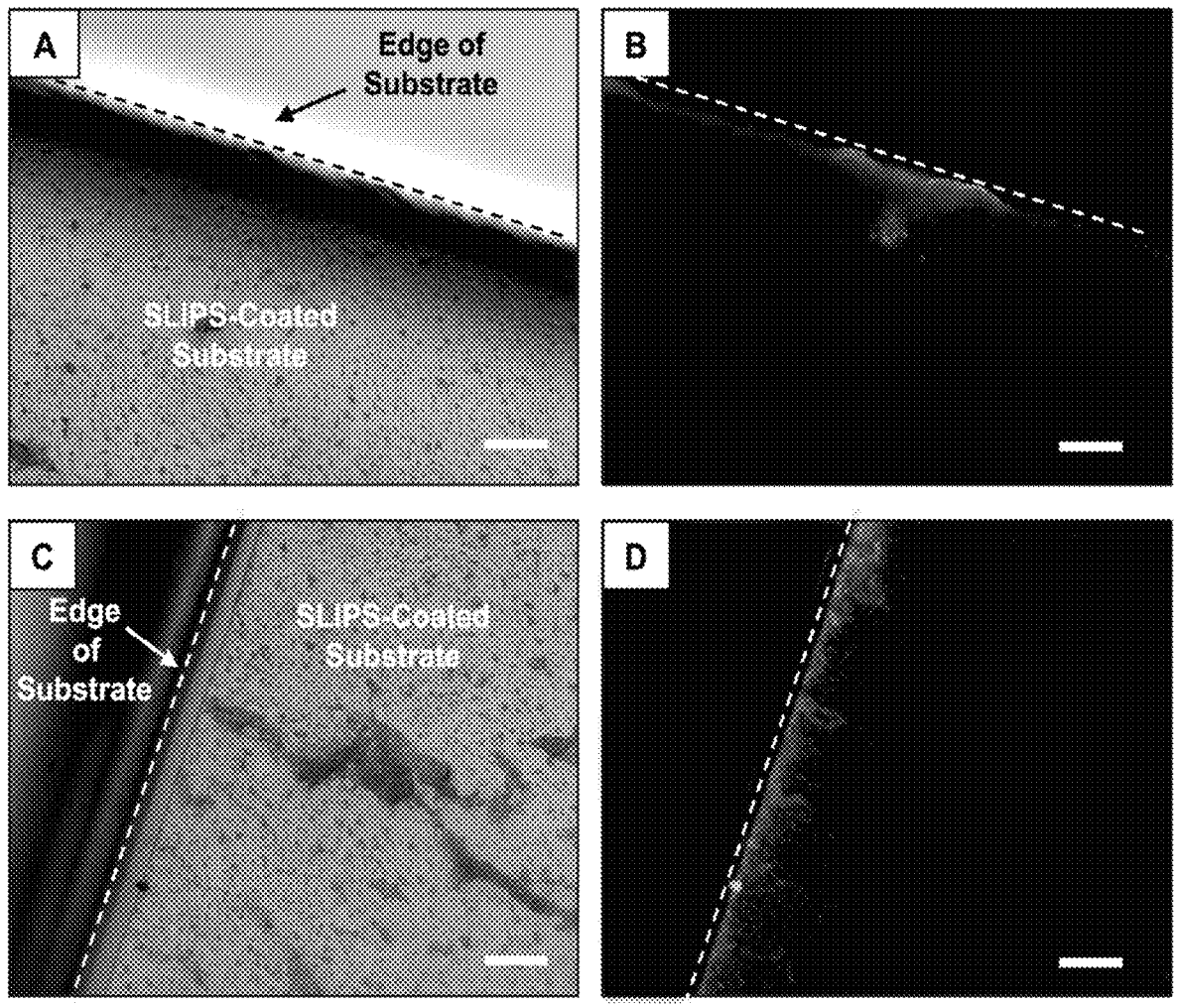
FIG. 10: (A-D) Representative bright-field (A,C) and fluorescence (B,D) microscopy images showing the edges of SLIPS-coated glass substrates incubated in the presence of C. albicans for 24 hours. Samples were stained with FUN-1 fluorescent dye prior to imaging, and show small and isolated patches of biofilm (green) located along the edges and corners of the coated substrates. The approximate locations of the edges of the substrates are indicated with black or white dotted lines. Scale bars=100 µm.

These results demonstrate that the individual components of these SLIPS themselves (i.e., the porous polymer matrix and silicone oil) are not substantially cytotoxic, and suggest that the absence of biofilm on SLIPS-coated surfaces arises instead from slipperiness imparted by the fruitful combination of these two components. It is noted, however, that while these materials can substantially prevent biofilm formation under these conditions, small and isolated patches of biofilm were occasionally observed along the edges and corners of the coated glass substrates (FIG. 10) where defects may prevent uniform coverage by the SLIPS (these small patches of biofilm observed visually likely also account for the small amount of metabolic activity observed in our XTT assays; e.g., ~6% as compared to biofilms formed on bare glass substrates; see FIG. 2 (M)). This observation is discussed further in the sections below.

To characterize the anti-fouling properties of these SLIPS for longer periods, a 'multiple challenge' experiment was performed in which substrates were repeatedly (i) immersed in suspensions of yeast for 24 hours, (ii) removed from the yeast suspensions and characterized, and (iii) immersed again in fresh yeast suspensions for another 24 hours (see the discussion above for additional details related to materials and methods used in these experiments). This multiple challenge protocol was adopted to circumvent limitations associated with the depletion of nutrients (and resulting cell death) that would occur during prolonged, multiple-day immersion in a single yeast suspension. In addition to the multiple microbial challenges, this protocol also allowed potential changes in anti-fouling properties that could occur as a result of the physical manipulation and re-use of SLIPS-coated surfaces to be assessed, including multiple passages through air/water interfaces.

Figure 3:
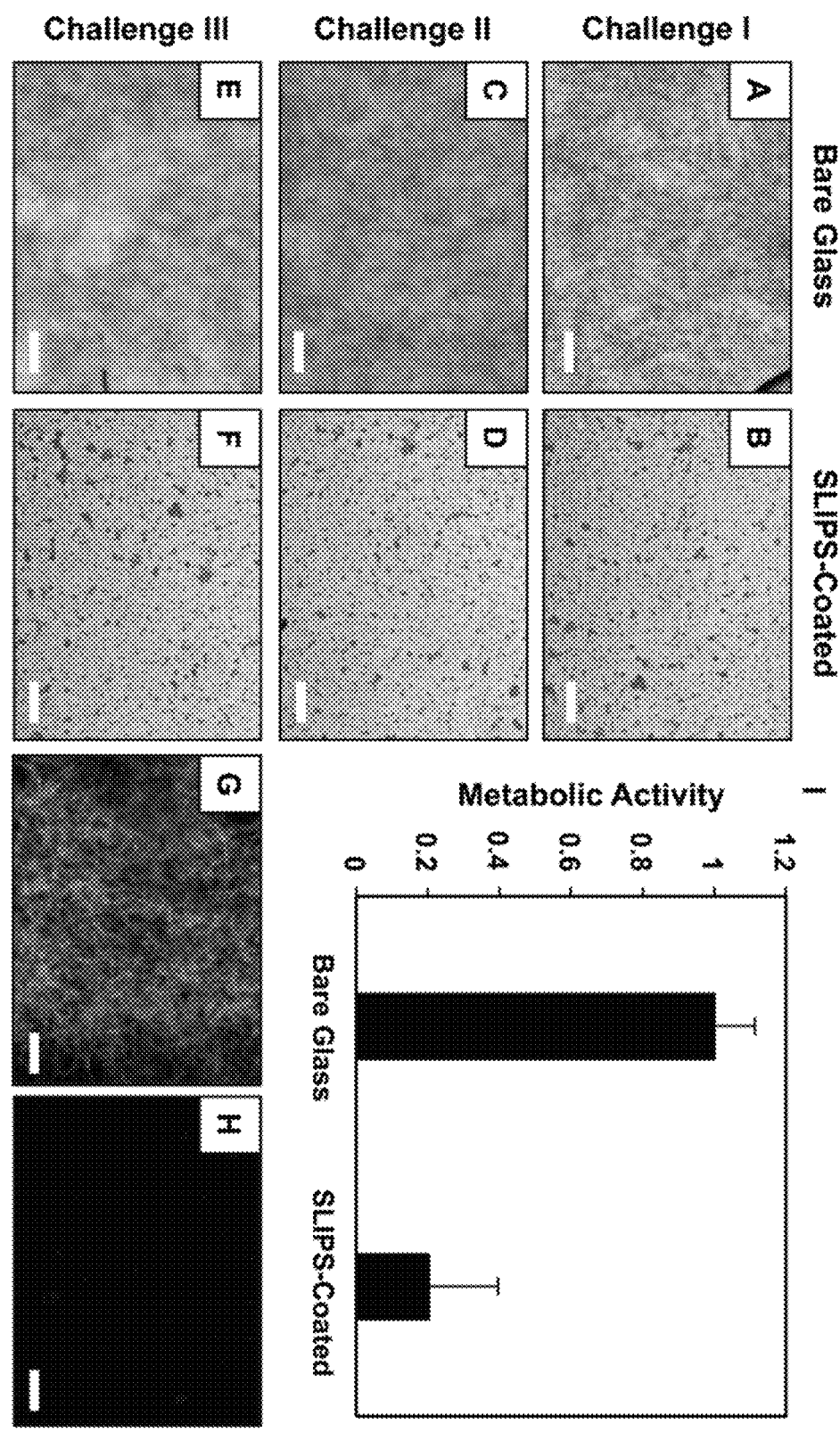
FIG. 3: (A-F) Bright-field microscopy images showing the surfaces of bare glass and SLIPS-coated glass substrates after three consecutive 24-hour challenges with C. albicans suspensions. (G-H) Fluorescence microscopy images of the same surfaces shown in (E-F) after staining with the FUN-1 fluorescent dye. (I) Plot showing the quantified metabolic activity of C. albicans on the surfaces of bare glass and SLIPS-coated glass after the third consecutive challenge; metabolic activity was quantified using an XTT assay. Scale bars are 100 µm. Error bars represent standard deviation.

After each 24-hour challenge, the substrates were removed to characterize slipperiness and extents of biofilm formation. FIG. 3 shows representative results of an experiment involving three consecutive microbial challenges and reveals that SLIPS-coated surfaces maintained their anti-fouling properties, compared to bare glass controls, as determined by bright-field and fluorescence microscopy characterization of FUN-1-stained surfaces (FIG. 3 (A-H)). It is noted that the dark punctate and granular structures observed in the bright-field images of SLIPS-coated surfaces (FIG. 3 (B,D,F)) are associated with the textures of the nanoporous multilayer scaffolds, and do not represent yeast cells or biofilm (a result that is confirmed by the lack of green fluorescence in the FUN-1-stained SLIPS-coated surfaces shown in FIG. 3 (H)).

After the third microbial challenge, differences in the metabolic activities of cells present on the surfaces of the substrates (FIG. 3 (I)) were also quantified. SLIPS-coated substrates exhibited an ~80% reduction in biofilm formation as compared to bare glass substrates. Based on this result and visual inspection of FUN-1-stained samples, the ~20% metabolic activity observed here (relative to controls) was attributed to the presence of small patches of biofilm located at the corners and edges of the SLIPS-coated substrates, as described above, and not to the presence of biofilm over the remaining majority of the liquid-infused surfaces.

Characterization of Anti-Fouling Behavior in SLIPS-Coated Catheter Tube Segments.

Figure 11:
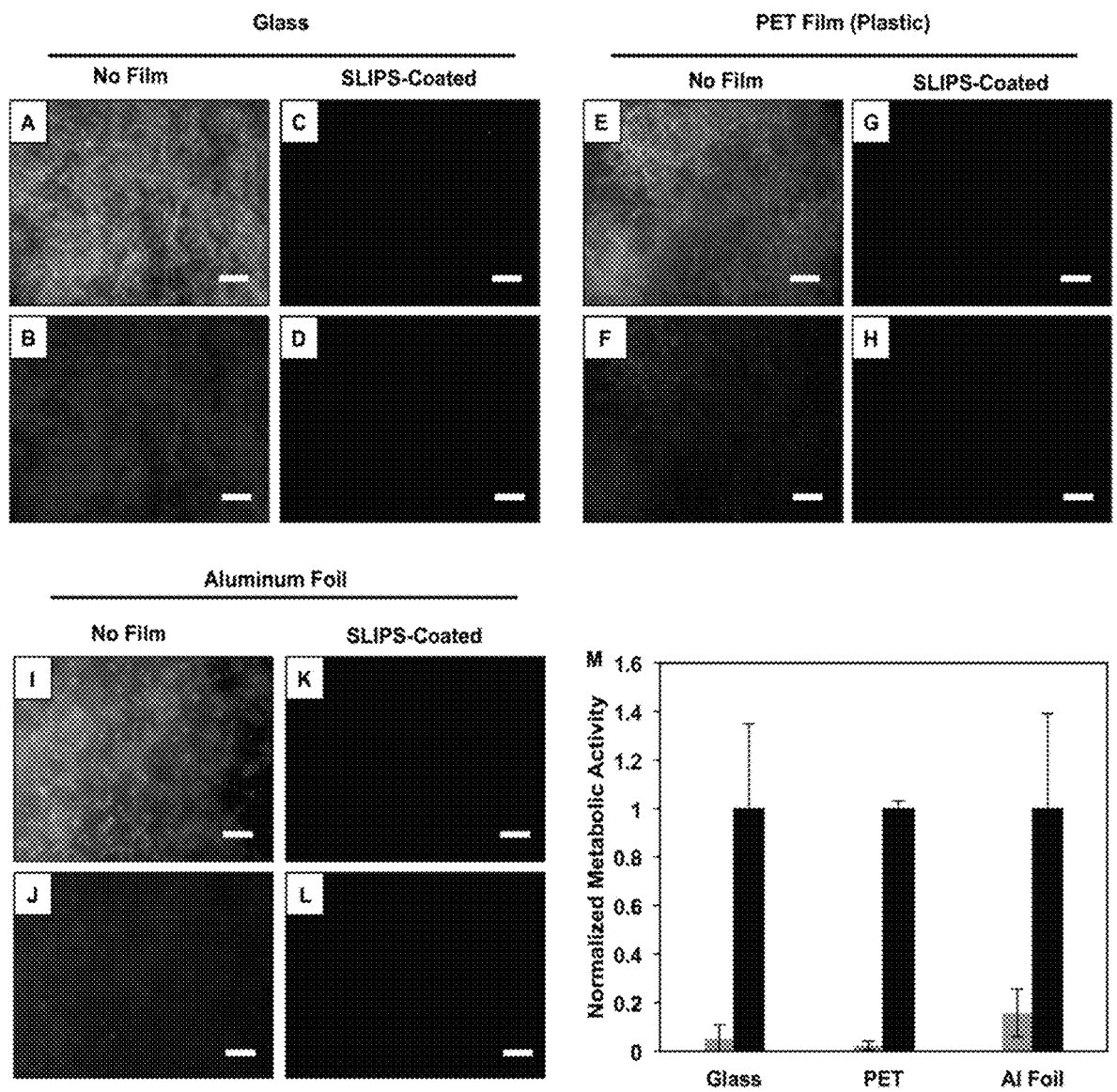
FIG. 11: (A-L) Representative fluorescence microscopy images of substrates incubated in the presence of C. albicans for 24 hours. Samples were stained with FUN-1 fluorescent dye prior to imaging; green indicates cytoplasmic staining and red indicates intravacuolar structures in live cells. The images show results for both bare and SLIPS-coated glass substrates (A-D), plastic PET film substrates (E-H), and aluminum foil substrates (I-L). Scale bars are 100 µm. (M) Plot showing the quantified metabolic activity of C. albicans on bare and SLIPS-coated glass, PET, and aluminum foil substrates after immersion in suspensions of C. albicans for 24 hours; metabolic activity was quantified using an XTT assay. Error bars represent standard deviation.

One useful feature of the layer-by-layer process used to fabricate the materials reported here is that it permits the fabrication of SLIPS on a variety of types of surfaces, including plastic and metal surfaces and flexible, curved, or topologically complex surfaces (e.g., tubing) typical of devices or equipment relevant in applied industrial or biomedical contexts (see Huang et al., ACS Macro Lett. 2013, 2, 826; Manna et al., Adv. Mater. 2015, 27, 3007; and Sunny et al., Adv. Funct. Mater. 2014, 24, 6658). The results of experiments shown in FIG. 11 demonstrate that multilayer-based SLIPS can also prevent C. albicans biofilm formation on the surfaces of flexible plastic (PET; FIG. 11 (E-H)) and metal (aluminum foil; FIG. 11 (I-L)) surfaces.

Figure 4:
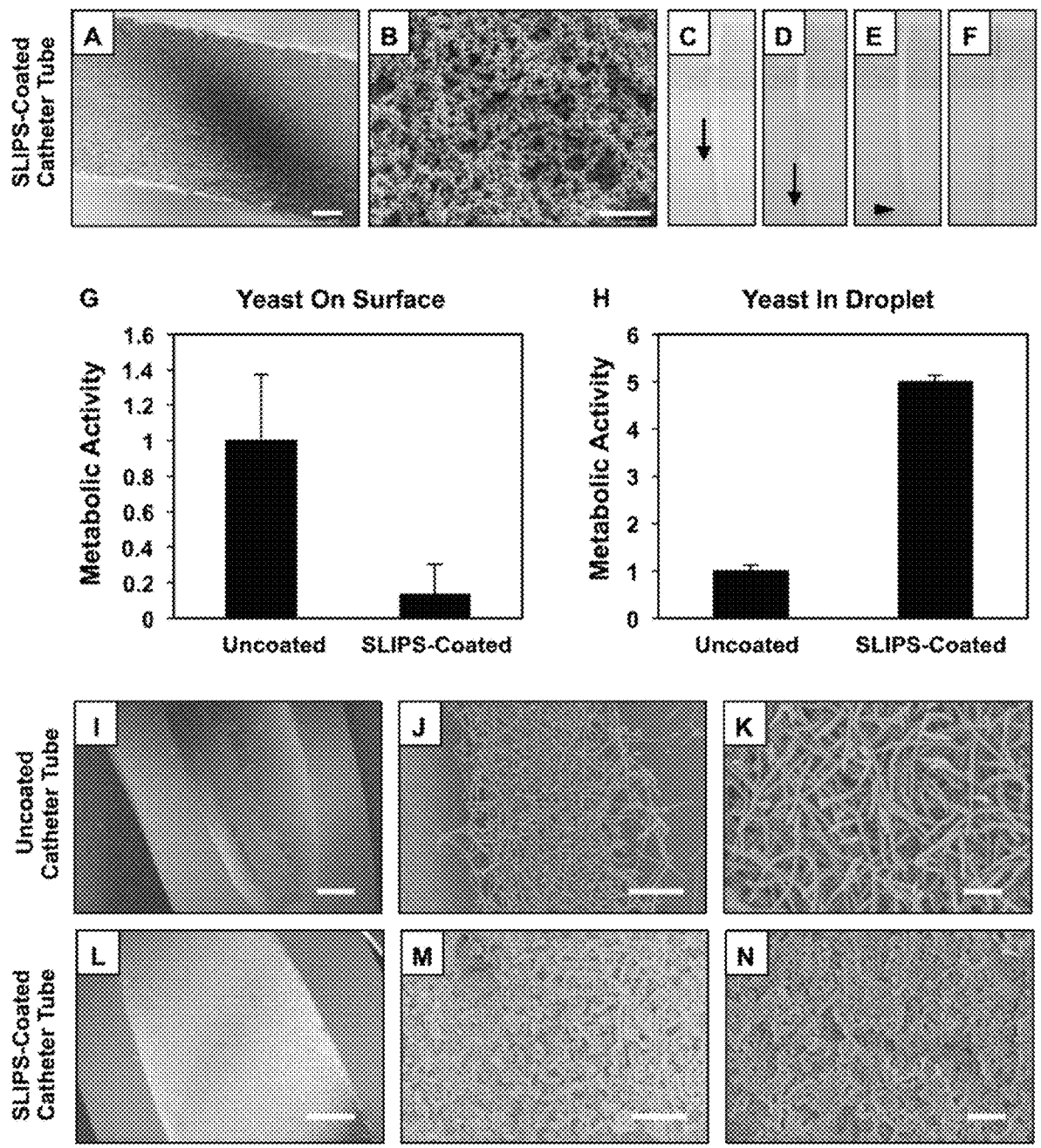
FIG. 4: (A-B) Lower- and higher-magnification SEM images showing the surfaces of porous polymer multilayers fabricated on the inner surfaces of catheter tubes prior to the infusion of silicone oil; tube segments were sliced longitudinally prior to imaging (scale bar in A=100 µm; scale bar in B=2 µm). (C-E) Digital images showing the sliding of aliquots of aqueous TMR (5 µL) inside SLIPS-coated catheter tubes tilted at an angle of 10°. (F) Digital image showing an aliquot of aqueous TMR at the top end of a bare catheter tube. (G-H) Plots showing the quantified metabolic activity of C. albicans associated with the surfaces (G) of bare and SLIPS-coated catheter tubes and in droplets of yeast inocula (H) collected from bare and SLIPS-coated catheter tubes after 4 hours of incubation. Error bars represent standard deviation. (I-N) Lower- and higher-magnification SEM images of bare (I-K) and SLIPS-coated (L-N) catheter tubes after inoculation with suspensions of C. albicans for 4 hours; samples were prepared by conventional critical-point drying and tubes were sliced longitudinally prior to imaging. Scale bars in panels I,L; panels J,M and panels K,N are 200 µm, 50 µm, and 10 µm, respectively.

A series of experiments was also performed to characterize the ability of SLIPS to prevent C. albicans adhesion and biofilm formation on the inner surfaces of narrow diameter polymer-based catheter tubes. FIG. 4 (A-B) shows low- and high-magnification SEM images of micro/nanoporous PEI/PVDMA multilayers on the inner surfaces of polyethylene tubes ~850 µm in diameter (images were acquired prior to the infusion of silicone oil). The images in panels C-E of FIG. 4 demonstrate that the inner surfaces of these tubes become slippery when infused with oil. These images show a 5 µL aliquot of an aqueous solution of the red dye tetramethylrhodamine (TMR) slipping rapidly through a SLIPS-coated catheter tube held at a 10° angle (FIG. 4 (F)) shows an image of a similar experiment conducted using a bare, uncoated tube; the liquid in this case remains pinned at the top of the tube and does not pass through the tube under these conditions).

Figure 12:
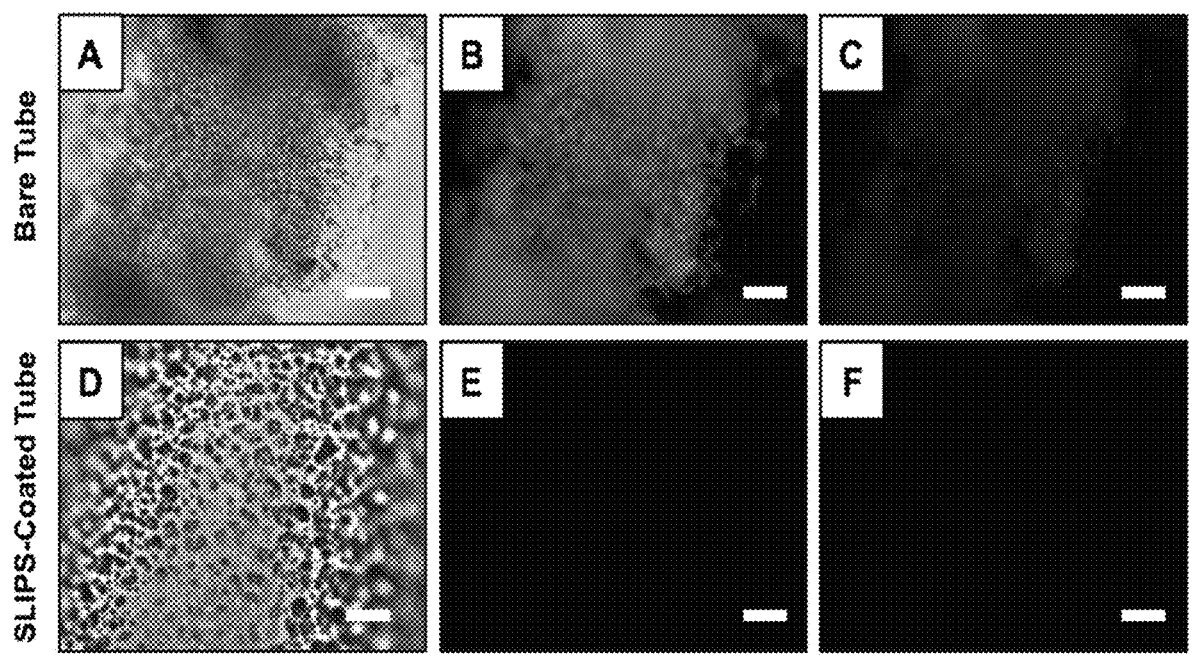
FIG. 12: Representative bright-field (A,D) and fluorescence (B-C, E-F) microscopy images showing the inner surfaces of bare and SLIPS-coated PTFE tubes incubated with C. albicans inocula for 4 hours. Samples were stained with FUN-1 fluorescent dye prior to imaging; green indicates cytoplasmic staining and red indicates intravacuolar structures in live cells. The textures observed in panel D arise from the features of the polymer coating and, as indicated by the results in panels E-F, do not arise from the presence of biofilm. Scale bars are 100 µm.

Segments of uncoated and SLIPS-coated catheter tubes were filled with C. albicans inocula, incubated at 37° C. for 4 hours, and then used SEM to visualize and characterize the amounts and types of cells adhered to both types of tubes. Hyphal and pseudohyphal C. albicans cells were observed on the surfaces of bare control tubes (FIG. 4 (I-K)), as expected in the early stages of biofilm formation. The surfaces of SLIPS-coated catheters were largely devoid of C. albicans cells (FIG. 4 (L-N)); the roughness and texture apparent in panels M and N are again features associated with the polymer multilayer matrix; e.g., see FIG. 4 (A); FIG. 12 shows representative fluorescence microscopy images of FUN-1-stained bare or SLIPS-coated samples).

The metabolic activity of cells associated with SLIPS-coated surfaces was also ~85% lower than that measured in bare, uncoated catheter tubes (as determined by an XTT assay; FIG. 4 (G)). Furthermore, it was estimated that ~5 times more planktonic cells remained in the liquid media contained inside SLIPS-coated tubes in these experiments (FIG. 4 (H)) compared to the media inside bare, uncoated tubes that permit or promote cell attachment. This result is to be expected in view of the anti-fouling nature of the SLIPS-coated tubes (to which suspended, planktonic cells cannot attach). This result also illustrates, however, one potential limitation of SLIPS in certain contexts—namely that SLIPS can prevent or reduce microbial cell attachment and biofilm formation on the surfaces to which they are applied, but can themselves do little to prevent the growth and proliferation of planktonic C. albicans cells and other potentially harmful pathogens in surrounding aqueous environments.

The results above also demonstrate that the anti-fouling nature of these SLIPS is not perfect and, in particular, that fungal adhesion and biofilm formation can occur over short periods in locations (e.g., edges and corners) where slippery character may be compromised. It is considered likely that this latter issue could be addressed through the application of SLIPS to substrates that do not contain sharp edges, such as the glass slides used in several of the above experiments. In the sections below, however, a controlled release approach is described for new multi-functional SLIPS that could help address these broader issues and expand the potential utility of these slippery surfaces.

Multilayer-Based SLIPS Prevent Adhesion & Colonization by Bacteria & Mammalian Cells.

The ability of silicone oil-infused, PEI/PVDMA-based SLIPS-coated surfaces to resist attachment and fouling by common bacterial pathogens and mammalian cells was also investigated. For these experiments, SLIPS-coated glass substrates and bare glass slides in suspensions of one Gram-negative (P. aeruginosa) and two Gram-positive (E. coli and S. aureus) species of bacteria were incubated for 24 hours at 37° C. All surfaces were then removed from solution and stained using a SYTO-9 biofilm staining solution to identify the presence of bacterial biofilms using fluorescence microscopy.

Figure 5:
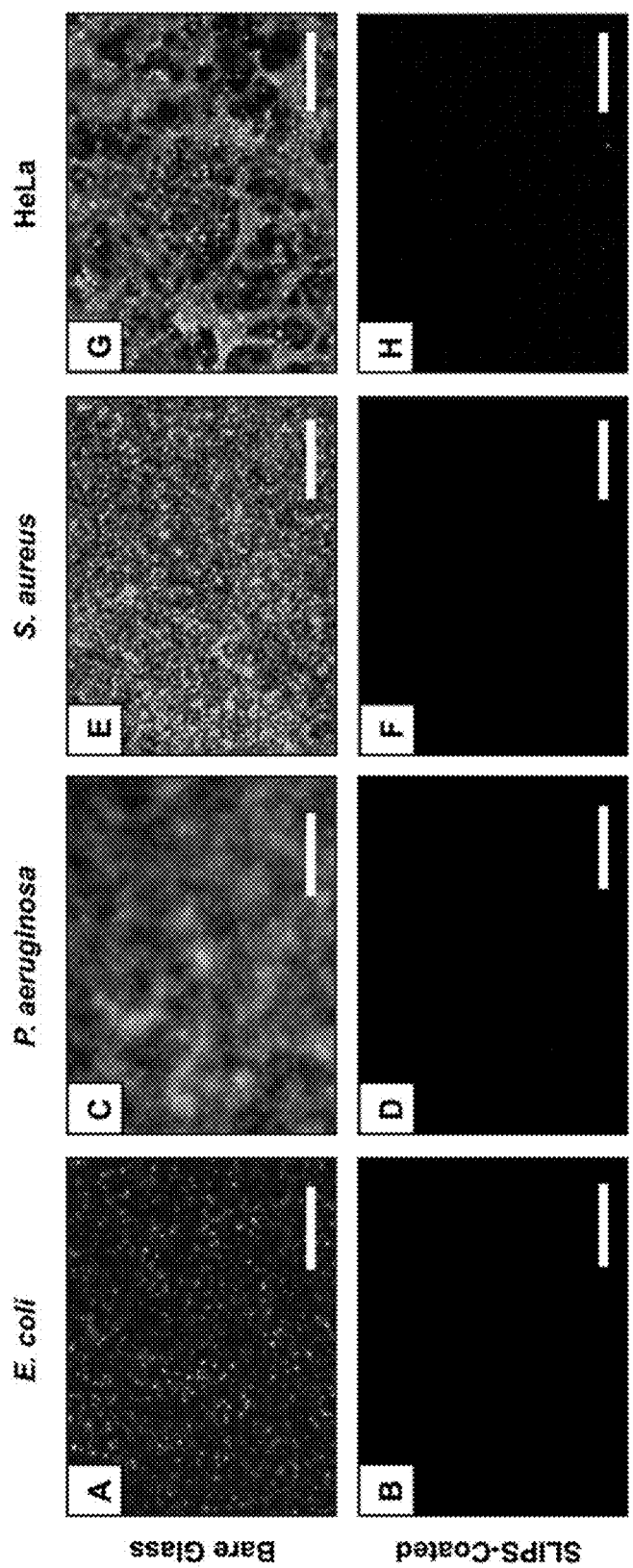
FIG. 5: (A-F) Fluorescence microscopy images of the surfaces of bare glass and SLIPS-coated glass substrates after incubation in suspensions of E. coli (A-B), P. aeruginosa (CD), and S. aureus (E-F) for 24 hours; samples were stained with a SYTO-9 green fluorescent nucleic acid stain prior to imaging. (G-H) Fluorescence microscopy images of bare glass and SLIPS-coated glass substrates after incubation with mammalian HeLa cells for 72 hours; samples were stained with calcein-AM prior to imaging. Scale bars are 100 µm.

The images in FIG. 5 (A-F) clearly indicate the presence of adherent E. coli and dense biofilms of P. aeruginosa and S. aureus on bare glass substrates (FIG. 5 (A,C,E)). These images also reveal the lack of bacterial colonization and biofilm formation on SLIPS-coated substrates (FIG. 5 (B,D, F)). Finally, FIG. 5 (G-H) show images of SLIPS-coated and bare glass surfaces after incubation with HeLa cells, a human cervical carcinoma cell line widely used as a model in biomedical research, at 37° C. for 72 hours (cells were stained using a calcein AM fluorescent cell stain prior to imaging).

Figure 13:
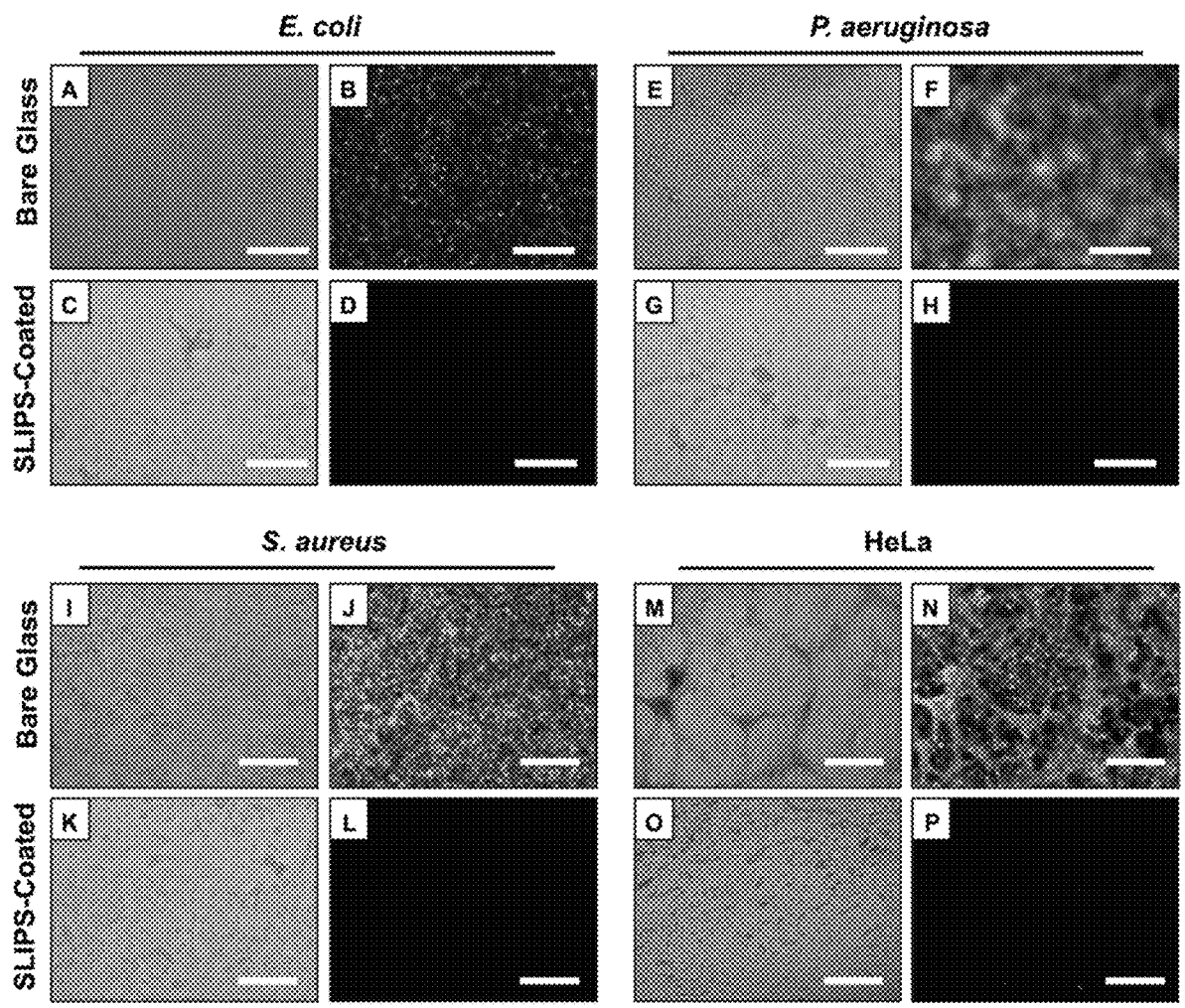
FIG. 13: (A-P) Representative bright-field and fluorescence microscopy images showing bare glass and SLIPS-coated glass substrates incubated in the presence of E. coli, P. aeruginosa, S. aureus, or mammalian HeLa cells. Scale bars are 100 µm. Films were incubated in the presence of bacteria (A-L) for 24 hours and then treated with SYTO-9 green fluorescent nucleic acid stain prior to imaging. Films were incubated in the presence of mammalian cells (M-P) for 72 hours and stained with calcein-AM prior to imaging.

The fluorescence microscopy images in FIG. 5 (G-H) demonstrate that SLIPS coatings can also substantially prevent attachment and fouling by this mammalian cell line. FIG. 13 shows additional representative images associated with these experiments. Overall, these results demonstrate that these multilayer-based SLIPS coatings can prevent surface fouling by fungal, bacterial, and mammalian cells under a range of different conditions and time scales.

Example 3—Effects of SLIPS Material on Planktonic Cells

SLIPS Loaded with Antimicrobial Agents Prevent Fouling and Kill Planktonic Cells.

One guiding hypothesis of the work described herein is that the infused oil phases of these multilayer-based SLIPS can be used to host and sustain the release of small-molecule antimicrobial agents. It is asserted that if antimicrobial agents are incorporated without degrading the inherent slippery character of these surfaces, the release of these agents into surrounding liquid media could kill planktonic cells and further prevent or reduce the likelihood of biofilm growth.

Figure 6:
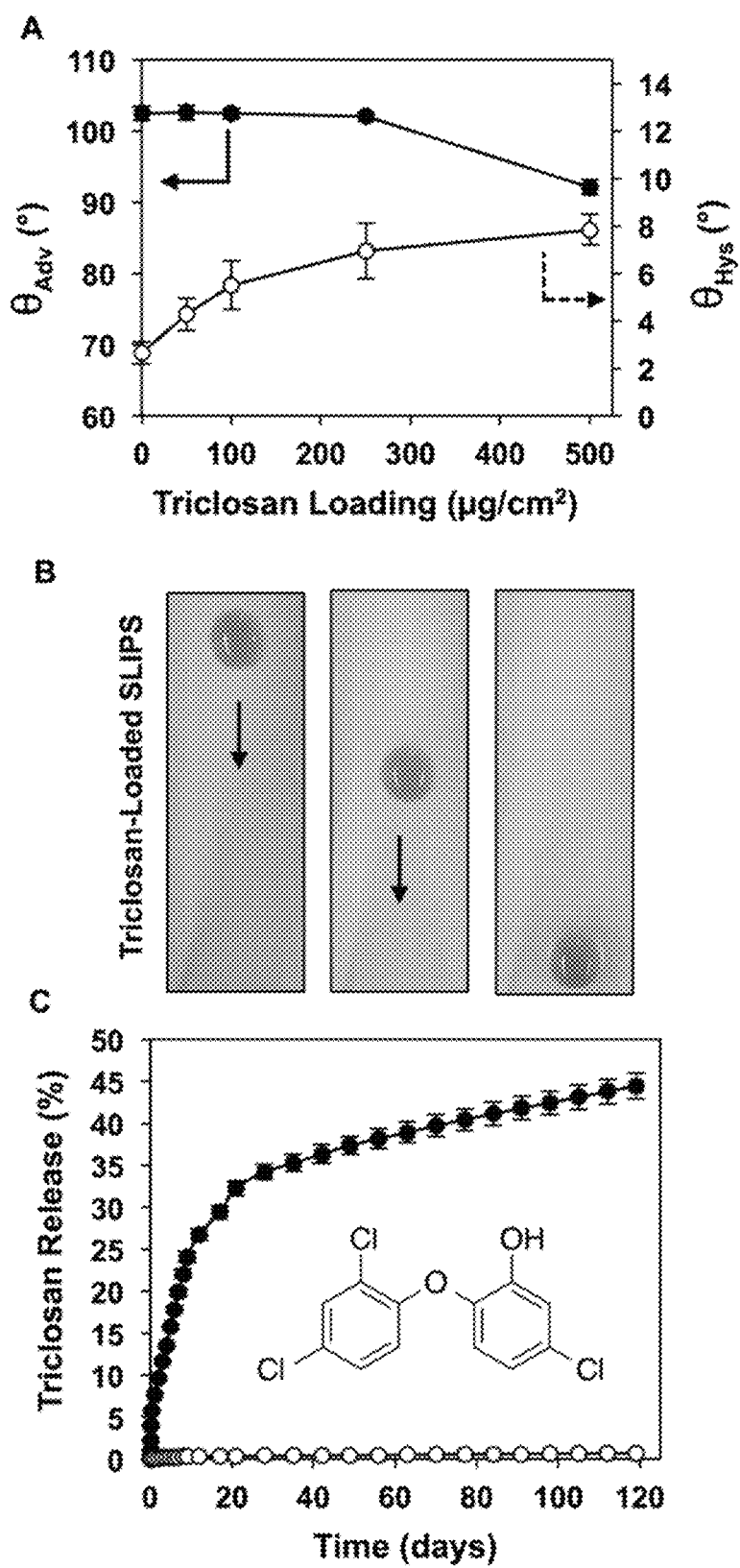
FIG. 6: (A) Plot showing the advancing water contact angles, θadv, and contact angle hystereses, θhys, of water droplets (8 µL) on SLIPS loaded with triclosan (at levels ranging from 0 µg/cm$^2$ to 500 µg/cm$^2$). (B) Digital pictures, acquired from a top-down perspective, showing the sliding of a droplet of aqueous TMR (15 µL) on a triclosan-loaded SLIP (loading=500 µg/cm$^2$; tilt angle=10°). (C) Plot showing the release of triclosan from triclosan-loaded SLIPS (closed circles; loading=500 µg/cm$^2$) upon incubation in PBS buffer at 37° C.; open circles correspond to the release profile of otherwise identical films not loaded with triclosan; the inset of panel C shows the molecular structure of triclosan. Error bars represent standard deviation.

To explore the feasibility of this approach and establish proof-of-concept, experiments were performed using silicone oil-infused SLIPS and triclosan, a model broad-spectrum antimicrobial agent that can kill both fungal and bacterial cells (the molecular structure of triclosan is shown in the inset of FIG. 6 (C)). Triclosan is soluble in silicone oil and thus permits the facile design of triclosan-loaded SLIPS by direct infusion of triclosan/silicone oil solutions into nanoporous multilayer matrices. In this study, however, an alternative approach to loading was adopted that involves the solvent-assisted loading of triclosan into the nanoporous multilayers prior to infusion with silicone oil (see discussion above for additional details related to materials and methods used in these experiments).

This technically straightforward, solvent-assisted method was used for three reasons: (i) it allows precise control over the amount of triclosan (or any other anti-microbial agent) loaded, (ii) it permits the loading of agents into SLIPS at concentrations that far exceed their solubility in the oil phase and, perhaps most notably, (iii) it has the potential to promote more gradual and sustained release. Without being bound by theory, it is believed the sustained release involves the partitioning of triclosan from the polymer matrix into the oil and from the oil into the surrounding aqueous phase, which provided a more sustained release than a material in which all of the loaded agent is initially present in the oil phase.

FIG. 6 shows the results of experiments using triclosan-loaded SLIPS prepared by the pre-oil-infusion treatment of porous PEI/PVDMA multilayers with solutions of triclosan in acetone. As shown in FIG. 6 (A), the loading of triclosan into the polymer matrix did not have a substantial impact on the advancing water contact angle ($\theta_{adv}$) for loadings of triclosan up to 250 µg/cm² ($\theta_{adv}$ ~103°), and reduced it only slightly at loadings of 500 µg/cm² ($\theta_{adv}$ ~93°). The contact angle hysteresis ($\theta_{hys}$) of these surfaces increased gradually over a small range (from ~3° to ~8°) as triclosan loading was increased from 0 µg/cm² to 500 µg/cm² (FIG. 6 (A)). This combination of features allows triclosan to be incorporated into oil-infused SLIPS that maintain their slippery properties, as demonstrated by sliding of a 15 µL droplet of an aqueous TMR solution on the triclosan-loaded SLIPS-coated glass slide shown in FIG. 6 (B) (tilt angle=10°; loading=500 µg/cm²).

FIG. 6 (C) shows the cumulative amount of triclosan released into solution over time for triclosan-loaded SLIPS submerged and incubated in PBS buffer at 37° C. (closed circles; open circles correspond to the release profile of otherwise identical films not loaded with triclosan). Approximately 30% of the loaded triclosan was released over the first 20 days of incubation, with an additional ~15% of the triclosan released over an additional 100 days. This profile is consistent with an initial burst release phase followed by a slower and more sustained phase of release, and is also consistent with concentration dependent diffusion processes involving the gradual partitioning of triclosan from the polymer matrix into the oil phase and into solution.

These results demonstrate that this loading approach can be used to design SLIPS that promote the sustained release of an antimicrobial agent for a period of at least 4 months. It is noted that only ~45% of the initially loaded triclosan was released over this 4-month period. The results shown in FIG. 6 (C) suggest that release would likely continue occur over a substantially longer period, but the release was not monitored for longer than 4 months as part of this proof-of-concept study.

Figure 7:
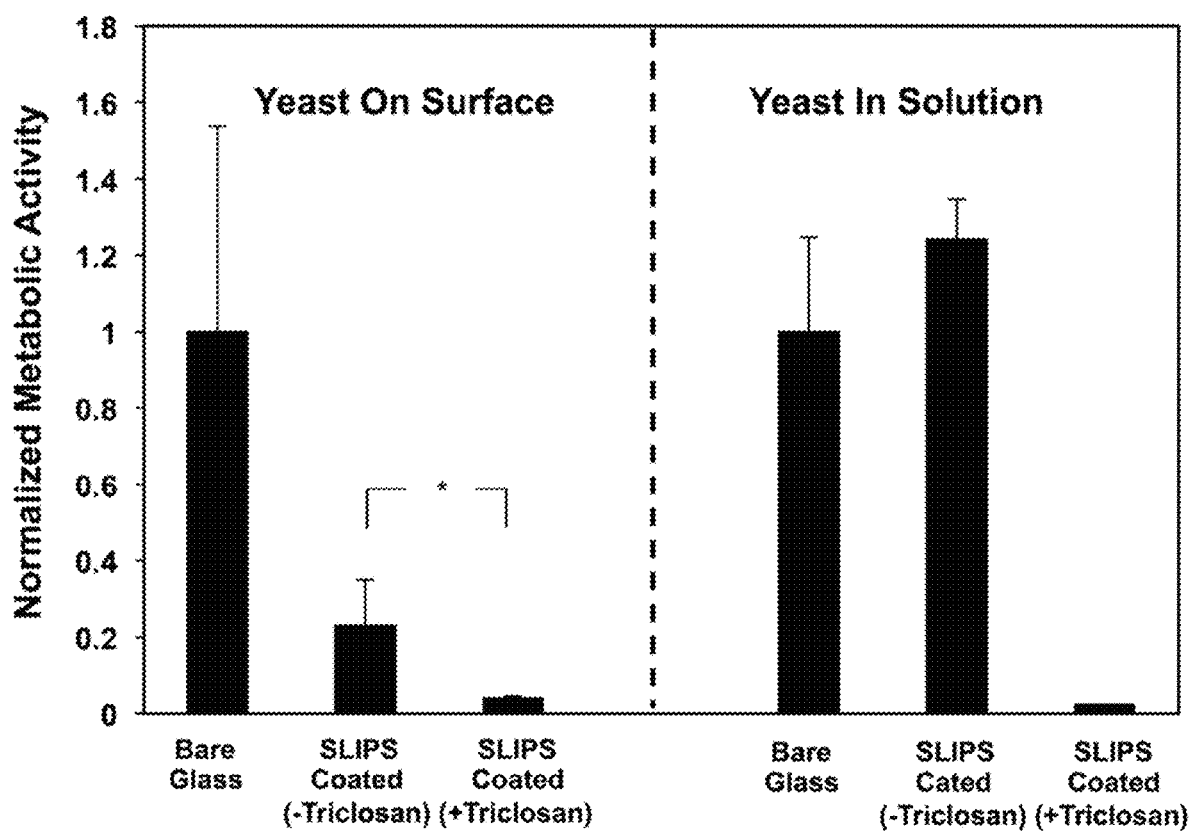
FIG. 7: Plot showing the quantified metabolic activity of C. albicans associated with the surfaces (left) of bare glass, SLIPS-coated glass, and triclosan-loaded SLIPS-coated glass and (right) the metabolic activity of planktonic yeast growing in the surrounding medium; metabolic activities were quantified using an XTT assay; all data are normalized with respect to the metabolic activities measured for experiments using bare glass substrates. Substrates were incubated with C. albicans inoculum for 24 hours, removed from wells, and the surfaces and remaining cell suspensions were quantified separately. Error bars represent standard deviation; *indicates p<0.05 by a two-tailed T-test.
Figure 14:
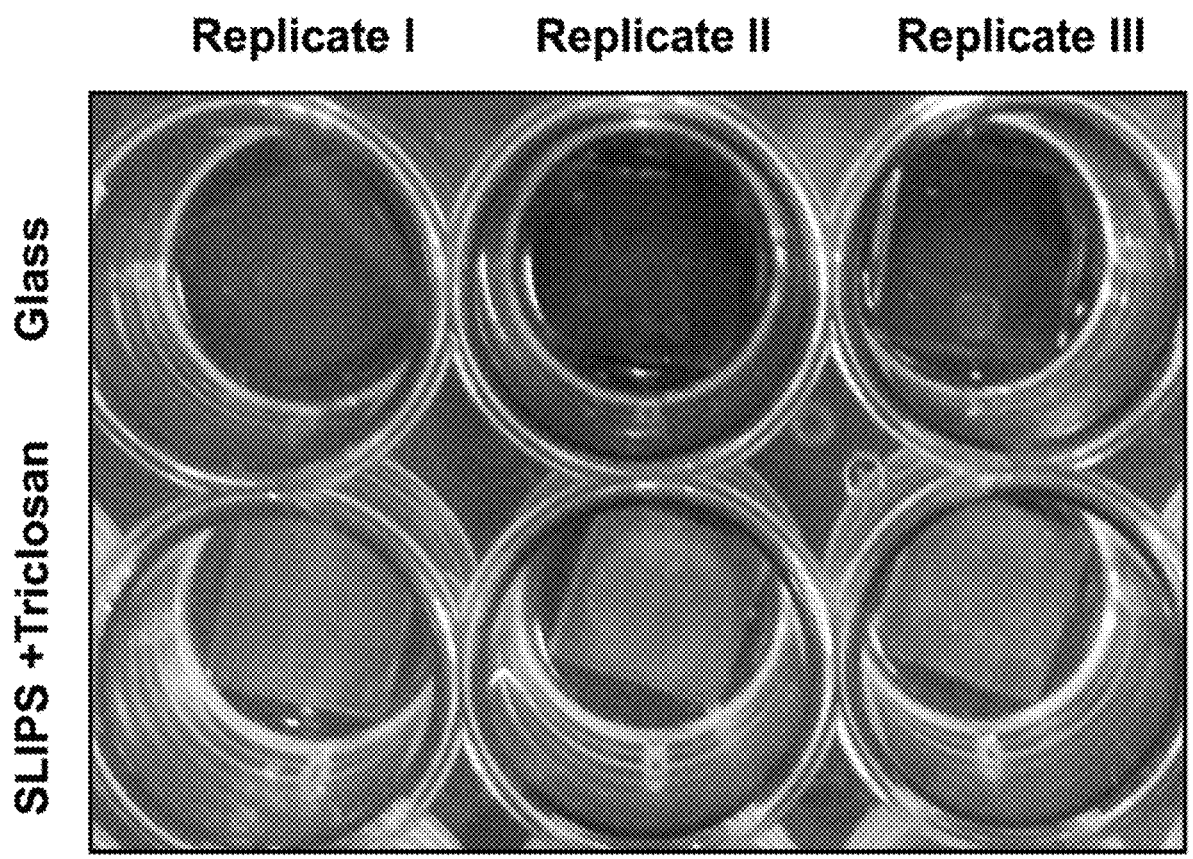
FIG. 14: Digital photographs providing a visual indication of relative levels of metabolic activity exhibited by C. albicans biofilms formed in the presence of bare glass (top) or triclosan-loaded, SLIPS-coated glass substrates (as determined by an XTT assay; three replicates are shown). The intensity of the orange color (shown here in grey scale) indicates relative levels of metabolic activity.

To determine whether the triclosan released from these SLIPS could be released in amounts sufficient to kill planktonic C. albicans and inhibit biofilm formation, triclosan-loaded SLIPS-coated glass slides were immersed in C. albicans inocula and incubated at 37° C. for 24 hours (SLIPS-coated glass substrates without triclosan and bare glass substrates were used as controls). The amounts of metabolically active yeast present both (i) on the surfaces of the substrates and (ii) in the surrounding media in the wells containing the substrates were quantified separately using the XTT assay; the quantitative results of these studies are shown in FIG. 7 (representative qualitative visual results are also shown in FIG. 14).

Triclosan-loaded SLIPS exhibited substantial and significant reductions in the amounts of C. albicans present both in solution and on their surfaces relative to SLIPS without triclosan and bare glass substrates. In particular, the nearly complete lack of metabolically active C. albicans present in solution when triclosan-loaded SLIPS were used (FIG. 7; right) demonstrates that the release of triclosan occurred in amounts sufficient to kill nearly all of the planktonic C. albicans cells present in the liquid media.

The loading of triclosan also yielded significant reductions in the amount of metabolically active yeast associated with the surfaces of the SLIPS (FIG. 7; left), a result that is likely a direct outcome of the ability of those SLIPS to substantially reduce the number of viable planktonic C. albicans cells in their surrounding environments. Because triclosan-loaded SLIPS release triclosan for prolonged periods, a multiple challenge experiment was performed similar to that described above as well as a second, longer-term incubation experiment to determine whether triclosan-loaded SLIPS could exhibit enhanced resistance to C. albicans colonization under longer and more challenging conditions.

Figure 8:
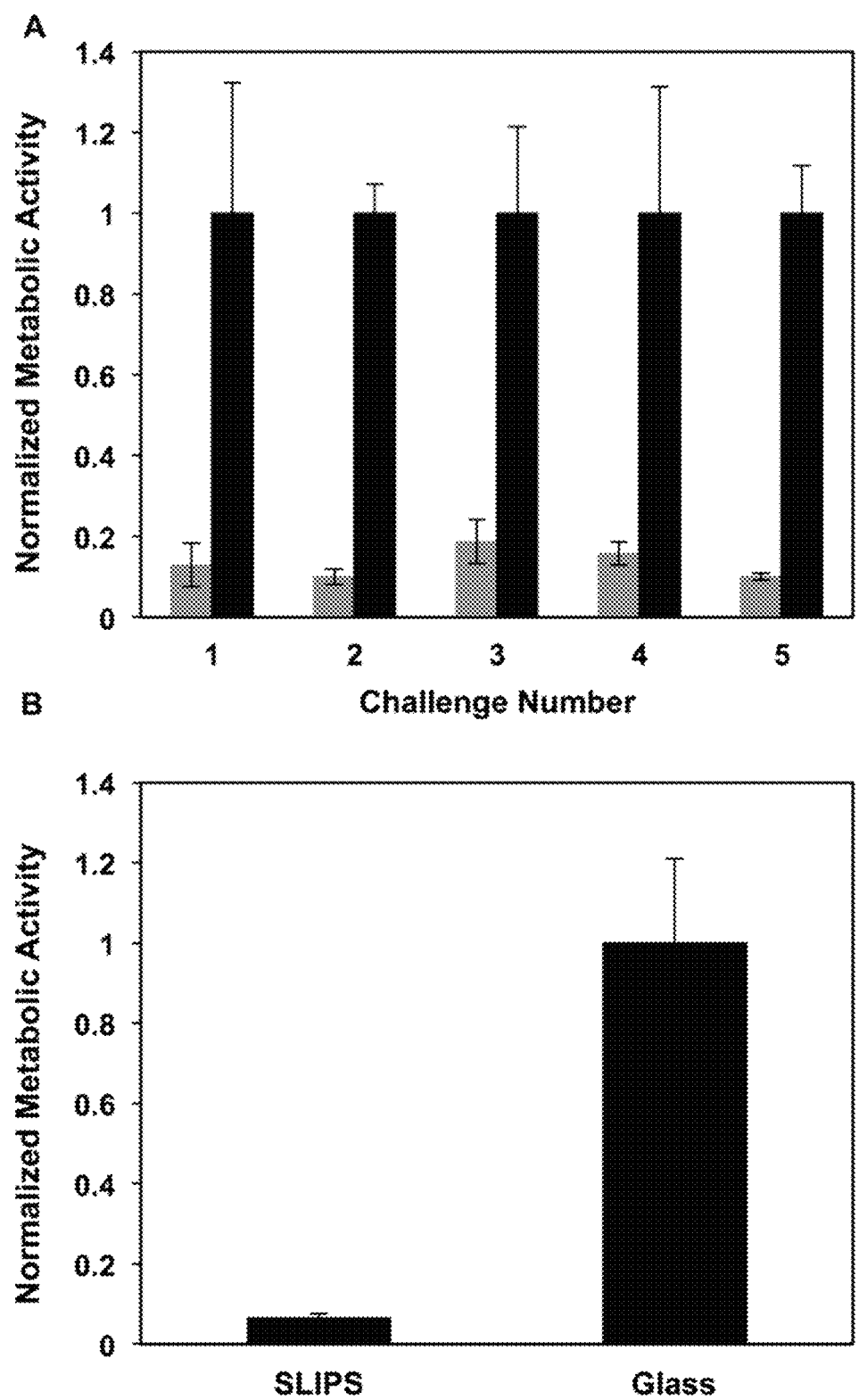
FIG. 8: (A) Plot showing the quantified metabolic activity of C. albicans associated with the surfaces of bare glass (black) and triclosan-loaded SLIPS (grey) after each of five consecutive 24-hour challenges in C. albicans inoculum, as determined using an XTT assay. (B) Plot showing the quantified metabolic activity of C. albicans associated with the surfaces of bare glass and triclosan-loaded SLIPS after continuous incubation in C. albicans inoculum for 7 days. Error bars represent standard deviation.

For multiple challenge experiments, triclosan-loaded SLIPS (and control bare glass substrates) were subjected to five sequential 24-hour immersions in wells containing freshly prepared C. albicans inocula. As shown in FIG. 8 (A), SLIPS loaded with triclosan were observed to prevent biofilm formation on these surfaces (it was also observed that almost no viable cells were in solution at the remainder of each 24-hour challenge, consistent with the results shown in FIG. 7; data for multiple challenges not shown here).

For the long-term antifungal experiment, substrates were placed in wells containing C. albicans inoculum and removed at the end of one week (with one quarter of the volume of the culture media in the wells gently replaced every two days). Triclosan-loaded SLIPS were observed to have substantially reduced amounts of metabolically active C. albicans cells associated with their surfaces after this extended period of incubation (compared to glass controls; FIG. 8 (B)).

Figure 9:
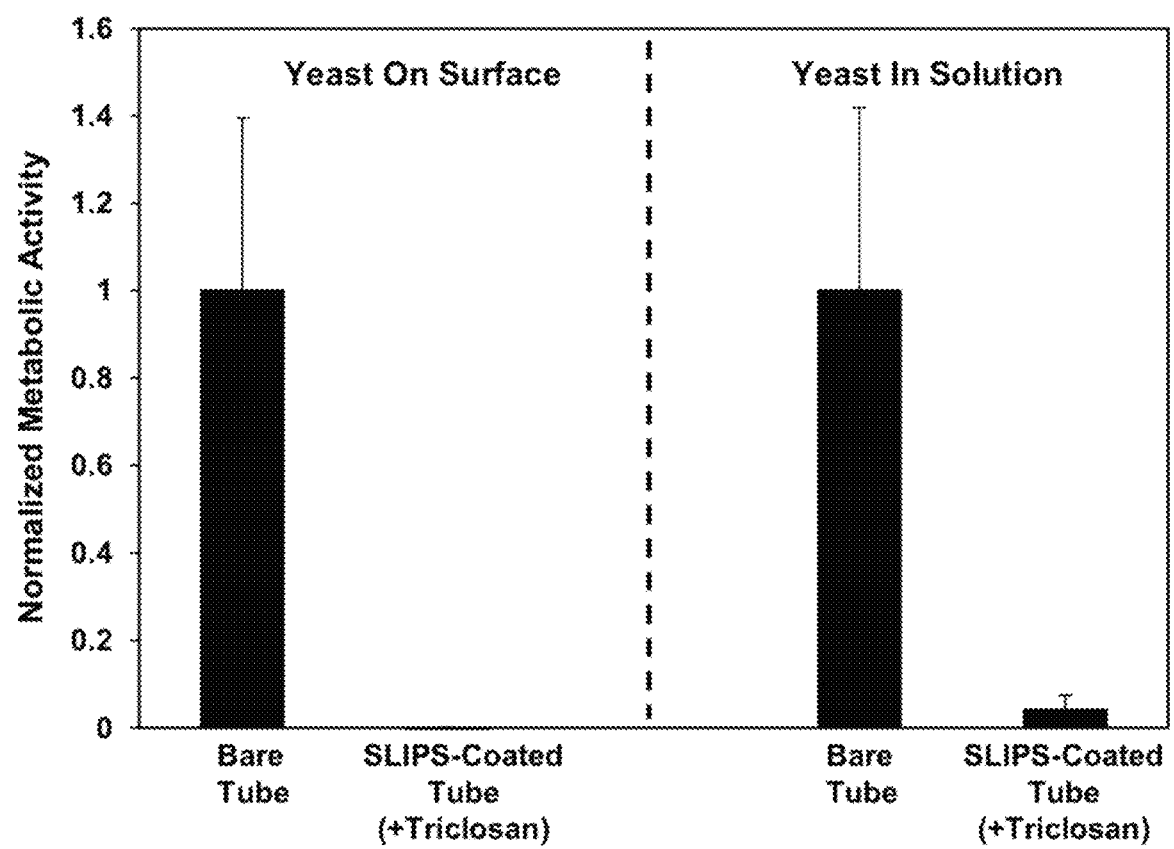
FIG. 9: Plot showing the quantified metabolic activity of C. albicans associated with the surfaces (left) of bare catheter tubes and triclosan-loaded SLIPS-coated catheter tubes and (right) the metabolic activity of planktonic cells growing in the surrounding intraluminal medium; metabolic activities were quantified using an XTT assay; all data are normalized with respect to the metabolic activities measured for experiments using bare catheter tubes. Substrates were incubated with C. albicans inoculum for 4 hours, and the surfaces and remaining cell suspensions were quantified separately. Error bars represent standard deviation.

In a final series of experiments, triclosan-loaded SLIPS were also fabricated inside catheter tubes. As shown in FIG. 9, the incorporation of triclosan also resulted in substantial reductions in both biofilms and viable cells in the intraluminal solutions of media incubated in these tubes.

When combined, the results of these experiments demonstrate that these multifunctional, triclosan-loaded SLIPS can exert influences in important ways that extend beyond those that rely on direct interactions with cells at their slippery surfaces. These results also demonstrate that this approach to killing planktonic microbial cells in surrounding media can improve the anti-fouling properties of these materials. Because triclosan is a broad-spectrum antimicrobial agent that also exhibits substantial activity against bacteria, it is anticipated that the approach to the loading and release of triclosan described above for the design of SLIPS that kill planktonic fungal cells could also be used to improve the antibacterial properties of these coatings. This approach thus has the potential to be general and provide broader benefits in biomedical contexts by eliminating both planktonic yeast and bacterial cells that could promote downstream infections or produce harmful toxins (e.g., hemolysin, toxic shock syndrome toxin, etc.) through processes that are independent of problems associated with the simple attachment of cells or the formation of biofilms on surfaces.

Summary and Conclusions.

The above examples demonstrate an approach to the design of slippery liquid-infused porous surfaces (SLIPS) that can both strongly prevent surface fouling and effectively kill microbial pathogens in surrounding media. This approach addresses a current limitation of SLIPS-based coatings reported by other groups, which can prevent fouling by microorganisms on the surfaces to which they are applied, but cannot prevent the proliferation of or kill nearby non-adherent cells that could colonize nearby surfaces or engage in other behaviors that could lead to infections or other associated burdens. The multi-functional SLIPS reported here address these important issues and thus have the potential to significantly expand the utility and effectiveness of these anti-fouling surfaces in a range of biomedical, industrial, and commercial contexts.

These results demonstrate that SLIPS fabricated by the infusion of silicone oil into nanoporous polymer multilayers can prevent short- and longer-term colonization and the formation of biofilms by the prevalent and opportunistic fungal pathogen *C. albicans*. These results also demonstrate that the porous polymer and hydrophobic oil phases comprising these materials can be exploited to load and then sustain the release of the hydrophobic and broad-spectrum antimicrobial agent triclosan into surrounding media. Using the silicone oil-infused PEI/PVDMA model SLIPS system reported here, these results demonstrate that the release of triclosan into surrounding aqueous media can be sustained for extended periods (up to at least 4 months, the longest period investigated in this proof-of-concept study). This approach improves both the inherent anti-fouling properties of these slippery surfaces (e.g., by reducing surface-associated fungi and biofilm growth that can occur at defects present at the edges of planar substrates) and, importantly, endows these coatings with the ability to efficiently kill planktonic *C. albicans*.

Finally, these results demonstrate that these SLIPS coatings can also prevent surface fouling by common bacterial pathogens and a model mammalian cell line and that they can be fabricated on the insides of flexible catheter tubes, suggesting one potential applied biomedical context in which the multi-functionality of this dual-action approach may prove useful. It should be noted, however, that the general strategy reported here for the loading and release of small-molecule agents into slippery surfaces is not likely to be limited to the model system reported here, and has the potential to be general. Provided that the properties of the porous matrix and the infused oil are chosen appropriately, for example, this general approach could be used to host and control the rates of release of a broad range of functional agents into aqueous environments or other surrounding media. As such, the materials, strategies, and concepts reported here have the potential to open the door to many new applications of this new class of slippery liquid-infused materials.

Example 4—Fabrication of SLIPS Material with Quorum Sensing Modulators

Embodiments of the present invention seek to further develop the potential of SLIPS as reservoirs for the controlled release of active agents, with a focus on the design of multifunctional and chemical-eluting SLIPS capable of attenuating the colonization and virulence of planktonic bacteria through non-biocidal means (e.g., by sustaining the release of active agents that do not necessarily kill bacteria, but instead attenuate virulent behaviors by targeting non-essential pathways). Such 'anti-virulence' strategies have attracted considerable interest over the past decade as the incidence of bacterial resistance has increased (see Clatworthy et al., Nat. Chem. Biol. 2007, 3, 541-548; and Allen et al. Nat. Rev. Microbiol. 2014, 12, 300-308).

One promising target for potential anti-virulence approaches is bacterial quorum sensing (QS) circuits. QS is a small molecule-based communication system used by many bacteria to coordinate the expression of group-beneficial behaviors when a threshold population density (i.e., a 'quorum') is reached (see Bassler et al., Cell 2006, 125, 237-246; Camilli et al. Science 2006, 311, 1113-1116; and Ng et al., Annu. Rev. Genet. 2009, 43, 197-222). In many common pathogens, such as the Gram-negative bacterium *Pseudomonas aeruginosa*, QS systems control the production of excreted virulence factors and the formation of biofilms, but are non-essential for cell growth—targeting these systems thus presents a basis for the development of 'non-biocidal' approaches to controlling bacterial virulence. Over the last 10 years, many potent small molecule inhibitors of QS (QSIs) that are active in *P. aeruginosa* and other pathogens, and that represent valuable chemical tools to test such anti-virulence approaches, have been developed (Eibergen et al., Chem BioChem 2015, 16, 2348-2356; Geske et al., Bioorg. Med. Chem. Lett. 2008, 18, 5978-5981; Geske et al. ChemBioChem 2008, 9, 389-400; Mattmann et al. ChemBioChem 2011, 12, 942-949; and Stacy et al., ACS Chem. Biol. 2012, 7, 1719-1728).

As part of a broader effort to develop and exploit the therapeutic potential of QSIs, strategies have been developed for the encapsulation or integration of QSIs and other anti-virulence agents into polymer-based materials or onto inorganic surfaces (Breitbach et al., Chem. Comm. 2011, 47, 370-372; Broderick et al., 2013, Adv. Healthcare Mater. 2, 993-1000; Broderick et al., Adv. Healthcare Mater. 2014, 3, 97-105; and Manna et al., 2013, Adv. Mater. 25, 6405-6409; Kratochvil et al., ACS Biomater. Sci. Eng. 2015, 1, 1039-1049.).

These past studies have yielded many different approaches to the release of anti-virulence agents, but they have relied, in large measure, on materials and tactics that do not inherently prevent biofouling (apart from the activities of the released inhibitors). The present example demonstrates that the polymer and oil phases of polymer-based SLIPS can be exploited to load and control the release of synthetic small molecules that inhibit or modulate QS in *P. aeruginosa*. It is also demonstrated that these QSIs can be loaded into SLIPS without affecting slippery or anti-fouling properties, and that the agents remain biologically active, enabling QSI-loaded SLIPS to both prevent bacterial colonization and attenuate important QS-regulated behaviors, such as the production of key excreted virulence factors, in planktonic cultures of this pathogen. These liquid-infused materials can also be designed to release multiple QSIs that target multiple different QS circuits simultaneously.

Finally, it is demonstrated that these polymer-based SLIPS, which are inherently resistant to the formation of *P. aeruginosa* biofilms on their own surfaces, can also release non-bactericidal biofilm inhibitors that confer robust protection against the formation of biofilms on other nearby and unprotected (non-SLIPS-coated) surfaces. These results suggest the basis of new non-bactericidal approaches to the design and protection of anti-fouling surfaces that circumvent critical problems associated with the use of antibiotics.

More broadly, this work also advances new approaches to the integration of controlled release strategies with SLIPS-based technologies that could improve the properties of these inherently anti-fouling, oil-infused surfaces in a range of other contexts.

Materials and General Considerations.

All chemicals were purchased from Sigma-Aldrich, unless indicated otherwise, and used without further purification. 2-Vinyl-4,4-dimethylazlactone (VDMA) was a gift from 3M Corporation, Minneapolis, Minn. Poly(2-vinyl-4, 4-dimethylazlactone) (PVDMA) was synthesized as described previously (Buck et al., Chem. Mater. 2010, 22, 6319-6327). Glass microscope slides were purchased from Fisher Scientific (Pittsburgh, Pa.). Dimethyl-2-aminobenzamidazole (DMABI), and compounds C14, E22, and V-06-018 were synthesized as previously reported (Frei et al., Angew. Chem. Int. Ed. 2012, 51, 5226-5229; Geske et al., ChemBioChem 2008, 9, 389-400; Geske et al., Bioorg. Med. Chem. Lett. 2008, 18, 5978-5981; and Muh et al., Antimicrob. Agents Chemother. 2006, 50, 3674-3679). Compressed air used to dry samples was filtered through a 0.2 µm membrane syringe filter. UV/vis measurements were made using a Beckman Coulter DU520 UV/vis spectrophotometer (Fullerton, Calif.). Fluorescence microscopy images were acquired using an Olympus IX70 microscope and analyzed using the Metavue version V7.7.8.0 software package (Molecular Devices). Log P values were calculated using Perkin Elmer ChemDraw version 13.0.0.118 (Cambridge Soft Corporation). Absorbance measurements in biological assays were made using a Biotek Synergy 2 plate reader running Gen 5 software (version 1.05).

Fabrication of Polymer Multilayers.

Prior to film fabrication, glass microscope slides were cut into 0.8 cm wide strips and scored in 1 cm long segments. Covalently crosslinked and nanoporous polymer multilayers composed of PVDMA and branched poly(ethyleneimine) (BPEI; MW 25,000), referred to from hereon as BPEI/PVDMA multilayers, were fabricated on the glass substrates using a covalent/reactive layer-by-layer assembly process, as previously described (Manna et al., Adv. Mater. 2015, 27, 3007-3012). Briefly, the substrates were submerged iteratively in the following solutions for 20 seconds each: (i) BPEI (20 mM in acetone with respect to the polymer repeat unit); (ii) two acetone rinses; (iii) PVDMA (20 mM in acetone with respect to the polymer repeat unit); (iv) two additional acetone rinses. This cycle was repeated 35 times. Polymer solution volumes were maintained with fresh acetone to compensate for evaporation and maintain polymer concentration during the dipping process. After fabrication, films were functionalized and rendered hydrophobic by immersion in a 20 mM solution of n-decylamine in THF overnight at room temperature. Functionalized films were then rinsed and dried using compressed, filtered air. Film-coated substrates were then fragmented along the pre-fabrication scores to produce 0.8 cm×1.0 cm samples.

Small Molecule Loading, Oil Infusion, and Characterization of Release.

A 10 µL aliquot of an acetone solution of a small-molecule agent (12.0 mM in compounds E22, C14, or V-06-018 for individual release experiments; 6.0 mM of both compound E22 and compound V-06-018 for dual release experiments; 15.0 mM for experiments using DMABI) was applied to the top side of a film-coated substrate, allowed to dry, and repeated on the coating on the opposite side of the substrate. Immediately prior to use, loaded films were infused with silicone oil (for melting point and boiling point apparatuses; Sigma-Aldrich) by placing a 2.25 µL droplet of oil on each side and allowing the oil to spread over the entire surface. Excess oil was removed from the surface using tissue paper. For release experiments, small-molecule-loaded and oil-infused films were incubated at 37° C. in 1.0 mL of PBS buffer (pH=7.4). At designated time points, substrates were removed from the incubation buffer and placed in fresh buffer before returning to the incubator. The release of the loaded agents into the incubation buffer was characterized using a UV/vis spectrophotometer.

Bacterial Strains and Growth Conditions.

All media and reagents for bacterial culture were purchased from commercial sources. Wild-type *P. aeruginosa* strain PAO1 was obtained from the University of Rochester. Overnight cultures of bacteria were grown in Luria-Bertani (LB) medium at 37° C. with shaking at 200 rpm. Freezer stocks of bacterial strains were maintained at −80° C. in 1:1 LB:glycerol. MOPS glutamate was prepared as described by Mellbye et al., J. Bacteriol. 2014, 196, 1155-1164. The assay medium was prepared prior to each experiment by diluting 10×MOPS buffer (500 mM MOPS, 40 mM tricine, 500 mM NaCl, 10 mM $K_2HSO_4$, 500 µM $MgCl_2$, 100 µM $CaCl_2$, 3 µM $(NH_4)_6Mo_7O_{24}$, 400 µM $H_3BO_3$, 30 µM $Co(OAc)_2$, 10 µM $CuSO_4$, 80 µM $MnSO_4$, 10 µM $ZnSO_4$, pH 7.0, filter sterilized) into sterile 18 MΩ water. To this working solution, a sterile 10× stock solution of L-glutamate (250 mM) and sterile 100× stock solutions of $K_2HPO_4$ (400 mM), $FeSO_4$ (500 µM), and $NH_4Cl$ (1.5 M) were added in appropriate amounts.

Pyocyanin Assay Protocol.

The amount of pyocyanin in *P. aeruginosa* culture supernatants was measured following the protocol of O'Loughlin et al. Proc. Natl. Acad. Sci. U.S.A 2013, 110, 17981-17986, with modifications. A 10 mL overnight culture of *P. aeruginosa* PAO1 was grown for 16 h. An inoculating culture was prepared by diluting the overnight culture 1:100 into freshly prepared MOPS glutamate medium, and 2 mL aliquots of this subculture were added to each test tube (0.5% DMSO). SLIPS-coated surfaces (sterilized by UV irradiation for 20 min in a biological safety cabinet) were placed in each tube, and the cultures were grown for 17 h at 37° C. with shaking incubation at 200 rpm. The final cell density was measured by reading absorbance at 600 nm ($OD_{600}$). Relative pyocyanin levels were measured by first pelleting 1.5 mL of well-mixed culture at 4,000×g for 10 min, transferring 200 µL of the resulting supernatant to a clear, plastic 96-well microtiter plate, and reading absorbance at 695 nm. Media background absorbance (measured from a "no bacteria" control) was subtracted, the resulting values were normalized by dividing by the final $OD_{600}$, and the data were plotted relative to an unloaded positive SLIPS control.

*P. aeruginosa* Biofilm Growth and Crystal Violet Staining Assay Protocol.

Biofilm formation by *P. aeruginosa* was quantified by crystal violet (CV) staining following the protocol of Frei et al., Angew. Chem. Int. Ed. 2012, 51, 5226-5229 with modifications. A 10 mL overnight culture of *P. aeruginosa* PAO1 was grown for 16 h. An inoculating subculture was prepared by centrifugation of the overnight culture at 4,000 g for 10 min followed by resuspension of the cell pellet in an amount of fresh M9+ medium (see Frei et al. for full details of this medium) supplemented with 5% (v/v) LB to effect a 1:10 dilution (v/v) of the overnight culture.

Glass substrates were placed into the wells of a 12-well microtiter plate (Costar 3737) and sterilized by UV irradiation for 20 min in a biological safety cabinet. Subculture was added to each well in 2 mL aliquots and the plates were incubated under static conditions at 37° C. for 24 h. Substrates were removed from the wells using forceps, gently dabbed on a paper towel to remove excess liquid, and placed in a new 12-well plate. Spent culture medium was removed from the wells by inverting the assay plate over a basin and the attached biofilm was washed once with 1 mL of PBS. The substrates and assay plate were allowed to dry in a 37° C. incubator for at least 8 h. The substrates and well bottoms were stained with 1 mL of a CV solution (0.1% CV (w/v) in 95:5 water:ethanol) for 10 min. Excess CV stain was removed by washing twice with 1 mL of water, and the substrates and plate were dried at 37° C. for at least 4 h. CV stain absorbed by the attached biofilm was quantified by re-solubilizing the stain in 1 mL (wells) or 0.5 mL (substrates) 30% (v/v) acetic acid, transferring 200 µL of this solution to a clear 96-well microtiter plate (Costar 3370), and measuring absorbance at 590 nm.

Characterization of Biofilms Using Fluorescence Microscopy.

Biofilms attached to glass substrates were imaged by fluorescence microscopy using the above biofilm growth protocol with the following modifications. After incubation, substrates were gently removed from the assay medium using forceps, washed once by dipping into PBS, and stained with SYTO 9 (Invitrogen) according to the manufacturer's protocol. Excess staining solution was removed by dabbing on a paper towel and the substrates were covered by 400 µL of PBS in a 24-well plate. Biofilms were then imaged using an Olympus IX71 fluorescence microscope.

Fabrication and Loading of QSIs into Nanoporous, Multilayer-Based SLIPS.

The SLIPS used in this study were fabricated by the infusion of silicone oil into nanoporous and covalently-crosslinked polymer multilayers fabricated by the reactive layer-by-layer assembly of poly(vinyl-4,4-dimethylazlactone) (PVDMA) and branched poly(ethyleneimine) (BPEI) on planar glass substrates. After film fabrication, these reactive multilayers were treated with n-decylamine to functionalize residual azlactones remaining in the films with hydrophobic alkyl groups (FIG. 15 (A)) and render them more chemically compatible with silicone oil. Infusion of silicone oil into the decylamine-functionalized multilayers yielded SLIPS that exhibited water droplet sliding angles of 10° in agreement with past studies.

Figure 16:
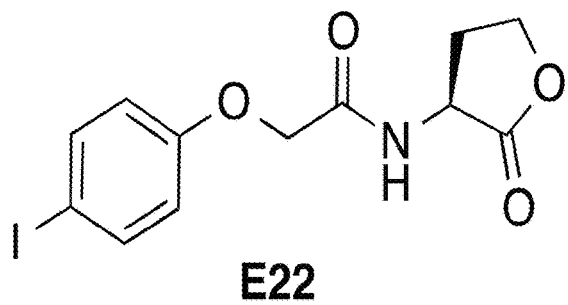
FIG. 16: Structures of the small molecule anti-virulence agents used in one embodiment of the invention.
Figure 16:
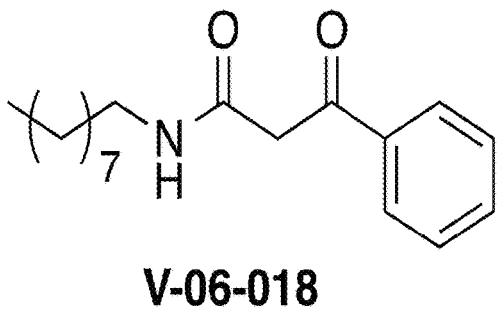
Figure 16:
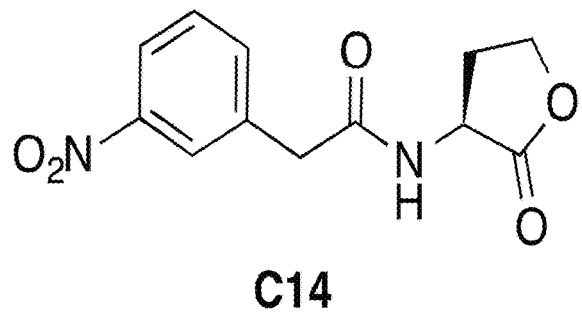
Figure 16:
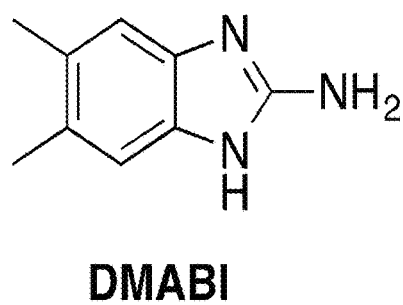

Two *P. aeruginosa* QSIs [E22 (an acyl L-homoserine lactone (AHL)-based antagonist of the RhIR QS receptor) and V-06-018 (a non-AHL-based antagonist of the LasR QS receptor)] and DMABI (a potent biofilm inhibitor that modulates QS in *P. aeruginosa* through a yet to be determined mechanism) were selected for this study (FIG. 16) because they represent some of the most potent QS modulators known.

Figure 15:
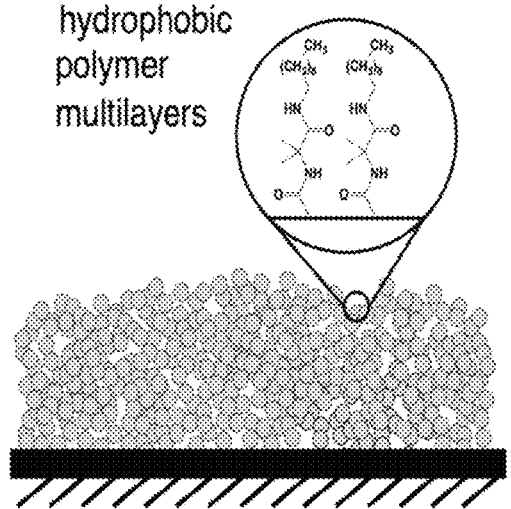
FIG. 15: Schematic illustration showing the fabrication of the controlled release SLIPS used in one embodiment of the invention. (A) Reactive and nanoporous polymer multilayers (grey) are functionalized with n-decylamine to render them hydrophobic. (B) Small molecules (diamonds) are loaded into porous multilayers by adding an acetone solution of the agents to dried films and allowing the solvent to evaporate. (C) Silicone oil is infused into the multilayers. (D) These controlled release SLIPS gradually release loaded compounds into aqueous solution when hosted in aqueous environments; these dual-action SLIPS prevent the colonization of bacteria directly on the coated surface and can also modulate the behaviors of planktonic bacteria.
Figure 15:
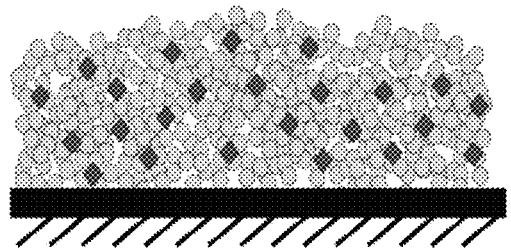
Figure 15:
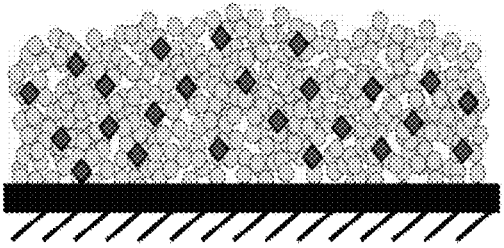
Figure 15:
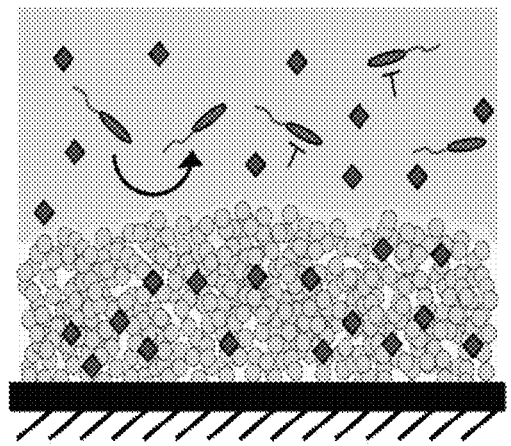

QSI- and DMABI-loaded SLIPS were prepared by applying a 10 µL droplet of a 12 mM acetone solution of QSI or a 15 mM acetone solution of DMABI to each side of the multilayer-coated substrates (prior to the infusion of oil; FIG. 15 (B)). The acetone solutions quickly wet the entirety of the nanoporous coatings and, upon evaporation, left the loaded compounds adsorbed within the multilayers. A small excess of silicone oil was then pipetted onto both sides of the compound-loaded coatings and allowed to infuse and spread across the entirety of the surface (FIG. 15 (C)). This approach to loading was adopted (e.g., as opposed to an alternative approach in which dry multilayers were infused directly with silicone oil containing dissolved compound) on the basis of our past results using triclosan, and because this approach enables more precise control over the amount of compound loaded in ways that are not restricted by the solubility of a given compound in the oil phase.

All QSI-loaded SLIPS used in this study contained 240 nmol of compound per substrate and all DMABI-loaded SLIPS contained 300 nmol of compound. It was confirmed that the loading of these small molecules did not impact the slippery properties of the resulting oil-infused multilayers by placing 10 µL droplets of water on QSI-loaded SLIPS held at a tilt angle of 10° and measuring the sliding velocities of the droplets. As revealed by the results shown in Table 1, SLIPS loaded with E22, V-06-018, DMABI, or a 1:1 ratio of both E22 and V-06-018 (at a loading of 120 nmol each) did not have a substantial impact on droplet sliding velocities.

TABLE 1

Impact of Loading on Sliding Velocities

| Loaded Compound | Slide Velocity (mm/s)[a] |
|---|---|
| None | 7.6 ± 0.3 |
| C14 | 8.4 ± 0.6 |
| E22 | 6.9 ± 0.3 |
| V-06-018 | 6.6 ± 0.6 |
| E22 + V-06-018 | 4.3 ± 0.2 |
| DMABI | 7.4 ± 0.2 |

[a]Values are the mean and standard error of six independent replicates; experiments were performed by placing droplets of water on SLIPS-coated surfaces held at angles of 10° and measuring the times required to slide a fixed distance (see Materials and Methods for details).

Characterization of the Release of QSIs and Biofilm Inhibitors from SLIPS.

QSI-loaded SLIPS were incubated in phosphate-buffered saline (PBS) to characterize the release of the imbedded QSIs into surrounding media under physiologically relevant conditions (37° C.; pH=7.4). For these studies, SLIPS loaded with compound E22 and DMABI were used because the relatively strong UV absorbance of both compounds permitted facile monitoring of release by UV/vis spectrophotometry (the absorbance of compound V-06-018 was significantly obscured by the presence of silicone oil in these experiments; release of this compound was thus not evaluated quantitatively).

Figure 17:
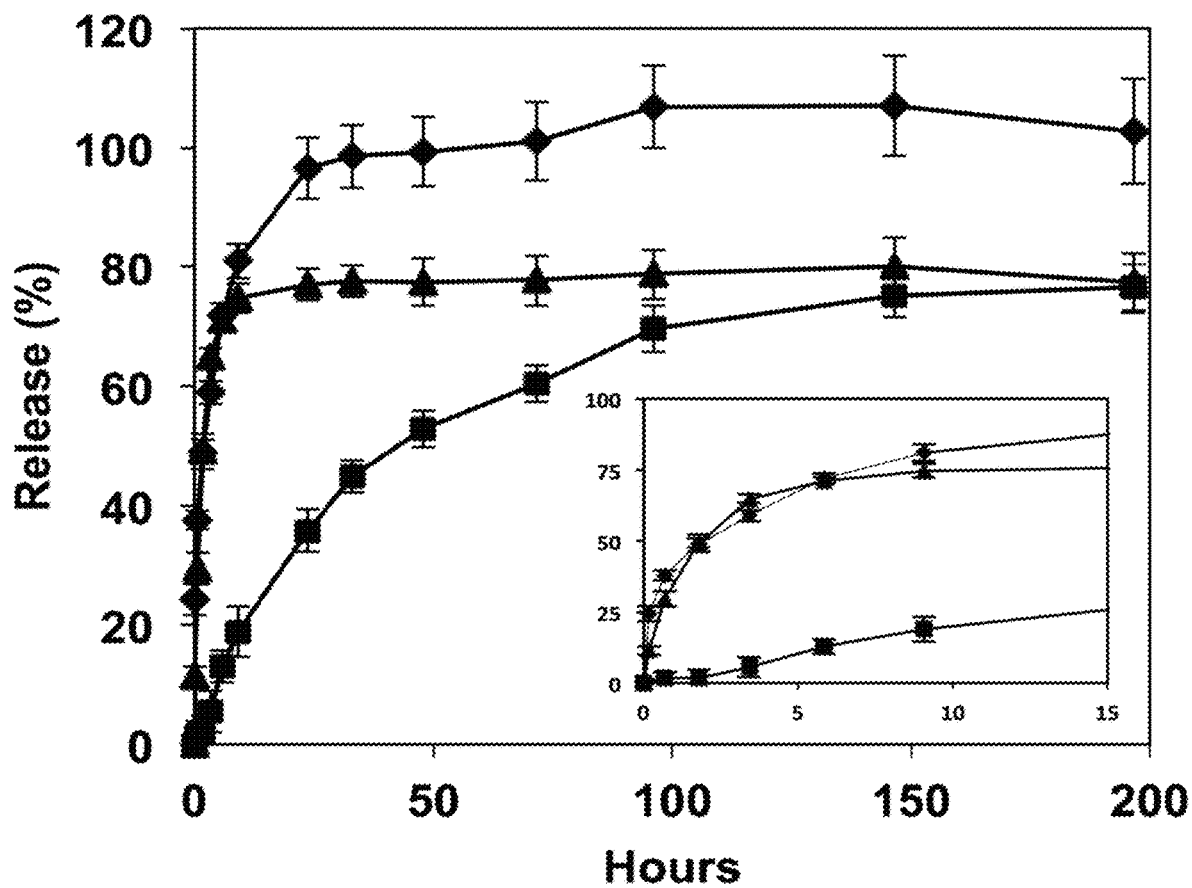
FIG. 17: Plot showing percent release versus time for the release of compounds E22 (triangles), C14 (diamonds), and DMABI (squares) from SLIPS-coated surfaces incubated in PBS buffer at 37° C. The inset shows the same results focusing specifically on the first 50 hours of release. Data points represent the mean of four replicates. The percentage of each compound released was calculated based on the total amount of compound initially loaded.

As shown in FIG. 17, compound E22 was released into surrounding buffer relatively quickly, with approximately 75% of the total amount loaded released over the first 12 hours of incubation. No further compound was released over an additional 190 hours of incubation, suggesting that ~25% of this compound remained strongly bound to the polymer matrix. Additional experiments using otherwise identical SLIPS loaded with AHL derivative C14 (structure shown in FIG. 16) revealed this more polar AHL to be released almost completely over a period of 24 hours. Finally, in contrast to the relatively rapid release exhibited by these AHL-loaded SLIPS, coatings loaded with the 2-aminobenzimidazole-based biofilm inhibitor DMABI released their contents much more slowly, with approximately 40% of the loaded compound released after the first 24 hours, and an additional ~40% released over the next 150 hours; see FIG. 17).

It is clear from these results that the structure of the loaded compounds can have a significant influence on rates and extents of release, likely a result of differences in the interactions of these compounds with the porous polymer matrix and differences in the extent to which the compounds partition into the silicone oil phase. Additional experiments are underway to better understand the factors that lead to these large differences, as well as the extent to which changes in film structure and the properties of infused oil phase can be exploited to tune the release profiles of these and other agents more broadly. The time scales and the amounts of QSIs and DMABI released by the materials reported here (FIG. 17) were more than sufficient to demonstrate robust proofs of concept in all biological studies described below.

Release of QSIs from SLIPS Attenuates *P. aeruginosa* Pyocyanin Production.

To characterize the biological activities of QSI-loaded SLIPS, production of the redox-active virulence factor pyocyanin in *P. aeruginosa* was monitored. Pyocyanin production is controlled by the QS receptors LasR and RhlR in *P. aeruginosa*, and should thus be attenuated by both V-06-018 and E22. Wild-type *P. aeruginosa* was grown in the presence of SLIPS substrates loaded with the LasR antagonist V-06-018 or the RhlR antagonist E22 (in amounts designed to yield approximately 100 µM of compound in the assay culture upon full release) and quantified pyocyanin production after 17 hours of shaking incubation.

Figure 18:
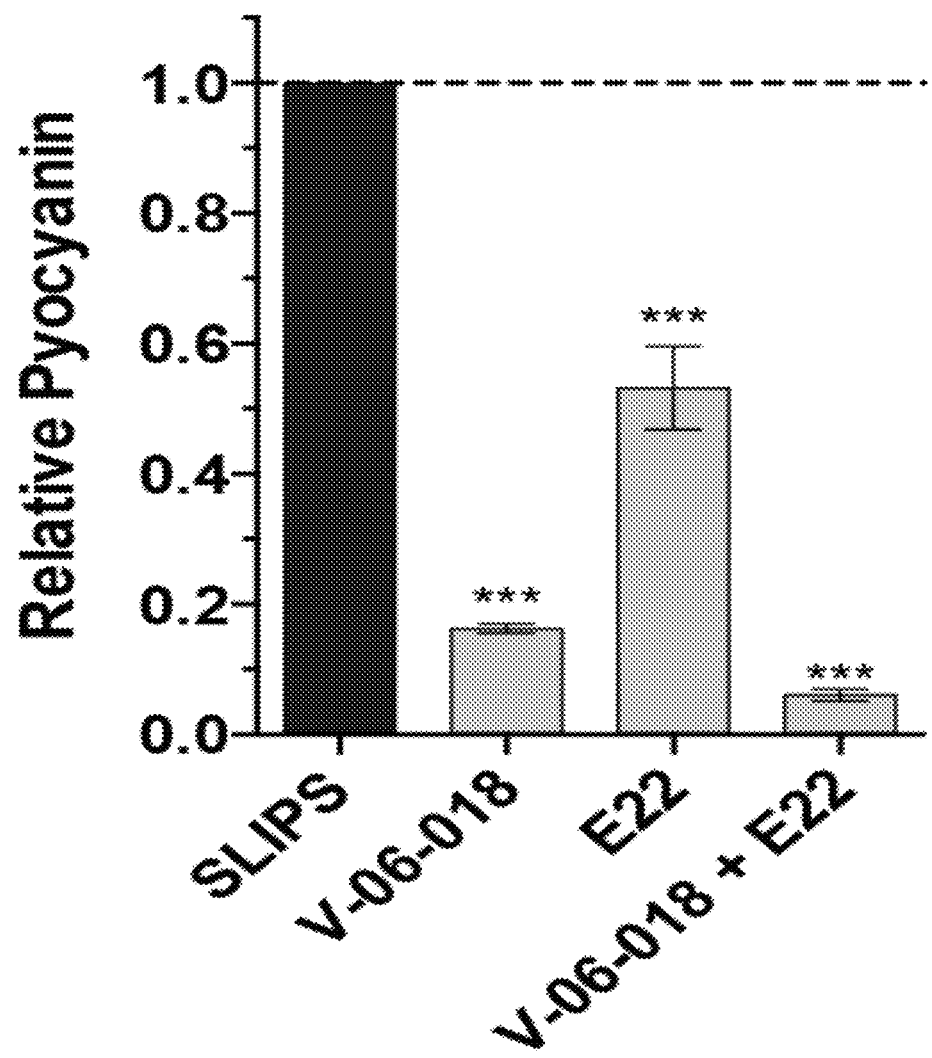
FIG. 18: Inhibition of pyocyanin production by QSIs released from SLIPS-coated surfaces. *P. aeruginosa* cultures were grown in the presence of SLIPS loaded with the indicated compounds and the final amount of pyocyanin in the culture was quantified after 17 hours of incubation. Compounds were loaded at levels estimated to give a final released concentrations of 100 µM (for experiments involving a single loaded compound) or 50 µM (for experiments involving two loaded compounds). Error bars represent the standard error of three independent replicates (n=3). ***=p<0.0005.

As shown in FIG. 18, SLIPS loaded with V-06-018 and E22 inhibited pyocyanin production by approximately 80% and 45%, respectively. These values are equivalent to the levels of pyocyanin inhibition observed when these compounds are administered exogenously, indicating that both of these compounds are released from the SLIPS-coated surfaces in intact, biologically-active forms and in concentrations sufficient to inhibit QS under these assay conditions. Although not investigated specifically as part of this study, it is noted that the overall strategy used here, in which encapsulated payloads are stored within a polymer matrix infused with a hydrophobic and water-immiscible oil—and, thus, largely protected from contact with bulk water until they diffuse across the oil/water interface—could prove useful for the prolonged release of active agents that hydrolyze or decompose readily upon contact with water. For instance, it is well known that AHLs hydrolyze relatively rapidly in aqueous media and that the ring-opened forms are inactive; we anticipate that SLIPs containing AHLs (such as E22 and C12) could provide means for extending their effective half-lives in water, and thus extending their utility as QSIs.

It was previously demonstrated that cocktails of compounds targeting multiple different QS circuits could result in greater attenuation of virulence factor production (as compared to levels attenuated upon the administration of a single compound targeting a single QS circuit) (see Welsh, M. A., and Blackwell, H. E. (2016) Chemical genetics reveals environment-specific roles for quorum sensing circuits in *Pseudomonas aeruginosa*, *Cell Chem. Biol.* 23, 361-369). To explore the potential of our polymer-based SLIPS to promote the simultaneous release of two different active agents, and develop SLIPS-coated surfaces that attenuate QS more strongly than those described above, SLIPS were prepared loaded with both V-06-018 and E22 (in amounts designed to give approximately 50 µM of each compound in the assay culture upon full release) and pyocyanin production was quantified when the compounds were released simultaneously. Over 90% inhibition of pyocyanin production was observed using this dual-release approach (FIG. 18). This dual-QSI release approach allows for lower loadings of each individual agent and promotes levels of inhibition greater than those exhibited when either agent is used alone because it targets both RhlR and LasR QS receptors simultaneously.

The ease with which these QSIs (and other acetone-soluble agents) can be loaded into these nanoporous multilayers, without necessitating any changes to the fabrication process, suggests that this basic approach should be general and that these SLIPS systems should be appropriate for use in other applications that would benefit from the simultaneous release of single or multiple different active agents.

It is noted that the SLIPS-coated substrates emerging from these in situ virulence factor production experiments remained anti-fouling to bacteria, but exhibited water droplet sliding angles higher than those that were measured prior to incubation with bacteria (e.g., droplets of water required tilt angles of ~30° or more to slide freely, as compared to sliding angles of <10° for substrates prior to incubation as shown in Table 1), suggesting that some oil may have been lost from the SLIPS during those experiments. Additional control experiments demonstrated this decrease in droplet sliding angles to result from incubation at the high densities of bacteria required for these pyocyanin assays (incubation under static conditions at lower densities of bacteria or shaking in the absence of bacteria did not affect droplet sliding angles). It has been reported in past studies that exposure to high shear forces (induced by flow, etc.) can promote the leaching of the infused liquid phases of SLIPS in ways that can impact their slippery properties (see Howell, C., Vu, T. L., Johnson, C. P., Hou, X., Ahanotu, O., Alvarenga, J., Leslie, D. C., Uzun, O., Waterhouse, A., Kim, P., Super, M., Aizenberg, M., Ingber, D. E., and Aizenberg, J. (2015) Stability of Surface-Immobilized Lubricant Interfaces under Flow, *Chem. Mater.* 27, 1792-1800; Howell, C., Vu, T. L., Lin, J. J., Kolle, S., Juthani, N., Watson, E., Weaver, J. C., Alvarenga, J., and Aizenberg, J. (2014) Self-Replenishing Vascularized Fouling-Release Surfaces, *ACS Appl. Mater. Inter.* 6, 13299-13307.) It is also possible in this current context that the presence of amphiphilic molecules produced by the bacterial cultures used here (i.e., lipids, lipid assemblies, etc.) could help promote the extraction of small amounts of oil over the course of these experiments. In support of this proposition, we note that sliding angles could be restored to values of 10° or less by adding small amounts of silicone oil to the surface of the coatings (e.g., by pipette). Past reports also demonstrate that the gradual loss of infused oil can be addressed in other practical ways, including through the design of porous substrates with oil reserves that can continually replenish lost oil (Howell, C., Vu, T. L., Lin, J. J., Kolle, S., Juthani, N., Watson, E., Weaver, J. C., Alvarenga, J., and Aizenberg, J. (2014) Self-Replenishing Vascularized Fouling-Release Surfaces, *ACS Appl. Mater. Inter.* 6, 13299-13307). Despite the increase in water droplet sliding angles observed in these experiments, the results of additional experiments described below demonstrate that these compound-loaded SLIPS-coated substrates remain anti-fouling to bacteria under similar culture conditions and can prevent the formation of bacterial biofilms.

DMABI-Loaded SLIPS Reduce Biofilm Formation on Surrounding Uncoated Surfaces.

As described above, the native silicone oil-infused SLIPS used in this study have been demonstrated to resist the formation of *P. aeruginosa* biofilms under static culture conditions (e.g., in the absence of added agents). To demonstrate the potential of controlled-release SLIPS to also prevent biofilm formation in surrounding environments—and, thus, also confer measures of anti-biofouling protection to nearby surfaces that are not SLIPS-coated—studies using SLIPS loaded with the anti-biofilm agent DMABI were also performed.

For these studies, *P. aeruginosa* was cultured in 12-well microtiter plates containing DMABI-loaded SLIPS substrates in the well bottoms (such that they were completely submerged in media). After 24 hours of incubation, the amount of surface-attached biofilm on both the SLIPS substrates and the surrounding (uncoated) areas of the well bottoms was characterized by fluorescence microscopy and by staining with crystal violet (CV). The SLIPS substrates were highly resistant to biofilm attachment, as expected from past studies (Manna et al., "Slippery liquid-infused porous surfaces that prevent microbial surface fouling and kill non-adherent pathogens in surrounding media: A controlled release approach," Advanced Functional Materials, 2016, 26(21):3599-3611). No biofilm was observed over the entire central region of the coated substrates by fluorescence microscopy, and little to no CV staining on the SLIPS surface (FIG. 19 (A-B)).

Figure 19:
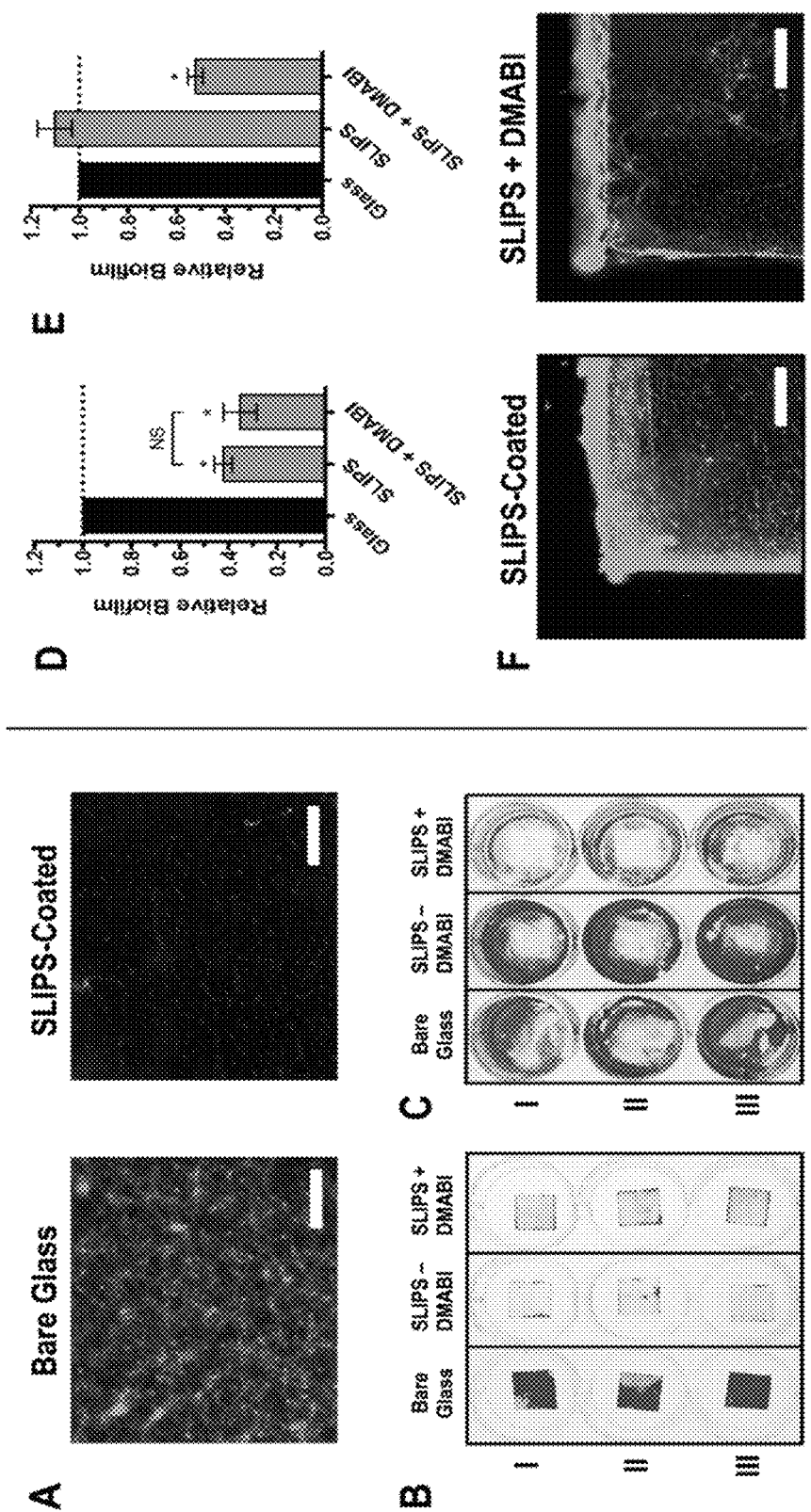
FIG. 19: SLIPS loaded with DMABI resist fouling on the substrate surface and inhibit biofilm formation on surrounding uncoated surfaces. Glass or SLIPS-coated substrates were submerged in *P. aeruginosa* cultures at the bottoms of the wells of 12-well microtiter plates and incubated for 24 h. Substrates were then removed and the attached biofilms were stained with either SYTO 9 or CV. (A) Representative fluorescence microscopy images of *P. aeruginosa* biofilm near to the center of glass (left) or SLIPS-coated (right) substrates. (B) Representative image of CV-stained biofilms attached to glass substrates, SLIPS, or SLIPS loaded with DMABI. (C) Representative image of CV staining of the bottoms of the wells of the 12-well microtiter plate (after the removal of the substrates; shown in panel A). (D) Quantification of biofilm formed on the glass and SLIPS substrates shown in panel B. (E) Quantification of biofilm formed on the surrounding well bottoms shown in panel C, showing a reduction of biofilm in wells that contained DMABI-loaded SLIPS. (F) Representative fluorescence microscopy images of biofilm formed on the exposed glass edges of SLIPS substrates without DMABI (left) and with loaded DMABI (right). Scale bars in A and F represent 400 µm. Error bars in D and E represent the standard error of three independent experiments (n=3). *=p<0.05. NS=no statistical difference.

When the amount of CV on the SLIPS was quantified by UV/vis spectrophotometry, more CV was observed than expected by visual inspection (corresponding to an approximately 50% reduction in staining; FIG. 19 (D)). It was determined, using fluorescence microscopy, that this residual staining was a result of the presence of biofilm near the uncoated edges of the SLIPS-coated substrates (FIG. 19 (F)), and not a result of biofilm on the SLIPS surfaces themselves. These uncoated edges are a result of the manner in which the SLIPS-coated substrates were prepared for these proof-of-concept studies (e.g., by the fracture of larger 'parent' SLIPS-coated surfaces into smaller 'daughter' chips; see the above experimental sections for details) and are not an inherent limitation of the SLIPS surfaces themselves.

As expected, native (unloaded) SLIPS had no significant influence on the formation of *P. aeruginosa* biofilms in regions of the surrounding (uncoated) well bottoms in these studies (FIG. 19 (C,E)). DMABI-loaded SLIPS, however, prevented biofilm attachment on the SLIPS-coated surface by CV staining (FIG. 19 (B,D)) and inhibited biofilm formation on the surrounding uncoated well bottoms by approximately 50% (FIG. 19 (C,E))—a result that is attributed to the gradual release of imbedded DMABI into surrounding media (consistent with results shown in FIG. 17). It is likely that the levels of inhibition observed on uncoated well bottoms in these experiments (and the observation of persistent biofilm on the uncoated edges of the SLIPS-coated substrates, as noted above) could be improved further by increasing the loading of DMABI or tuning the rate at which it is released through modifications to the structure of the polymer matrix of the properties of the infused oil (the extended release profile shown in FIG. 17 suggests that only small amounts of DMABI were likely to have been released from these silicone oil-infused SLIPS over the course of these short-term experiments). Efforts to optimize and completely eradicate biofilm formation in the model system used here were not pursued as part of these proof-of-concept studies, but would be straightforward to implement during the development or evaluation of these materials in application-specific contexts or environments.

Summary and Conclusions.

Materials and surface coatings that are resistant to bacterial colonization and that can simultaneously inhibit bacterial virulence phenotypes on and around their surfaces would be useful in a range of biomedical, environmental, and industrial contexts. Materials that can accomplish both of these important tasks without impacting bacterial growth would be particularly valuable, as they would also have the potential to avoid serious problems associated with the development of evolved resistance that currently plague traditional bactericidal approaches. The work described here provides such materials by developing new slippery and anti-fouling oil-infused surfaces that can be used as a robust platform for the controlled release or delivery of small-molecule QSIs and biofilm inhibitors. These results demonstrate that this novel approach can significantly (i) reduce production of a virulence factor by planktonic bacteria in the vicinity of the surface and (ii) reduce the biofilm burden on the surface of the material itself and on surrounding non-SLIPS-coated surfaces. These results also demonstrate that this controlled-release SLIPs approach can be used to load and release of combinations or 'cocktails' of these agents that may be more effective than any single antibiotic or QSI alone.

The methods used to fabricate these slippery coatings can be used to coat topologically complex substrates, including tubing, filters, or implants, and should thus allow for protection against surface fouling and facilitate the local, controlled delivery of anti-virulence agents directly to sites endemic to bacterial colonization in medical devices and/or industrial equipment. The modular nature of these SLIPS also provides opportunities to tune the slippery and controlled release properties of these coatings though changes in the structure of the polymer matrix, the physicochemical properties of the infused oil phase, and the solubilities and structures of the small-molecule agents that are loaded. The approaches and new strategies described here can thus form the basis of a general and multi-functional materials platform that are useful for combating bacterial biofouling and virulence via non-biocidal pathways in a range of important fundamental and applied contexts.

Example 5—Design of Controlled Release SLIPS Loaded with Tertamethylrhodamine

Experiments were conducted comparing the release rates of tertamethylrhodamine (TMR) from SLIPS prepared by infusing a porous polymer matrix with a saturated solution of TMR in silicone oil, and SLIPS prepared by first loading TMR directly into a polymer matrix and then infusing with the silicone oil.

Figure 20A:
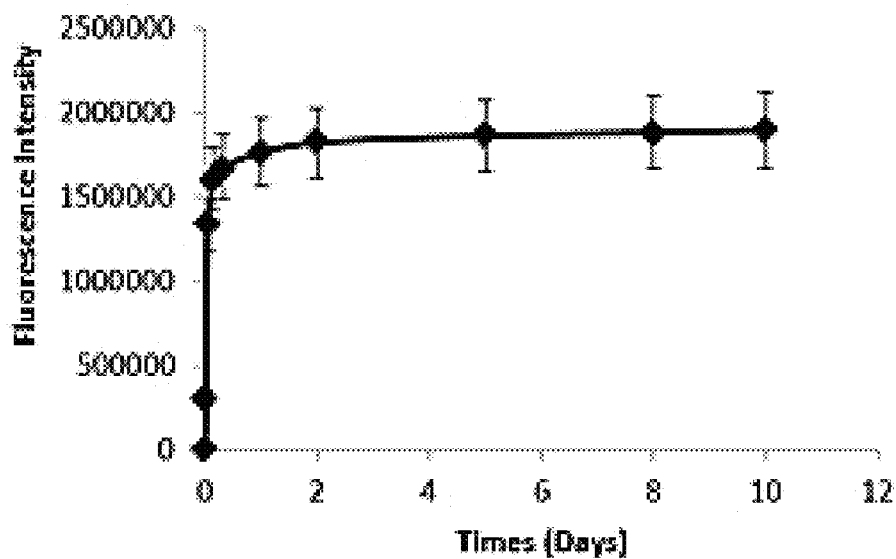
FIG. 20A and FIG. 20B: Plot showing a release curve (determined using fluorescence intensity) of a fluorophore (tetramethyl rhodamine; TMR) which was loaded into SLIPS by loading TMR into silicone oil and then infusing the TMR/oil solution into the polymer matrix (FIG. 20A). Plot showing a release curve of TMR which was loaded into SLIPS by first loading TMR into the matrix followed by infusing the matrix with the silicone oil (FIG. 20B).
Figure 20B:
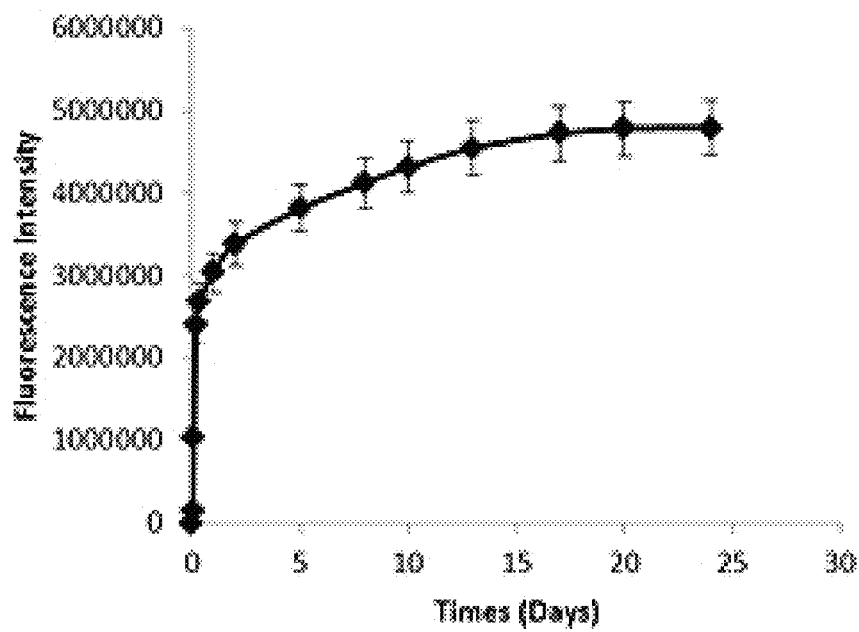

A saturated solution of tertamethylrhodamine (TMR) in silicone oil was first prepared by adding 0.5 mg of TMR to 20 mL of silicone oil, maintaining it on a shaker plate for 24 hours, and then removing undissolved TMR by centrifugation at 5000 rmp for 2 min. 3 µL of this TMR/silicone oil solution was then spread on and infused into dried nanoporous PEI/PVDMA multilayers. The release of TMR was characterized by incubating these TMR-loaded SLIPS in PBS. A release curve arising from samples prepared in this way is provided in FIG. 20 (A) and shows that release occurred rapidly.

Next, SLIPS were prepared by loading the TMR onto the polymer matrix before addition of the oil. Briefly, 10 µL of a solution of TMR in acetone (0.02 mg/mL) was placed on dried nanoporous PEI/PVDMA multilayers and allowed to dry as described in previous examples. 3 µL of silicone oil was then spread on and infused into the polymer matrix. The release of TMR was characterized by incubating these TMR-loaded SLIPS in PBS. A release curve arising from samples prepared in this way is provided in FIG. 20 (B) and shows (i) that release occurred more slowly than the example in which TMR was loaded in the oil phase only (FIG. 20 (A)), and (ii) the loading was higher using this method, because this approach circumvents limitations related to the solubility of TMR in silicone oil and allows greater amounts of TMR to be loaded prior to oil infusion.

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

One of ordinary skill in the art will appreciate that starting materials, reagents, purification methods, materials, substrates, device elements, analytical methods, assay methods, mixtures and combinations of components other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that the use of such terms and expressions exclude any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

When a group of materials, compositions, components or compounds is disclosed herein, it is understood that all individual members of those groups and all subgroups thereof are disclosed separately. When a Markush group or other grouping is used herein, all individual members of the group and all combinations and subcombinations possible of the group are intended to be individually included in the disclosure. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure. In the disclosure and the claims, "and/or" means additionally or alternatively. Moreover, any use of a term in the singular also encompasses plural forms.

All references cited herein are hereby incorporated by reference in their entirety to the extent that there is no inconsistency with the disclosure of this specification. Some references provided herein are incorporated by reference to provide details concerning sources of starting materials, additional starting materials, additional reagents, additional methods of synthesis, additional methods of analysis, additional biological materials, and additional uses of the invention. All headings used herein are for convenience only. All patents and publications mentioned in the specification are indicative of the levels of skill of those skilled in the art to which the invention pertains, and are herein incorporated by reference to the same extent as if each individual publication, patent or patent application was specifically and individually indicated to be incorporated by reference. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

The invention claimed is:

1. A slippery liquid-infused porous surface (SLIPS) that controllably releases a molecule, wherein said slippery oil-infused surface comprises:
    a) a porous matrix having nanoscale or microscale porosity;
    b) an oil covering at least a portion of the porous matrix, wherein said oil at least partially fills the pores of the porous matrix; and
    c) one or more small-molecule compounds, wherein the one or more small-molecule compounds are located on the surface or in said porous matrix, within said oil, or both,
    wherein the slippery oil-infused surface is able to controllably release the one or more small-molecule compounds when the slippery oil-infused surface is immersed into media.

2. The slippery oil-infused surface of claim 1 wherein the oil is selected from the group consisting of a silicone oil, a vegetable oil, a mineral oil, a perfluorinated oil, a thermotropic liquid crystal, and combinations thereof.

3. The slippery oil-infused surface of claim 1 wherein the one or more smal molecule compounds is able to reduce, inhibit, or modulate the behaviors of non-adherent pathogens in surrounding media.

4. The slippery oil-infused surface of claim 1 wherein the one or more small-molecule compounds is a natural or synthetic antibiotic agent, a natural or synthetic antifungal agent, an agent that modulates bacterial or fungal quorum sensing, an agent that attenuates virulence, or a combination thereof.

5. The slippery oil-infused surface of claim 4 wherein the one or more small-molecule compounds is selected from the group consisting of acyl L-homoserine lactone (AHL) derivatives, aminobenzimidazole (ABI) derivatives, and combinations thereof.

6. The slippery oil-infused surface of claim 1 wherein the one or more small-molecule compounds is selected from the group consisting of:

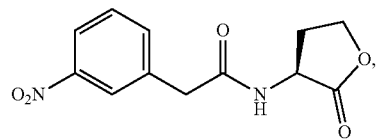

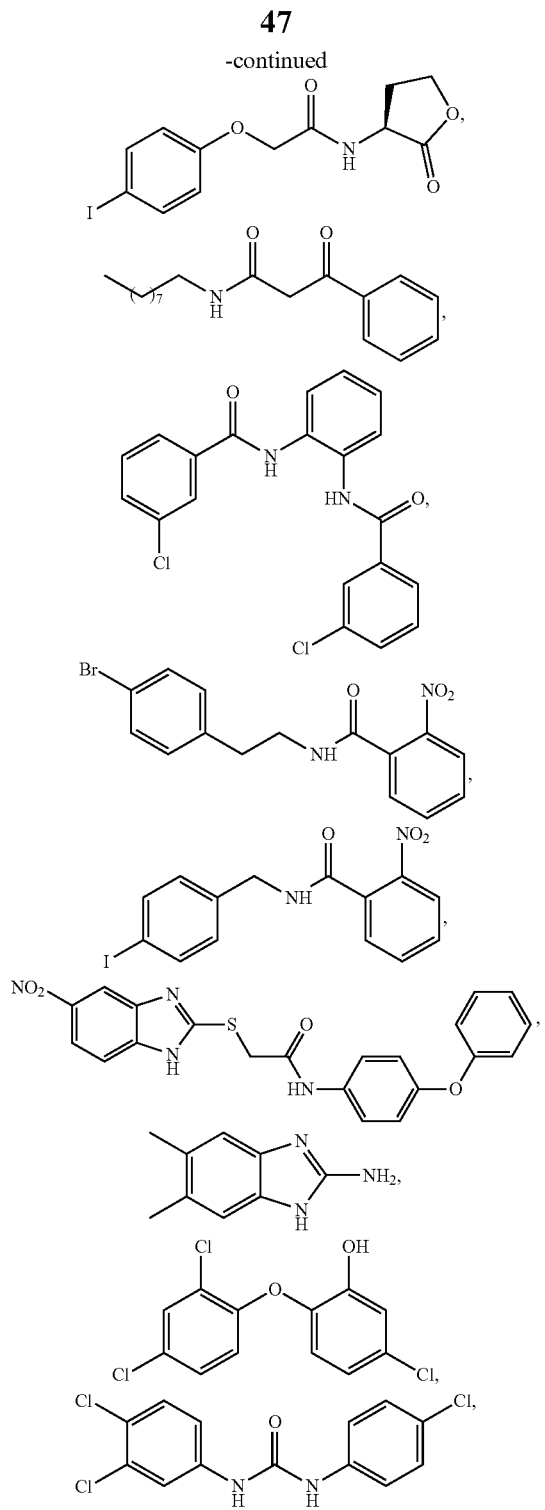

or combinations thereof.

7. The slippery oil-infused surface of claim 1 wherein the porous matrix comprises a multilayer film having one or more bilayers, wherein each bilayer comprises a first polymer layer in contact with a second polymer layer, where said multilayer film has nanoscale or microscale porosity.

8. The slippery oil-infused surface of claim 7 wherein the first polymer layer comprises functionalized azlactones having the formula:

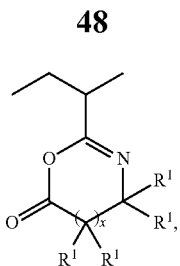

wherein x is 0 or the integers 1 or 2; and each $R^1$ is independently selected from the group consisting of: hydrogen, alkyl groups, alkenyl groups, alkynyl groups, carbocyclic groups, heterocyclic groups, aryl groups, heteroaryl groups, alkoxy groups, aldehyde groups, ether groups, and ester groups, any of which may be substituted or unsubstituted.

9. The slippery oil-infused surface of claim 7 wherein the first polymer layer comprises a polymer selected from the group consisting of poly(vinyl-4,4-dimethylazlactone), poly (2-vinyl-4,4-dimethyl-2-oxazolin-5-one), poly(2-isoprope-nyl-4,4-dimethyl-2-oxazolin-5-one), poly(2-vinyl-4,4-di-ethyl-2-oxazolin-5-one), poly(2-vinyl-4-ethyl-4-methyl-2-oxazolin-5-one), poly(2-vinyl-4-dodecyl-4-methyl-2-oxazolin-5-one), poly(2-vinyl-4,4-pentamethylene-2-oxazolin-5-one), poly (2-vinyl-4-methyl-4-phenyl-2-oxazolin-5-one), poly(2-isopropenyl-4-benzyl-4-methyl-2-oxazolin-5-one), or poly(2-vinyl-4,4-dimethyl-1,3-oxazin-6-one).

10. The slippery oil-infused surface of claim 7 wherein the second polymer layer comprises a primary amine functionalized polymer, an alcohol functionalized polymer, or a thiol functionalized polymer.

11. The slippery oil-infused surface of claim 7 comprising one or more PVDMA/PEI bilayers, which are further functionalized with n-decylamine and wherein the one or more bilayers are infused with a silicone oil or an anisotropic thermotropic liquid crystal.

12. A method for fabricating a nanoporous or microporous slippery liquid-infused porous surface (SLIPS) able to reduce, inhibit, or modulate the behaviors of non-adherent pathogens in surrounding media, said method comprising the steps of:
   a) forming a porous matrix on a substrate, wherein said porous matrix has nanoscale or microscale porosity;
   b) exposing the porous matrix to an oil, wherein said oil covers at least a portion of the porous matrix and said oil at least partially fills the pores of at least a portion of said porous matrix, wherein the oil is selected from the group consisting of a silicone oil, a vegetable oil, a mineral oil, a perfluorinated oil, a thermotropic liquid crystal, and combinations thereof; and
   c) loading one or more small-molecule compounds onto the surface of or in said porous matrix or into said oil, wherein the slippery oil-infused surface is able to controllably release the one or more small-molecule compounds when the slippery oil-infused surface is immersed into said media.

13. A method for reducing, inhibiting, or modulating the behaviors of non-adherent pathogens in media surrounding a substrate comprising the steps of:
   a) providing a slippery liquid-infused porous surface (SLIPS) on the substrate, said slippery oil-infused surface comprising:
      i) a porous matrix having nanoscale or microscale porosity;

ii) an oil covering at least a portion of the porous matrix, wherein said oil at least partially fills the pores of the porous matrix, wherein the oil is selected from the group consisting of a silicone oil, a vegetable oil, a mineral oil, a perfluorinated oil, a thermotropic liquid crystal, and combinations thereof; and iii) one or more small-molecule compounds able to reduce, inhibit, or modulate the behaviors said pathogens upon contact with said pathogens, wherein the one or more small-molecule compounds are located on the surface of said porous matrix, within said oil, or both;

b) controllably releasing the one or more small-molecule compounds from said slippery liquid-infused porous surface into said media when the slippery oil-infused surface is immersed into said media, wherein the one or more small-molecule compounds contact the pathogens thereby reducing the number of pathogens, inhibiting the growth or colonization of the pathogens, or modulating the behaviors of the pathogens.

14. The method of claim 13 wherein the one or more small-molecule compounds is an antimicrobial agent, an antifungal agent, an antibacterial agent, an agent that modulates bacterial or fungal quorum sensing, an agent that attenuates virulence, or a combination thereof.

15. The method of claim 13 wherein the one or more small-molecule compounds is a natural or synthetic antibiotic agent, natural or synthetic antifungal agent, quorum sensing modulator, or a combination thereof.

16. The method of claim 13 wherein the one or more small-molecule compounds is selected from the group consisting of AHL derivatives, ABI derivatives, and combinations thereof.

17. The method of claim 13 wherein the one or more small-molecule compounds is selected from the group consisting of:

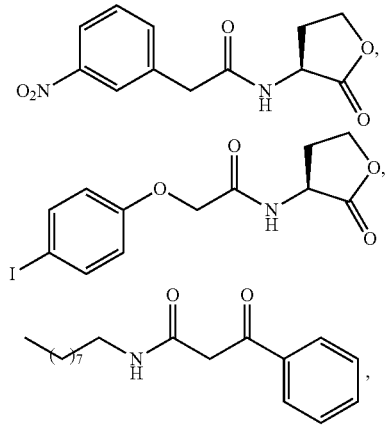

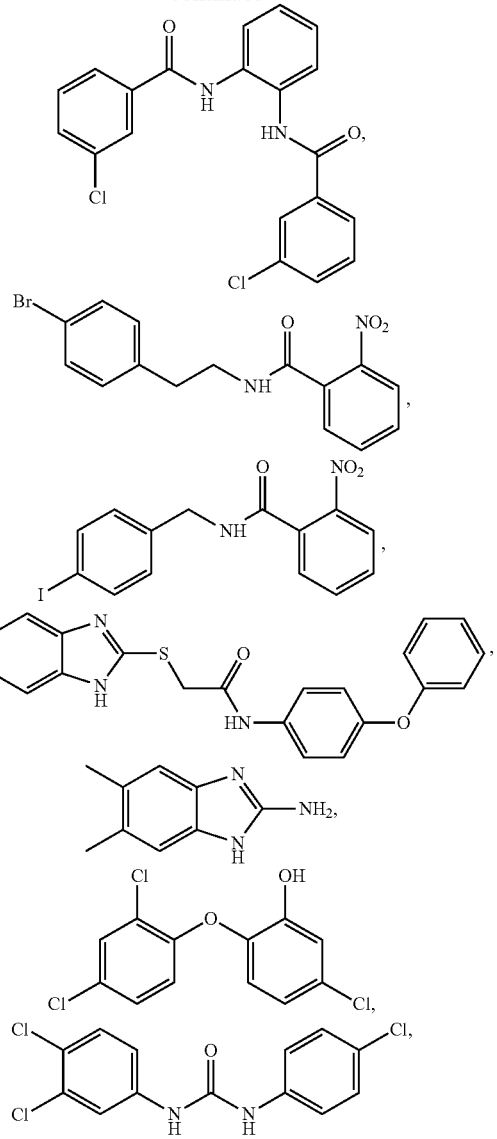

or combinations thereof.

18. The method of claim 13 wherein the non-adherent pathogens are bacteria, fungi, or a combination thereof.

19. The method of claim 13 wherein the porous matrix comprises a multilayer film having one or more bilayers, wherein each bilayer comprises a first polymer layer in contact with a second polymer layer, where said multilayer film has nanoscale or microscale porosity.

20. The method of claim 13 further comprising the step of loading an additional one or more small-molecule compound within the oil when levels of small-molecule compounds drop below a desired level.

* * * * *